(12) United States Patent
Gomtsyan et al.

(10) Patent No.: US 8,084,616 B2
(45) Date of Patent: Dec. 27, 2011

(54) TRPV1 ANTAGONISTS

(75) Inventors: Arthur R. Gomtsyan, Vernon Hills, IL (US); Robert G. Schmidt, Waukegan, IL (US); Erol K. Bayburt, Gurnee, IL (US); Jerome F. Daanen, Racine, WI (US); Michael E. Kort, Lake Bluff, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 12/256,924

(22) Filed: Oct. 23, 2008

(65) Prior Publication Data

US 2009/0124671 A1    May 14, 2009

Related U.S. Application Data

(60) Provisional application No. 60/982,200, filed on Oct. 24, 2007.

(51) Int. Cl.
C07D 213/56 (2006.01)
A61K 31/44 (2006.01)

(52) U.S. Cl. ........................ 546/337; 514/357

(58) Field of Classification Search .............. 546/337; 514/357
See application file for complete search history.

(56) References Cited

FOREIGN PATENT DOCUMENTS

WO  WO-2005004866 A1  1/2005
WO  WO-2005009987 A1  2/2005

OTHER PUBLICATIONS

Patani et. al., "Bioisosterism: A Rational Approach in Drug Design", Chem. Rev. 1996, 96, pp. 3147-3176.*
Caplus 2007:230718, "Cyclohexenylamine derivatives and as inhibitors of dipeptidyl peptidase-iv (DPP-IV) and their preparation, pharmaceutical compositions and use in the treatment of various diseases", Pei et. al.*
Hcaplus 2006:1042526, Discovery of ((4R, 5S)-5-Amino-4-(2,4,5-trifluorophenyl)cyclohex-2-enyl)-(3-(trifluormethyl)-5,6-dihydro[1,2,4]-triazolo[4,3-a]pyrazin-7 (8H)-yl)methanone (ABT-341), a Highly Potent, Selective, Orally Efficacious, and Safe Dipeptidyl Peptidase IV Inhibitor for the Treatment of Type 2 Diabetes, Pei et. al., 2006.*
Patani et. al., "Bioiososterism: A Rational Approach in Drug Design", Chem. Rev. 1996, 96, pp. 3147-3176.*

* cited by examiner

Primary Examiner — Janet Andres
Assistant Examiner — Heidi Reese
(74) Attorney, Agent, or Firm — Lisa V. Mueller; Michael Best & Friedrich LLP

(57) ABSTRACT

The present invention relates to compounds of formula (I)

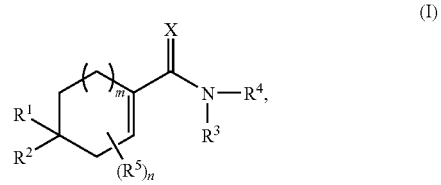

(I)

wherein X, $R^1$, $R^2$, $R^3$, $R^4$, $R^5$, m, and n are defined in the specification are TRPV1 antagonists. Compositions comprising such compounds and methods for treating conditions and disorders using such compounds and compositions are also disclosed.

13 Claims, No Drawings

TRPV1 ANTAGONISTS

This application claims priority to U.S. Ser. No. 60/982,200, filed Oct. 24, 2007 and is incorporated herein by reference.

TECHNICAL FIELD

The present invention generally relates to cycloalkene containing compounds, compositions comprising such compounds, and methods of treating conditions and disorders using such compounds and compositions.

BACKGROUND

Nociceptors are primary sensory afferent (C and Aδ fibers) neurons that are activated by a wide variety of noxious stimuli including chemical, mechanical, thermal, and proton (pH<6) modalities. The lipophillic vanilloid, capsaicin, activates primary sensory fibers via a specific cell surface capsaicin receptor, cloned as the transient receptor potential vanilloid-1 (TRPV 1). TRPV1 is also known as vanilloid receptor-1 (VR1). The intradermal administration of capsaicin is characterized by an initial burning or hot sensation followed by a prolonged period of analgesia. The analgesic component of the TRPV1 receptor activation is thought to be mediated by a capsaicin-induced desensitization of the primary sensory afferent terminal. Thus, the long lasting anti-nociceptive effect of capsaicin has prompted the clinical use of capsaicin analogs as analgesic agents. Further, capsazepine, a capsaicin receptor antagonist can reduce inflammation-induced hyperalgesia in animal models. TRPV1 receptors are also localized on sensory afferents, which innervate the bladder. Capsaicin or resiniferatoxin has been shown to ameliorate incontinence symptoms upon injection into the bladder.

The TRPV1 receptor has been called a "polymodal detector" of noxious stimuli since it can be activated in several ways. The receptor channel is activated by capsaicin and other vanilloids, and thus is classified as a ligand-gated ion channel. The TRPV1 receptor activation by capsaicin can be blocked by the competitive TRPV1 receptor antagonist, capsazepine. The channel can also be activated by protons. Under mildly acidic conditions (pH 6-7), the affinity of capsaicin for the receptor is increased, whereas at pH<6, direct activation of the channel occurs. In addition, when membrane temperature reaches 43° C., the channel is opened. Thus heat can directly gate the channel in the absence of ligand. The capsaicin analog, capsazepine, which is a competitive antagonist of capsaicin, blocks activation of the channel in response to capsaicin, acid, or heat.

The channel is a nonspecific cation conductor. Both extracellular sodium and calcium enter through the channel pore, resulting in cell membrane depolarization. This depolarization increases neuronal excitability, leading to action potential firing and transmission of a noxious nerve impulse to the spinal cord. In addition, depolarization of the peripheral terminal can lead to release of inflammatory peptides such as, but not limited to, substance P and CGRP, leading to enhanced peripheral sensitization of tissue.

Recently, two groups have reported the generation of a "knock-out" mouse lacking the TRPV1 receptor. Electrophysiological studies of sensory neurons (dorsal root ganglia) from these animals revealed a marked absence of responses evoked by noxious stimuli including capsaicin, heat, and reduced pH. These animals did not display any overt signs of behavioral impairment and showed no differences in responses to acute non-noxious thermal and mechanical stimulation relative to wild-type mice. The TRPV1 (−/−) mice also did not show reduced sensitivity to nerve injury-induced mechanical or thermal nociception. However, the TRPV1 knock-out mice were insensitive to the noxious effects of intradermal capsaicin, exposure to intense heat (50-55° C.), and failed to develop thermal hyperalgesia following the intradermal administration of carrageenan.

We herein describe a novel series of TRPV1 antagonists.

SUMMARY

The present invention generally provides cycloalkenes containing compounds and pharmaceutical compositions and methods for the treatment of disorders using these compounds and pharmaceutical compositions.

One aspect of the invention is directed towards compounds of formula (I), or pharmaceutically acceptable salts, prodrugs, salts of prodrugs, or combinations thereof,

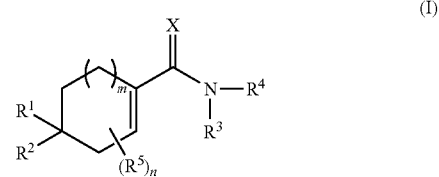

wherein
$R^1$ is phenyl or a monocyclic heteroaryl, each of which is optionally substituted with 1, 2, 3, 4, or 5 substituents as represented by $R^6$ groups;
$R^2$ is halogen, alkyl, haloalkyl, —CN, —O(alkyl), —O(haloalkyl), —OH, —NH$_2$, —N(H)(alkyl), or —N(alkyl)$_2$; or
$R^2$ and the adjacent carbon atom, together with the carbon atom to which $R^2$ is attached, form a 3-6 membered monocyclic cycloalkyl ring that is optionally substituted with 1, 2, 3, or 4 substituents independently selected from the group consisting of alkyl, hydroxyalkyl, alkoxyalkyl, haloalkoxyalkyl, haloalkyl, arylalkyl, aryl, aminoalkyl, amino, and halogen, wherein the aryl and the aryl moiety of the arylalkyl are each independently unsubstituted or substituted with 1, 2, 3, 4, or 5 substituents selected from the group consisting of alkyl, alkenyl, alkynyl, halogen, OH, O(alkyl), O(haloalkyl), amino, and haloalkyl;
$R^3$ is hydrogen or $C_{1-6}$ alkyl;
$R^4$ is aryl, heteroaryl, cycloalkyl, cycloalkenyl, or heterocycle, wherein each $R^4$ is optionally substituted with 1, 2, 3, 4, 5, or 6 substituents as represented by $R^7$ groups;
$R^5$ represents an optional substituent on the cycloalkene ring, and is haloalkyl, halogen, —OH, —NO$_2$, NH$_2$, N(H)(alkyl), N(alkyl)$_2$, alkyl, alkenyl, alkynyl, or -G$^1$;
X is O, S, or N($R^z$) wherein $R^z$ is hydrogen, alkyl, or CN;
m is 0, 1, or 2;
n is 0 or 1;
$R^7$, at each occurrence, is independently alkyl, alkenyl, alkynyl, oxo, —NO$_2$, —CN, halogen, -G$^2$, —OR$^a$, —OC(O)R$^a$, —SR$^a$, —SF$_5$, —S(O)R$^b$, —S(O)$_2$R$^b$, —S(O)$_2$N(R$^a$)(R$^c$), —N(R$^a$)(R$^c$), —N(R$^c$C)C(O)R$^a$, —N(R$^c$)S(O)$_2$R$^b$, —N(R$^c$)C(O)N(R$^a$)(R$^c$), —N(R$^c$)S(O)$_2$N(R$^a$)(R$^c$), —C(O)R$^a$, —C(O)O(R$^a$), —C(O)N(R$^a$)(R$^c$), haloalkyl, —(CR$^j$R$^k$)$_p$—CN, —(CR$^j$R$^k$)$_p$—OR$^a$, —(CR$^j$R$^k$)$_p$—OC(O)R$^a$, —(CR$^j$R$^k$)$_p$—SR$^a$, —(CR$^j$R$^k$)$_p$—S(O)R$^b$, —(CR$^j$R$^k$)$_p$—S(O)$_2$R$^b$, —(CR$^j$R$^k$)$_p$—N(R$^a$)(R$^c$), —(CR$^j$R$^k$)$_p$—N(R$^c$)C(O)R$^a$, —(CR$^j$R$^k$)$_p$—N(R$^c$)S(O)$_2$R$^b$, —(CR$^j$R$^k$)$_p$—N(R$^c$)C(O)N $(R^a)(R^c)$, $(CR^jR^k)_p$—N$(R^c)$S(O)$_2$N$(R^a)(R^c)$, —$(CR^jR^k)_p$—C(O)R$^a$, —$(CR^jR^k)_p$—C(O)O$(R^a)$, —$(CR^jR^k)_p$—C(O)N$(R^a)(R^c)$, or —$(CR^jR^k)_p$-G$^2$;

R$^a$, at each occurrence, is independently hydrogen, alkyl, haloalkyl, -G$^2$, or —$(CR^uR^v)_w$-G$^2$;

R$^b$, at each occurrence, is independently alkyl, haloalkyl, -G$^2$, or —$(CR^uR^v)_w$-G$^2$;

G$^1$ and G$^2$, are each independently aryl, heteroaryl, cycloalkyl, cycloalkenyl, or heterocycle; each of which is independently unsubstituted or substituted with 1, 2, 3, 4, 5, or 6 substituents as represented by R$^8$ groups;

R$^6$, at each occurrence, is independently alkyl, alkenyl, alkynyl, —NO$_2$, —CN, halogen, —OR$^d$, —OC(O)R$^d$, —SR$^d$, —S(O)R$^e$, —S(O)$_2$R$^e$, —S(O)$_2$N$(R^d)(R^f)$, —N$(R^d)(R^f)$, —N$(R^f)$C(O)R$^d$, —N$(R^f)$S(O)$_2$R$^e$, —N$(R^f)$C(O)N$(R^d)(R^f)$, —N$(R^f)$S(O)$_2$N$(R^d)(R^f)$, —C(O)R$^d$, —C(O)O$(R^d)$, —C(O)N$(R^d)(R^f)$, haloalkyl, —$(CR^sR^t)_q$—CN, —$(CR^sR^t)_q$—OR$^a$, —$(CR^sR^t)_q$—SR$^d$, —$(CR^sR^t)_q$—S(O)R$^e$, —$(CR^sR^t)_q$—S(O)$_2$R$^e$, —$(CR^sR^t)_q$—N$(R^d)(R^f)$, —$(CR^sR^t)_q$—N$(R^f)$C(O)R$^d$, —$(CR^sR^t)_q$—N$(R^f)$S(O)$_2$R$^e$, —$(CR^sR^t)_q$—N$(R^f)$C(O)N$(R^d)(R^f)$, —$(CR^sR^t)_q$—N$(R^f)$S(O)$_2$N$(R^d)(R^f)$, —$(CR^sR^t)_q$—C(O)R$^d$, —$(CR^sR^t)_q$—C(O)O$(R^d)$, or —$(CR^sR^t)_q$—C(O)N$(R^d)(R^f)$;

R$^8$, at each occurrence, is independently alkyl, alkenyl, alkynyl, oxo, —NO$_2$, —CN, halogen, —OR$^d$, —OC(O)R$^d$, —SR$^d$, —S(O)R$^e$, —S(O)$_2$R$^e$, —S(O)$_2$N$(R^d)(R^f)$, —N$(R^d)(R^f)$, —N$(R^f)$C(O)R$^d$, —N$(R^f)$S(O)$_2$R$^e$, —N$(R^f)$C(O)N$(R^d)(R^f)$, —N$(R^f)$S(O)$_2$N$(R^d)(R^f)$, —C(O)R$^d$, —C(O)O$(R^d)$, —C(O)N$(R^d)(R^f)$, haloalkyl, —$(CR^sR^t)_q$—CN, —$(CR^sR^t)_q$—OR$^a$, —$(CR^sR^t)_q$—OC(O)R$^d$, —$(CR^sR^t)_q$—SR$^d$, —$(CR^sR^t)_q$—S(O)R$^e$, —$(CR^sR^t)_q$—S(O)$_2$R$^e$, —$(CR^sR^t)_q$—N$(R^d)(R^f)$, —$(CR^sR^t)_q$—N$(R^f)$C(O)R$^d$, —$(CR^sR^t)_q$—N$(R^f)$S(O)$_2$R$^e$, —$(CR^sR^t)_q$—N$(R^f)$C(O)N$(R^d)(R^f)$, —$(CR^sR^t)_q$—N$(R^f)$S(O)$_2$N$(R^d)(R^f)$, —$(CR^sR^t)_q$—C(O)R$^d$, —$(CR^sR^t)_q$—C(O)O$(R^d)$, or —$(CR^sR^t)_q$—C(O)N$(R^d)(R^f)$;

R$^c$, R$^d$ and R$^f$, at each occurrence, are each independently hydrogen, alkyl, or haloalkyl;

R$^e$, at each occurrence, is independently alkyl or haloalkyl;

R$^j$, R$^k$, R$^s$, R$^t$, R$^u$, and R$^v$, at each occurrence, are each independently hydrogen, halogen, alkyl, or haloalkyl; and p, q, and w, at each occurrence, are each independently 1, 2, 3, or 4.

Another aspect of the inventions relates to a pharmaceutical composition comprising one or more compounds of the invention or a pharmaceutically acceptable salt or solvate thereof, and one or more pharmaceutically acceptable carriers, alone or co-administered with acetaminophen, or with one or more nonsteroidal anti-inflammatory drug (NSAID), or a combination thereof.

Yet other aspect provides methods for treating diseases or disorders as defined herein below. Said methods comprise the step of administering therapeutically effective amount of one or more of the compound of the invention, or a pharmaceutically acceptable salt or solvate thereof, to a subject in need thereof, optionally with one or more pharmaceutically acceptable carrier, and alone or in combination with one or more nonsteroidal anti-inflammatory drug (SAID), or with acetaminophen, or a combination thereof.

Further aspect of the invention provides the use of a compound of the invention, or a pharmaceutically acceptable salt or solvate thereof, in the manufacture of a medicament for the treatment of disease or disorders as defined herein below, alone or in combination with acetaminophen, or with one or more nonsteroidal anti-inflammatory drug (NSAID), or with a combination of acetaminophen and NSAID; and alone or in combination with one or more pharmaceutically acceptable salt thereof.

It is to be understood that both the foregoing general description and the following detailed description are exemplary, but are not restrictive, of the invention.

DETAILED DESCRIPTION

Compounds of formula (I) are disclosed in this invention,

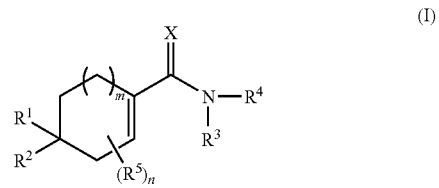

(I)

wherein R$^1$, R$^2$, R$^3$, R$^4$, R$^5$, X, m, and n are defined above in the Summary of the Invention and below in the Detailed Description. Compositions comprising such compounds and methods for treating conditions and disorders using such compounds and compositions are also disclosed.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. Definition

As used in the specification and the appended claims, unless specified to the contrary, the following terms have the meaning indicated:

The term "alkenyl" as used herein, means a straight or branched chain hydrocarbon containing from 2 to 10 carbons and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkyl" as used herein, means a saturated, straight or branched hydrocarbon chain containing from 1 to 10 carbon atoms. The term "C$_{1-6}$ alkyl" as used herein, means a saturated, straight or branched hydrocarbon chain containing from 1 to 6 carbon atoms. The term "C$_{1-3}$ alkyl" as used herein, means a saturated, straight or branched hydrocarbon chain containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 3-methylhexyl, 2,2-dimethylpentyl, 2,3-dimethylpentyl, n-heptyl, n-octyl, n-nonyl, and n-decyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkylene" means a divalent group derived from a saturated, straight or branched chain hydrocarbon of from 1 to 10 carbon atoms. Representative examples of alkylene include, but are not limited to, —CH$_2$—, —CH(CH$_3$)—, —CH(C$_2$H$_5$), —CH(CH(CH$_3$)(C$_2$H$_5$))—, —C(H)(CH$_3$)CH$_2$CH$_2$—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 1,1-dimethylprop-2-ynyl, 1-propyl-pent-3-ynyl, 3-butynyl, 2-pentynyl, and 1-butynyl.

The term "amino" as used herein, means NH$_2$, N(H)(alkyl), or N(alkyl)$_2$.

The term "aminoalkyl" as used herein, means an amino group as defined herein, appended to the parent molecular moiety through an alkyl group, as defined herein.

The term "aryl," as used herein, means phenyl, a bicyclic aryl or a tricyclic aryl. The bicyclic aryl is naphthyl, or a phenyl fused to a monocyclic cycloalkyl, or a phenyl fused to a monocyclic cycloalkenyl. Representative examples of the bicyclic aryl include, but are not limited to, dihydroindenyl, indenyl, naphthyl, dihydronaphthalenyl, and tetrahydronaphthalenyl. The tricyclic aryl is exemplified by a bicyclic aryl fused to a monocyclic cycloalkyl, or a bicyclic aryl fused to a monocyclic cycloalkenyl, or a bicyclic aryl fused to a phenyl. Representative examples of tricyclic aryls include, but are not limited to, anthracene, phenanthrene, dihydroanthracenyl, fluorenyl, 1,2-dihydroacenaphthylenyl, and tetrahydrophenanthrenyl. The phenyl, bicyclic, and tricyclic aryls are attached to the parent molecular moiety through any carbon atom contained within the phenyl, bicyclic and tricyclic aryls respectively.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "cycloalkenyl" as used herein, means monocyclic or bicyclic cycloalkenyls containing zero heteroatoms in the ring. The monocyclic cycloalkenyl has three-, four-, five-, six-, seven-, or eight carbon atoms and zero heteroatoms. The three or four-membered ring systems have one double bond, the five- or six-membered ring systems have one or two double bonds, and the seven- or eight-membered ring systems have one, two, or three double bonds. Representative examples of monocyclic cycloalkenyls include, but are not limited to, cyclohexenyl, 2,4-cyclohexadien-1-yl, and 3-cyclopenten-1-yl. Bicyclic cycloalkenyls are exemplified by a monocyclic cycloalkenyl fused to a monocyclic cycloalkyl, or a monocyclic cycloalkenyl fused to a monocyclic cycloalkenyl. Representative examples of bicyclic cycloalkenyls include, but are not limited to 3a, 4, 5, 6, 7,7a-hexahydro-1H-indenyl, 4,5,6,7-tetrahydro-3aH-indene, and octahydronaphthalenyl. The cycloalkenyl groups of the present invention are appended to the parent molecular moiety through any substitutable carbon atom within the groups, and may contain one or two alkylene bridges of 1, 2, 3, or 4 carbon atoms, wherein each bridge links two non-adjacent atoms within the groups.

The term "cycloalkyl" as used herein, means a saturated, monocyclic or bicyclic ring system. The monocyclic cycloalkyl is a carbocyclic ring system containing 3-, 4-, 5-, 6, 7, or 8 carbon atoms and zero heteroatoms as ring atoms, and zero double bonds. Examples of monocyclic cycloalkyls include cyclopropyl, cyclobutyl, cyclopentyl, cyclohexyl, cycloheptyl, and cyclooctyl. Bicyclic cycloalkyls are exemplified by fusion of two monocyclic cycloalkyl rings. Representative examples of bicyclic cycloalkyls include, but are not limited to, bicyclo[4.1.0]heptane, bicyclo[6.1.0]nonane, octahydroindene, and decahydronaphthalene. The monocyclic and the bicyclic cycloalkyl groups of the present invention may contain one or two alkylene bridges of 1, 2, 3, or 4 carbon atoms, wherein each bridge links two non-adjacent atoms within the groups. Examples of such bridged cycloalkyls include, but are not limited to, bicyclo[2.2.1]heptane, bicyclo[3.1.1]heptane, bicyclo[2.2.2]octane, bicyclo[3.3.1]nonane, adamantane (tricyclo[3.3.1.1$^{3,7}$]decane), and noradamantane (octahydro-2,5-methanopentalene). The monocyclic and the bicyclic cycloalkyl groups of the present invention can be appended to the parent molecular moiety through any substitutable carbon atom of the groups.

The term "halo" or "halogen" as used herein, means —Cl, —Br, —I or —F.

The term "haloalkoxy" as used herein, means an alkoxy group, as defined herein, in which one, two, three, four, five, six, or seven hydrogen atoms are replaced by halogen. Representative examples of haloalkoxy include, but are not limited to, fluoromethoxy, 2,2-difluoromethoxy, trifluoromethoxy, and 2-fluoroethoxy.

The term "haloalkyl" as used herein, means an alkyl group, as defined herein, in which one, two, three, four, five, six, or seven hydrogen atoms are replaced by halogen. Representative examples of haloalkyl include, but are not limited to, chloromethyl, 2-fluoroethyl, 2,2-difluoroethyl, trifluoromethyl, 2,2,2-trifluoroethyl, 2,2,2-trifluoro-1,1-dimethylethyl, difluoromethyl, 3,3,3-trifluoropropyl, pentafluoroethyl, 2-chloro-3-fluoropentyl, and 2-iodoethyl.

The term "heteroaryl," as used herein, means a monocyclic heteroaryl or a bicyclic heteroaryl. The monocyclic heteroaryl is a 5- or 6-membered ring containing at least one heteroatom independently selected from the group consisting of O, N, and S. The 5-membered ring contains two double bonds and one, two, three, or four heteroatoms. The 6-membered ring contains three double bonds and one, two, three or four heteroatoms. Representative examples of monocyclic heteroaryls include, but are not limited to, furanyl, imidazolyl, isoxazolyl, isothiazolyl, oxadiazolyl, oxazolyl, pyridinyl (including pyridin-2-yl), pyridazinyl, pyrimidinyl, pyrazinyl, pyrazolyl, pyrrolyl, tetrazolyl, thiadiazolyl, thiazolyl (including 1,3-thiazol-2-yl), thienyl, triazolyl, and triazinyl. The bicyclic heteroaryl is exemplified by a monocyclic heteroaryl fused to phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryls include, but are not limited to, benzofuranyl, benzoxadiazolyl, 1,3-benzothiazolyl, benzimidazolyl, benzodioxolyl, benzothienyl, chromenyl, cinnolinyl, furopyridine, indolyl, indazolyl, isoindolyl, isoquinolinyl, naphthyridinyl, oxazolopyridine, quinolinyl, thienopyridine, and thienopyridinyl. The monocyclic and the bicyclic heteroaryl groups are connected to the parent molecular moiety through any substitutable carbon atom or any substitutable nitrogen atom contained within the groups. The nitrogen and sulfur heteroatoms of the heteroaryl rings may optionally be oxidized, and are contemplated within the scope of the invention.

The term "heterocycle" or "heterocyclic" as used herein, means a monocyclic or a bicyclic ring system containing at least one heteroatom. The monocyclic heterocycle is a 3-, 4-, 5-, 6-, 7-, or 8-membered ring containing at least one heteroatom in the ring independently selected from the group consisting of O, N, and S. The 3- or 4-membered ring contains one heteroatom in the ring selected from the group consisting of O, N and S, and optionally one double bond. The 5-membered ring contains zero or one double bond, and one, two, or three heteroatoms in the ring independently selected from the group consisting of O, N and S. The 6-, 7-, or 8-membered ring contains zero, one, or two double bonds, and one, two, or three heteroatoms in the ring independently selected from the group consisting of O, N and S. Representative examples of monocyclic heterocycles include, but are not limited to, azetidinyl, azepanyl, aziridinyl, diazepanyl, 1,3-dioxanyl, 1,4-dioxanyl, 1,3-dioxolanyl, 4,5-dihydroisoxazol-5-yl, 3,4-dihydropyran-6-yl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle of the present invention is exemplified by a monocyclic heterocycle fused to a phenyl group, or a monocyclic heterocycle fused to a monocyclic cycloalkylgroup, or a monocyclic heterocycle fused to a monocyclic cycloalkenyl group, or a monocyclic heterocycle fused to a monocyclic heterocycle group. Representative examples of bicyclic heterocycles include, but are not limited to, 1,3-benzodioxol-4-yl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl. The heterocycle groups are connected to the parent molecular moiety through any substitutable carbon atom or any substitutable nitrogen atom contained within the group. The monocyclic or bicyclic heterocycle groups of the present invention may contain an alkenylene bridge of 2, 3, or 4 carbon atoms, or one or two alkylene bridges of 1, 2, 3, or 4 carbon atoms, wherein each bridge links two non-adjacent carbon atoms within the groups. Examples of such bridged heterocycles include, but are not limited to, oxaadamantane (2-oxatricyclo [3.3.1.1$^{3,7}$]decane), octahydro-2,5-epoxypentalene, hexahydro-2H-2,5-methanocyclopenta[b]furan, hexahydro-1H-1,4-methanocyclopenta[c]furan, oxabicyclo[2.2.1]heptane and 2,4-dioxabicyclo[4.2.1]nonane. The nitrogen and sulfur heteroatoms in the heterocycle rings may optionally be oxidized and the nitrogen atoms may optionally be quarternized.

The term "hydroxyalkyl" as used herein, means an alkyl group, as defined herein, wherein one, two, or three hydrogen atoms are replaced by OH. Representative examples of hydroxyalkyl include, but are not limited to, hydroxymethyl, 2-hydroxyethyl, 3-hydroxypropyl, and 2-ethyl-4-hydroxyheptyl.

The term "oxo" as used herein, means =O.

b) Compounds

Compounds of the invention have the formula (I) as described above.

Particular values of variable groups in compounds of formula (I) are as follows. Such values may be used where appropriate with any of the other values, definitions, claims or embodiments defined hereinbefore or hereinafter.

In compounds of formula (I), R$^2$ has values as described generally in the Summary.

R$^2$, for example, is halogen (e.g. F), alkyl (e.g. C$_{1-3}$ alkyl such as, but not limited to, methyl), haloalkyl (e.g. trifluoromethyl), —CN, —O(alkyl) (e.g., —OCH$_3$), —O(haloalkyl), or —OH.

One embodiment of the invention provides compounds of formula (I) wherein R$^2$ is alkyl (e.g. C$_{1-3}$ alkyl such as, but not limited to, methyl) or halogen. For example, R$^2$ is C$_{1-3}$ alkyl (e.g. methyl), chlorine, or fluorine.

Other embodiment of the invention provides compounds of formula (I) wherein R$^2$ is —OH.

Yet other embodiment of the invention provides compounds of formula (I) wherein R$^2$ is —O(alkyl). For example, R$^2$ is —OCH$_3$.

Another embodiment of the invention provides compounds of formula (I) wherein R$^2$ is haloalkyl. For example, R$^2$ is CF$_3$.

Yet other embodiment of the invention provides compounds of formula (I) wherein R$^2$ is —CN.

In certain embodiments, R$^2$ and the adjacent carbon atom, together with the carbon atom to which R$^2$ is attached, form a 3-6 membered monocyclic cycloalkyl ring that is optionally substituted as described in the Summary. Thus, contemplated in the invention are also compounds of formula (II)

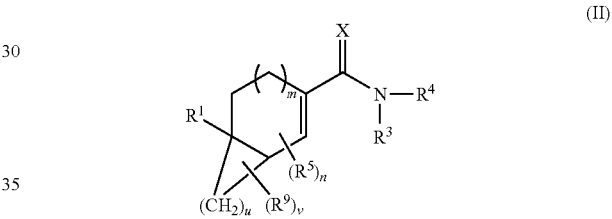

(II)

wherein u is 1, 2, 3, or 4; v is 0, 1, 2, 3, or 4; R$^9$ is alkyl, hydroxyalkyl, alkoxyalkyl, haloalkoxyalkyl, haloalkyl, arylalkyl, aryl, aminoalkyl, amino, and halogen, wherein the aryl and the aryl moiety of the arylalkyl are each independently unsubstituted or substituted with 1, 2, 3, 4, or 5 substituents selected from the group consisting of alkyl, alkenyl, alkynyl, halogen, OH, O(alkyl), O(haloalkyl), amino, and haloalkyl; and R$^1$, R$^3$, R$^4$, R$^5$, X, m, and n are as described generally in the Summary.

In compounds of formula (I) or (II), R$^1$ is phenyl or a monocyclic heteroaryl (for example, pyridinyl or thiazolyl), each of which is optionally substituted with 1, 2, 3, 4, or 5 substituents as represented by R$^6$ groups. One embodiment of the invention provides compounds of formula (I) or (II) wherein R$^1$ is pyridinyl, optionally substituted as described in the Summary, for example, optionally substituted with one or two R$^6$ groups. Another embodiment of the invention provides compounds of formula (I) wherein R$^1$ is formula (I). A further embodiment of the invention provides compounds of formula (I) or (II) wherein R$^1$ is formula (ii).

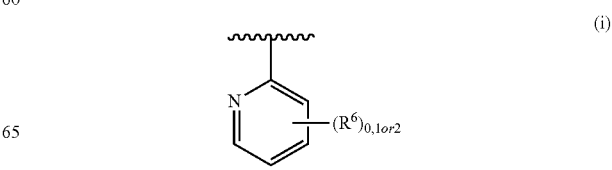

(i)

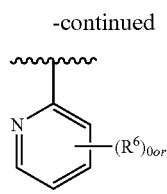

Yet another embodiment of the invention relates to compounds of formula (I) or (II) wherein $R^1$ is phenyl, optionally substituted as described in the Summary, for example, optionally substituted with one or two $R^6$ groups. For example, $R^1$ is formula (iii). Other example of $R^1$ is formula (iv).

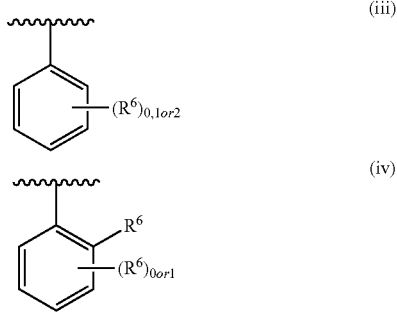

In certain embodiment, the optional $R^6$ group of formula (ii) or (iv) is located at the 4-position relative to the carbon atom that is attached to the cycloalkene ring of the parent molecular moiety.

$R^6$ in the embodiments described herein above has meanings as described in the Summary section. Certain embodiments of the invention relate to compounds of formula (I) or (II) wherein $R^6$ is, for example, halogen (e.g. F, Cl), alkyl (e.g. $C_{1-6}$ alkyl such as, but not limited to, methyl), haloalkyl (e.g. trifluoromethyl), or $N(R^d)(R^f)$ wherein $R^d$ and $R^f$ are as described in the Summary. For example, $R^d$ and $R^f$ are each independently hydrogen or $C_{1-6}$ alkyl such as, but not limited to, methyl. Further examples of $R^6$ include, but are not limited to, chlorine, fluorine, methyl, trifluoromethyl, and $N(C_{1-6}$ alkyl$)_2$.

$R^3$ has values as described generally in the Summary. For example, in compounds of formula (I) or (II), $R^3$ is hydrogen or $C_{1-6}$ alkyl. One embodiment of the invention provides compounds wherein $R^3$ is hydrogen.

$R^4$ is aryl, heteroaryl, cycloalkyl, cycloalkenyl, or heterocycle, wherein each $R^4$ is optionally substituted with 1, 2, 3, 4, 5, or 6 substituents as represented by $R^7$, and $R^7$ is as described in the Summary section.

One embodiment of the invention provides compounds of formula (I) or (II) wherein $R^4$ is optionally substituted phenyl.

Another embodiment of the invention provides compounds of formula (I) or (II) wherein $R^4$ is optionally substituted heteroaryl.

Yet another embodiment of the invention provides compounds of formula (I) or (II) wherein $R^4$ is optionally substituted monocyclic heteroaryl (e.g. pyridinyl).

Further, other embodiment of the invention provides compounds wherein $R^4$ is phenyl or monocyclic heteroaryl, and each $R^4$ is optionally substituted as disclosed in the Summary and in embodiments described herein.

In certain embodiments, $R^4$ is optionally substituted with one or two $R^7$ groups.

In certain embodiments, $R^4$ is substituted with one or two $R^7$ groups, and that at least one of the $R^7$ groups is attached to the 4-position of the phenyl or the monocyclic heteroaryl ring relative to the carbon atom that is attached to the nitrogen atom of the parent molecular moiety.

Examples of $R^7$ include, but are not limited to, alkyl (e.g. $C_{1-6}$ alkyl such as, but not limited to, isopropyl, tert-butyl), halogen (e.g. Cl, F), $-OR^a$, $-SF_5$, $-S(O)_2R^b$, $-N(R^a)(R^c)$, haloalkyl (e.g. trifluoromethyl, 2,2,2-trifluoromethyl-1-methylethyl), and $-(CR^jR^k)_p-CN$, wherein $R^a$, $R^b$, $R^j$, $R^k$, and p are as described in the Summary section. $R^a$ and $R^b$, for example, are each independently alkyl (e.g. methyl) or haloalkyl (e.g. trifluoromethyl). $R^j$ and $R^k$, for example, are each independently hydrogen or $C_{1-6}$ alkyl (e.g. methyl). p, for example, is 1 or 2. In certain embodiments, p is 1. One embodiment of the invention relate to compounds wherein $R^7$ is tert-butyl, isopropyl, chlorine, fluorine, $-O(CF_3)$, $-SF_5$, $-S(O)_2(CF_3)$, $-NH_2$, $-N(H)(CH_3)$, $-N(CH_3)_2$, $-CF_3$, and $-(CR^jR^k)_p-CN$, and $R^j$, $R^k$, and p are as described in the Summary and in embodiments described herein above.

One embodiment of the invention relates to compounds wherein n is 0.

Yet other embodiment of the invention provides compounds of formula (I) or (II) wherein n is 1.

$R^5$ has values as described generally in the Summary.

Certain embodiment of the invention includes, but is not limited to, compounds of formula (I) or (II) wherein $R^5$, if present, is alkyl such as, but not limited to, $C_{1-3}$ alkyl. For example, $R^5$ is methyl.

Certain embodiment of the invention provides compounds of formula (I) or (II) wherein X is O.

Other embodiment of the invention provides compounds of formula (I) or (II) wherein X is S.

Yet another embodiment relates to compounds of formula (I) or (II) wherein X is $N(R^z)$ wherein $R^z$ is hydrogen, alkyl, or CN.

m is 0, 1, or 2. In one embodiment, m is 1. It is to be understood that when m is 1 in formula (I), this refers to compounds of formula (Ia)

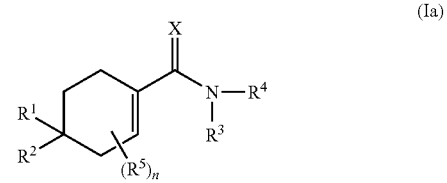

wherein $R^1$, $R^2$, $R^3$, $R^4$, $R^5$, X, and n have the values as set forth in the Summary and the Detailed description sections. Embodiments for $R^1$, $R^2$, $R^3$, $R^4$, $R^5$, X, and n, and combinations of embodiments, including particular, and more particular embodiments as described for formula (I) are also contemplated for compounds of formula (Ia).

It is appreciated that the present invention contemplates compounds of formula (I), (Ia), or (II) with combinations of the above embodiments, including particular, more particular and preferred embodiments.

Accordingly, one aspect of the invention relates to a group of compounds of formula (I) or (II) wherein X is O, and m is 1.

Other examples of a group of compounds of formula (I) or (II) include those wherein X is S, and m is 1.

Other examples of a group of compounds of formula (I) or (II) include those wherein X is $N(R^z)$, and m is 1.

Yet other examples of a group of compounds of formula (I) or (II) include those wherein X is O, and m is 2.

Further examples of a group of compounds of formula (I) or (II) include those wherein X is S, and m is 2.

Another examples of a group of compounds of formula (I) or (II) include those wherein X is N($R^z$), and m is 2.

Yet further examples of a group of compounds of formula (I) or (II) include those wherein X is O, and m is 0.

Yet other examples of a group of compounds of formula (I) or (II) include those wherein X is S, and m is 0.

Yet another examples of a group of compounds of formula (I) or (II) include those wherein X is N($R^z$), and m is 0.

Within each group of compounds of formula (I), (Ia), or (II) as described in the preceding paragraphs, $R^1$, $R^2$, $R^3$, $R^4$, $R^5$, $R^z$, and n have values as defined in the Summary.

Thus, of each group of compounds of formula (I), (Ia), or (II) as described in the preceding paragraphs, examples of a subgroup include those wherein $R^1$ is optionally substituted monocyclic heteroaryl. For example, $R^1$ is pyridinyl or thiazolyl, optionally substituted as described in the Summary. In one embodiment, $R^1$ is substituted pyridinyl, optionally substituted as described in the Summary, for example, optionally substituted with one or two substituents, $R^6$. Other embodiment relates to compounds wherein $R^1$ is formula (i). Yet other embodiment relates to compounds wherein $R^1$ is formula (ii).

Other examples of a subgroup include those wherein $R^1$ is optionally substituted phenyl. For example, $R^1$ is formula (iii). Further example of $R^1$ is formula (iv).

Of all examples of the groups and subgroups of compounds of formula (I), (Ia), or (II) as discussed herein-above, $R^2$, $R^3$, $R^4$, $R^z$, $R^5$, n, and the optional substituents of $R^1$ have the meanings as described in the Summary and the Detailed Description.

For example, for each of the foregoing groups and subgroups of compounds, examples of the optional substituents ($R^6$) of $R^1$ include, but are not limited to, halogen (e.g. F, Cl), alkyl (e.g. $C_{1-6}$ alkyl such as, but not limited to, methyl), haloalkyl (e.g. trifluoromethyl), or N($R^d$)($R^f$) wherein $R^d$ and $R^f$ are as described in the Summary. For example, $R^d$ and $R^f$ are each independently hydrogen or $C_{1-6}$ alkyl such as, but not limited to, methyl. Further examples of $R^6$ include, but are not limited to, chlorine, fluorine, methyl, trifluoromethyl, and N($C_{1-6}$ alkyl)$_2$. $R^4$, for example, is phenyl, optionally substituted as described in the Summary section, for example, optionally substituted with one or two $R^7$. Yet other examples of $R^4$ is phenyl substituted with one or two $R^7$ groups, wherein at least one of the $R^7$ is located at the 4-position of the phenyl ring relative to the carbon atom that is attached to the nitrogen atom of formula (I), (Ia), or (II). Further examples of $R^4$ include, but are not limited to, heteroaryl (e.g. monocyclic heteroaryl such as, but not limited to, pyridinyl), optionally substituted as described in the Summary and in the Detailed Description sections. Certain embodiment of the invention relates to compounds wherein the heteroaryl is optionally substituted with one or two $R^7$ groups. Yet certain embodiment relates to compounds of formula (I), (Ia), or (II) wherein $R^4$ is monocyclic heteroaryl (for example, pyridinyl), substituted with one or two substituents, wherein at least one of the optional substituents, $R^7$, is located on the 4-position of the ring relative to the carbon that is attached to the nitrogen atom of formula (I), (Ia), or (II). Examples of $R^7$ are as described in the Summary and in the Detailed Description sections. Certain embodiment of the invention pertains to compounds wherein $R^5$, if present, is alkyl such as, but not limited to, $C_{1-3}$ alkyl. n, for example, is 1. Yet other embodiment includes compounds of formula (I), (Ia), or (II) wherein n is 0. $R^2$ is, for example, halogen (e.g. F), alkyl (e.g $C_{1-3}$ alkyl such as, but not limited to, methyl), haloalkyl (e.g. trifluoromethyl), —CN, —O(alkyl) (e.g. OCH$_3$), —O(haloalkyl), or —OH. Certain embodiments of the invention include compounds of formula (I) or (Ia) wherein $R^2$ is, for example, halogen (e.g. F) or alkyl (e.g. $C_{1-3}$ alkyl such as, but not limited to, methyl). For example, $R^2$ is $C_{1-3}$ alkyl (e.g. methyl), chlorine, or fluorine. In one embodiment, $R^2$ is halogen such as, but not limited to, fluorine or chlorine. In another embodiment, $R^2$ is —OH. In yet another embodiment, $R^2$ is —O(alkyl) such as, but not limited to, —OCH$_3$. In yet another embodiment, $R^2$ is haloalkyl such as, but not limited to, trifluoromethyl. In yet another embodiment, $R^2$ is —CN. Included in the invention are also compounds of formula (I) or (Ia) wherein $R^2$ and the adjacent carbon atom, together with the carbon atom to which $R^2$ is attached, form a 3-6 membered monocyclic cycloalkyl ring that is optionally substituted as described in the Summary and the Detailed Description sections. $R^3$, for each group and subgroup of compounds of formula (I), (Ia), or (II) as described above is hydrogen or $C_{1-6}$ alkyl. One embodiment of the invention provides compounds of formula (I), (Ia), or (II) wherein $R^3$ is hydrogen.

Yet another aspect of the invention relates to compounds of formula (I) wherein $R^1$ is formula (i), X is O, m is 1, $R^3$ is hydrogen, and $R^4$ is phenyl. Accordingly, one embodiment of the invention provides compounds of formula (III)

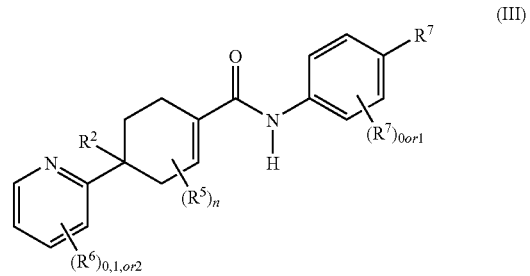

(III)

wherein $R^2$, $R^5$, $R^6$, $R^7$ and n are as disclosed in the Summary and the Detailed Description sections. It is understood that embodiments for $R^2$, $R^5$, $R^6$, $R^7$ and n, and combinations of embodiments, including particular, and more particular embodiments as described for formula (I), (Ia) or (II) are also contemplated for compounds of formula (III).

Compounds of the present invention contain one or more asymmetrically substituted carbon atoms in the cycloalkene ring of formula (I), (Ia), (II) and (III). For example, compounds of formula (I) and (III) can have stereoisomers including, but not limited to, those shown below:

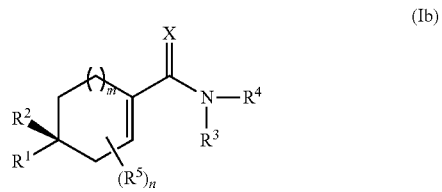

(Ib)

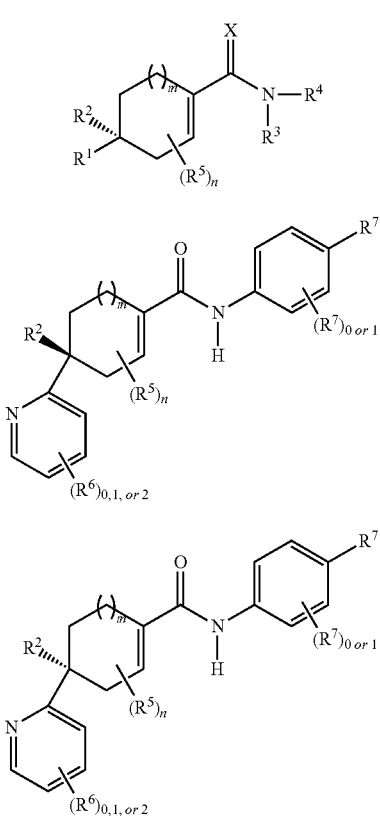

wherein R¹, R², R³, R⁴, R⁵, R⁶, R⁷, X, m, and n are as disclosed in the Summary and the Detailed Description sections. It is understood that embodiments for R¹, R², R³, R⁴, R⁵, R⁶, R⁷, X, m, and n, and combinations of embodiments, including particular, and more particular embodiments as described for formula (I), (Ia) or (II), are also contemplated for compounds of formula (Ib), (Ic), (IIIa), and (IIIb). When n is 1, the carbon atom to which R⁵ group is attached can have (R) or (S) configuration. The terms "R" and "S" used herein are configurations as defined in IUPAC 1974 Recommendations for Section E, Fundamental Stereochemistry, Pure Appl. Chem., 1976, 45: 13-30. The present invention contemplates various individual stereoisomers (including enantiomers and diastereomers) and mixtures thereof. Individual stereoisomers of compounds of the present invention may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

The invention also contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or heterocycle are designated as being of cis or trans configuration.

Within the present invention it is to be understood that compounds disclosed herein may exhibit the phenomenon of tautomerism and all tautomeric isomers are included in the scope of the invention.

Exemplary compounds of the present invention include, but are not limited to, 4-(3-chloropyridin-2-yl)-4-fluoro-N-[4-(trifluoromethyl)phenyl]cyclohex-1-ene-1-carboxamide;
N-(4-chlorophenyl)-4-(3-chloropyridin-2-yl)-4-fluorocyclohex-1-ene-1-carboxamide;
4-(3-chloropyridin-2-yl)-4-fluoro-N-{4-[(trifluoromethyl)sulfonyl]phenyl}cyclohex-1-ene-1-carboxamide;
N-(4-tert-butylphenyl)-4-(3-chloropyridin-2-yl)-4-fluorocyclohex-1-ene-1-carboxamide;
4-(3-chloropyridin-2-yl)-4-fluoro-N-[4-(trifluoromethoxy)phenyl]cyclohex-1-ene-1-carboxamide;
4-(3-chloropyridin-2-yl)-N-[4-(1-cyano-1-methylethyl)phenyl]-4-fluorocyclohex-1-ene-1-carboxamide;
4-(3-chloropyridin-2-yl)-4-methoxy-N-{4-[(trifluoromethyl)sulfonyl]phenyl}cyclohex-1-ene-1-carboxamide;
4-(3-chloropyridin-2-yl)-4-methoxy-N-[4-(trifluoromethyl)phenyl]cyclohex-1-ene-1-carboxamide;
4-fluoro-4-(3-methylpyridin-2-yl)-N-[4-(trifluoromethyl)phenyl]cyclohex-1-ene-1-carboxamide;
4-fluoro-4-(3-methylpyridin-2-yl)-N-[4-(trifluoromethoxy)phenyl]cyclohex-1-ene-1-carboxamide;
4-fluoro-4-(3-methylpyridin-2-yl)-N-{4-[(trifluoromethyl)sulfonyl]phenyl}cyclohex-1-ene-1-carboxamide;
N-(4-chlorophenyl)-4-fluoro-4-(3-methylpyridin-2-yl)cyclohex-1-ene-1-carboxamide;
N-(4-tert-butylphenyl)-4-fluoro-4-(3-methylpyridin-2-yl)cyclohex-1-ene-1-carboxamide;
4-fluoro-4-(3-fluoropyridin-2-yl)-N-[4-(trifluoromethyl)phenyl]cyclohex-1-ene-1-carboxamide;
N-(4-tert-butylphenyl)-4-fluoro-4-(3-fluoropyridin-2-yl)cyclohex-1-ene-1-carboxamide;
4-fluoro-4-(3-fluoropyridin-2-yl)-N-[5-(trifluoromethyl)pyridin-2-yl]cyclohex-1-ene-1-carboxamide;
4-fluoro-4-(3-fluoropyridin-2-yl)-N-{4-[(trifluoromethyl)sulfonyl]phenyl}cyclohex-1-ene-1-carboxamide;
4-fluoro-4-(3-fluoropyridin-2-yl)-N-[4-(pentafluoro-$\lambda^6$-sulfanyl)phenyl]cyclohex-1-ene-1-carboxamide;
4-fluoro-4-(1,3-thiazol-2-yl)-N-[4-(trifluoromethyl)phenyl]cyclohex-1-ene-1-carboxamide;
4-fluoro-4-(1,3-thiazol-2-yl)-N-{4-[(trifluoromethyl)sulfonyl]phenyl}cyclohex-1-ene-1-carboxamide;
(4R)—N-(4-chlorophenyl)-4-(3-chloropyridin-2-yl)-4-fluorocyclohex-1-ene-1-carboxamide;
(4S)—N-(4-chlorophenyl)-4-(3-chloropyridin-2-yl)-4-fluorocyclohex-1-ene-1-carboxamide;
(4R)-4-(3-chloropyridin-2-yl)-4-fluoro-N-[4-(trifluoromethyl)phenyl]cyclohex-1-ene-1-carboxamide;
(4S)-4-(3-chloropyridin-2-yl)-4-fluoro-N-[4-(trifluoromethyl)phenyl]cyclohex-1-ene-1-carboxamide;
4-[3-(dimethylamino)pyridin-2-yl]-4-(trifluoromethyl)-N-[4-(trifluoromethyl)phenyl]cyclohex-1-ene-1-carboxamide;
4-fluoro-4-(1,3-thiazol-2-yl)-N-{4-[(trifluoromethyl)sulfonyl]phenyl}cyclohex-1-ene-1-carboxamide;
(4R)-4-(3-chloropyridin-2-yl)-4-fluoro-N-{4-[(trifluoromethyl)sulfonyl]phenyl}cyclohex-1-ene-1-carboxamide;
(4S)-4-(3-chloropyridin-2-yl)-4-fluoro-N-{4-[(trifluoromethyl)sulfonyl]phenyl}cyclohex-1-ene-1-carboxamide;
N-{4-[(difluoromethyl)sulfonyl]phenyl}-4-fluoro-4-(3-fluoropyridin-2-yl)cyclohex-1-ene-1-carboxamide;

4-(3-chloropyridin-2-yl)-4-fluoro-N-[4-(pentafluoro-$\lambda^6$-sulfanyl)phenyl]cyclohex-1-ene-1-carboxamide;

4-(3-chloropyridin-2-yl)-4-fluoro-6-methyl-N-[4-(trifluoromethyl)phenyl]cyclohex-1-ene-1-carboxamide;

4-(3-chloropyridin-2-yl)-4-(trifluoromethyl)-N-[4-(trifluoromethyl)phenyl]cyclohex-1-ene-1-carboxamide;

4-(3-chloropyridin-2-yl)-4-fluoro-N-(4-isopropylphenyl)cyclohex-1-ene-1-carboxamide;

4-(3-chloropyridin-2-yl)-4-fluoro-N-[4-(2,2,2-trifluoro-1-methylethyl)phenyl]cyclohex-1-ene-1-carboxamide;

6-[3-(trifluoromethyl)pyridin-2-yl]-N-{4-[(trifluoromethyl)sulfonyl]phenyl}bicyclo[4.1.0]hept-3-ene-3-carboxamide;

4-(3-chloropyridin-2-yl)-4-fluoro-6-methyl-N-{4-[(trifluoromethyl)sulfonyl]phenyl}cyclohex-1-ene-1-carboxamide; and 4-(3-chloropyridin-2-yl)-4-methyl-N-[4-(trifluoromethyl)phenyl]cyclohex-1-ene-1-carboxamide;

N-(4-tert-butylphenyl)-4-(3-chloropyridin-2-yl)-4-methylcyclohex-1-ene-1-carboxamide.

c. Biological Data (i) In Vitro Data—Determination of Inhibition Potencies

Dulbecco's modified Eagle medium (D-MEM) (with 4.5 mg/mL glucose) and fetal bovine serum were obtained from Hyclone Laboratories, Inc. (Logan, Utah). Dulbecco's phosphate-buffered saline (D-PBS) (with 1 mg/mL glucose and 3.6 mg/1 Na pyruvate, without phenol red), L-glutamine, hygromycin B, and Lipofectamine® were obtained from Life Technologies (Grand Island, N.Y.). G418 sulfate was obtained from Calbiochem-Novabiochem Corp. (San Diego, Calif.). Capsaicin (8-methyl-N-vanillyl-6-nonenamide) was obtained from Sigma-Aldrich, Co. (St. Louis, Mo.). Fluo-4 AM (N-[4-[6-[(acetyloxy)methoxy]-2,7-difluoro-3-oxo-3H-xanthen-9-yl]-2-[2-[2-[bis[2-[(acetyloxy)methoxy]-2-oxyethyl]amino]-5-methyl phenoxy]ethoxy]phenyl]-N-[2-[(acetyloxy)methoxy]-2-oxyethyl]-glycine, (acetyloxy) methyl ester) was purchased from Molecular Probes (Eugene, Oreg.).

The cDNAs for the human TRPV1 receptor were isolated by reverse transcriptase-polymerase chain reaction (RT-PCR) from human small intestine poly A+RNA supplied by Clontech (Palo Alto, Calif.) using primers designed surrounding the initiation and termination codons identical to the published sequences (Hayes et al. Pain Vol. 88 pages 205-215, 2000). The resulting cDNA PCR products were subcloned into pCIneo mammalian expression vector (Promega) and fully sequenced using fluorescent dye-terminator reagents (Prism, Perkin-Elmer Applied Biosystems Division) and a Perkin-Elmer Applied Biosystems Model 373 DNA sequencer or Model 310 genetic analyzer. Expression plasmids encoding the hTRPV1 cDNA were transfected individually into 1321N1 human astrocytoma cells using Lipofectamine®. Forty-eight hours after transfection, the neomycin-resistant cells were selected with growth medium containing 800 μg/mL Geneticin (Gibco BRL). Surviving individual colonies were isolated and screened for TRPV1 receptor activity. Cells expressing recombinant homomeric TRPV1 receptors were maintained at 37° C. in D-MEM containing 4 mM L-glutamine, 300 μg/mL G418 (Cal-biochem) and 10% fetal bovine serum under a humidified 5% $CO_2$ atmosphere.

The functional activity of compounds at the TRPV1 receptor was determined with a $Ca^{2+}$ influx assay and measurement of intracellular $Ca^{2+}$ levels ($[Ca^{2+}]_i$). All compounds were tested over an 11-point half-log concentration range. Compound solutions were prepared in D-PBS (4× final concentration), and diluted serially across 96-well v-bottom tissue culture plates using a Biomek 2000 robotic automation workstation (Beckman-Coulter, Inc., Fullerton, Calif.). A 0.2 μM solution of the TRPV1 agonist capsaicin was also prepared in D-PBS. The fluorescent $Ca^{2+}$ chelating dye Fluo-4 AM was used as an indicator of the relative levels of $[Ca^{2+}]_i$ in a 96-well format using a Fluorescence Imaging Plate Reader (FLIPR)(Molecular Devices, Sunnyvale, Calif.). Cells were grown to confluency in 96-well black-walled tissue culture plates. Then, prior to the assay, the cells were loaded with 100 μL per well of Fluo-4 AM (2 μM, in D-PBS) for 1-2 hours at 23° C. Washing of the cells was performed to remove extracellular Fluo-4 AM (2×1 mL D-PBS per well), and afterward, the cells were placed in the reading chamber of the FLIPR instrument. 50 μL of the compound solutions were added to the cells at the 10 second time mark of the experimental run. Then, after a 3-minute time delay, 50 μL of the capsaicin solution was added at the, 190 seconds time mark (0.05 μM final concentration) (final volume=200 μL) to challenge the TRPV1 receptor. Time length of the experimental run was 240 seconds. Fluorescence readings were made at 1 to 5 second intervals over the course of the experimental run. The peak increase in relative fluorescence units (minus baseline) was calculated from the 190 seconds time mark to the end of the experimental run, and expressed as a percentage of the 0.05 μM capsaicin (control) response. Curve-fits of the data were solved using a four-parameter logistic Hill equation in GraphPad Prism® (GraphPad Software, Inc., San Diego, Calif.), and $IC_{50}$ values were calculated.

Certain compounds of the invention were tested in the assay described above and are effective TRPV1 antagonists with $IC_{50}$ values from about 10 μM to about 10 nM, for example, from about 1 μM to about 10 nM, and preferably, from about 100 nM to about 10 nM.

(ii) In Vivo Data-Assessment of Osteoarthritic Pain

Unilateral knee joint osteoarthritis was induced in male Sprague Dawley rats by a single intra-articular (i.a.) injection of sodium monoiodoacetate (Sigma, St. Louis, Mo.) (3 mg in 0.05 mL sterile isotonic saline) into the joint cavity using a 26G needle under light (2-4%) isoflurane anesthesia. Following injection, the animals were allowed to recover from the effects of anesthesia (usually 5-10 min) before returning them to their home cages. After approximately 21 days, test compound was administered orally. Grip strength was assessed as a measure of activity-induced pain in osteoarthritic rats one hour after administration of test compound. Measurements of hind limb grip force were conducted by recording the maximum compressive force ($CF_{max}$) exerted on the hind limb strain gauge, in a commercially available grip force measurement system (Columbus Instruments, Columbus, Ohio). During testing, each rat was gently restrained and allowed to grasp the wire mesh frame attached to the strain gauge. The experimenter then moved the animal in a rostral-to-caudal direction until the grip was broken. Each rat was sequentially tested twice at an approximately 2-3 min interval to obtain a raw mean grip force ($CF_{max}$ in gram force units). In order to account for the body weight differences among the rats, this raw mean grip force was converted to a maximum hind limb compressive force for each animal by dividing the $CF_{max}$ by the body weight of the rat in kg [($CF_{max}$ in gram force)/kg body weight]. A group of age matched naïve animals was included in each experiment. Each dose experiment included 6 naïve rats, 6 vehicle-controlled rats and 6 drug-administered rats. The data obtained from various dose groups for the test compound were compared with data from the naïve group. The vehicle control group was assigned a value of 0% whereas the naïve group was assigned a value of 100%. The effects for each dose-group were expressed as % return to normal grip force as found in the naïve group.

Certain compounds of the invention were tested using the general protocol as outlined above and exhibited efficacy in relieving pain. For example, at the concentration of 100 μmol/kg these compounds provided pain relief as measured by 30% to about 80% return to normal grip force for the group of animals that received the drug compared to the vehicle control group.

d. Methods of Using the Compounds

One embodiment of the present invention provides a method for treating a disorder that may be ameliorated by inhibiting vanilloid receptor subtype 1 (TRPV1) receptor in a host mammal in need of such treatment. The method comprises administering a therapeutically effective amount of a compound of formula (I) or a pharmaceutically acceptable salt thereof.

Another embodiment of the present invention provides a method for treating pain in a mammal in need of such treatment. This method comprises administering a therapeutically effective amount of a compound of formula (I) according to claim 1 or a pharmaceutically acceptable salt thereof.

Yet another embodiment of the present invention provides a method of treating ischemia including acute cerebral ischemia, pain including chronic pain, neuropathic pain, nociceptive pain, allodynia, inflammatory pain, inflammatory hyperalgesia, post herpetic neuralgia, neuropathies, neuralgia, diabetic neuropathy, HIV-related neuropathy, nerve injury, rheumatoid arthritic pain, osteoarthritic pain, burns, back pain, visceral pain, cancer pain, dental pain, headache, migraine, carpal tunnel syndrome, fibromyalgia, neuritis, sciatica, pelvic hypersensitivity, pelvic pain, menstrual pain, bladder disease, such as incontinence and bladder overactivity, micturition disorder, renal colic; and cystitis; inflammation such as burns, rheumatoid arthritis and osteoarthritis; neurodegenerative disease such as stroke, post stroke pain and multiple sclerosis; pulmonary disease such as asthma, cough, chronic obstructive pulmonary disease (COPD) and bronchoconstriction; gastrointestinal disease such as gastroesophageal reflux disease (GERD), dysphagia, ulcer, irritable bowel syndrome (IBS), inflammatory bowel disease (IBD), colitis and Crohn's disease; ischemia such as cerebrovascular ischemia; emesis such as cancer chemotherapy-induced emesis, and obesity, in mammals, especially humans. For example, the compounds of the invention are useful for the treatment of pain, particularly nociceptive and inflammatory pain. This method comprises the step of administering a therapeutically effective amount of a compound of formula (I) or a pharmaceutically acceptable salt thereof, to a subject in need thereof.

Compounds of the present invention, including but not limited to those specified in the examples, can be used to treat pain as demonstrated by Nolano, M. et al., Pain 81 (1999) 135; Caterina, M. J. and Julius, D., Annu. Rev. Neurosci. 24, (2001) 487-517; Caterina, M. J. et al., Science 288 (2000) 306-313; Caterina, M. J. et al., Nature 389 (1997) 816-824.

Compounds of the present invention, including but not limited to those specified in the examples, can be used to treat bladder overactivity and/or urinary incontinence as demonstrated by Fowler, C. Urology 55 (2000) 60.

Compounds of the present invention, including but not limited to those specified in the examples, can be used to treat inflammatory thermal hyperalgesia as demonstrated by Davis, J. et al., Nature 405 (2000) 183-187.

Compounds of the invention may be administered alone, or in combination with one or more other compounds of the invention, or in combination (i.e. co-administered) with one or more additional pharmaceutical agents. For example, a compound of formula (I) or a pharmaceutically acceptable salt or solvate thereof, may be administered in combination with acetaminophen, or with one or more nonsteroidal anti-inflammatory drug (NSAID), or combination thereof. Examples of the nonsteroidal anti-inflammatory drug (NSAID) include, but are not limited to, aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. Combination therapy includes administration of a single pharmaceutical dosage formulation containing one or more of the compounds of invention and one or more additional pharmaceutical agents, as well as administration of the compounds of the invention and each additional pharmaceutical agent, in its own separate pharmaceutical dosage formulation. For example, a compound of the invention and one or more additional pharmaceutical agents, may be administered to the patient together, in a single oral dosage composition having a fixed ratio of each active ingredient, such as a tablet or capsule; or each agent may be administered in separate oral dosage formulations.

Where separate dosage formulations are used, compounds of the invention and one or more additional pharmaceutical agents may be administered at essentially the same time (e.g. concurrently) or at separately staggered times (e.g. sequentially).

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the invention can also be administered as a pharmaceutical composition comprising the compounds of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention may be administered to a human or a lower animal ranging from about 0.10 µg/kg body weight to about 40 mg/kg body weight. More preferable doses can be in the range of from about 0.10 µg/kg body weight to about 5 mg/kg body weight. If desired, the effective daily dose can be divided into multiple doses for purposes of administration. Consequently, single dose compositions may contain such amounts or submultiples thereof to make up the daily dose.

e. Pharmaceutical Compositions

The present invention further provides pharmaceutical compositions that comprise compounds of the present invention or a pharmaceutically acceptable salt or solvate thereof. The pharmaceutical compositions comprise compounds of the present invention that may be formulated together with one or more non-toxic pharmaceutically acceptable carriers.

Another aspect of the present invention is a pharmaceutical composition comprising a compound of the invention, or a pharmaceutically acceptable salt or solvate thereof, and one or more pharmaceutically acceptable carriers, alone or in combination with acetaminophen, or with one or more non-steroidal anti-inflammatory drug (NSAID), or a combination thereof.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The present invention contemplates compounds of the invention formed by synthetic means or formed by in vivo biotransformation of a prodrug.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. General Synthesis

This invention is intended to encompass compounds of the invention when prepared by synthetic processes or by metabolic processes. Preparation of the compounds by metabolic processes includes those occurring in the human or animal body (in vivo) or processes occurring in vitro.

The compounds of the invention may be prepared by a variety of processes well known for the preparation of compounds of this class. For example, the compounds of the invention wherein the groups $R^1$, $R^2$, $R^3$, $R^4$, $R^5$, m, n, and X have the meanings as set forth in the summary section unless otherwise noted, can be synthesized as shown in Schemes 1-7.

As used in the descriptions of the schemes and the examples, certain abbreviations are intended to have the following meanings: EtOAc for ethyl acetate; 9-BBN for 9-borabicylco[3.3.1]nonane, DMF for N,N-dimethylformamide, DMP for Dess-Martin periodinane; DAST for diethylaminosulfur trifluoride; DMSO for dimethyl sulfonamide, LiHMDS for lithium bis(trimethylsilyl)amide; OTf for trifluoromethylsulfonate, TBAF for tetrabutyl ammonium fluoride, and THF for tetrahydrofuran.

Compounds of general formula (I) wherein X is O and m is 1 can be prepared using general procedures as illustrated in Scheme 1.

Ketones of formula (2) when treated with a sodium, potassium, or lithium bis(trimethylsilyl)amide and a triflating agent provide compounds of formula (3). Examples of suitable triflating agent include, but are not limited to, 1,1,1-trifluoro-N-phenyl-N-(trifluoromethylsulfonyl)methanesulfonamide and N-(5-chloro-2-pyridyl)triflimide. The reaction is generally conducted, for example, at a temperature of about −78° C. to about room temperature, in a solvent such as, but not limited to, THF.

Enol triflates of formula (3) can be converted to amides of formula (4) when treated with amines of formula $R^3R^4NH$, in the presence of carbon monoxide, a base and a palladium catalyst such as, but not limited to, [1,1'-bis(diphenylphosphino)ferrocene]dichloropalladium(II). Alternatively, enol triflates of formula (3) can be transformed to amides of formula (4) by treating with $R^3R^4NH$ in the presence of carbon monoxide atmosphere, a base, a palladium catalyst such as palladium (II) acetate, and a ligand such as, but not limited to, 2-dicyclohexylphosphino-2'-(N,N-dimethylamino)biphenyl, 1,3-bis(diphenylphosphino)propane, triphenylphosphine, or 2-dicyclohexylphosphine-2'-(N,N-dimethylamino)biphe- Scheme 1

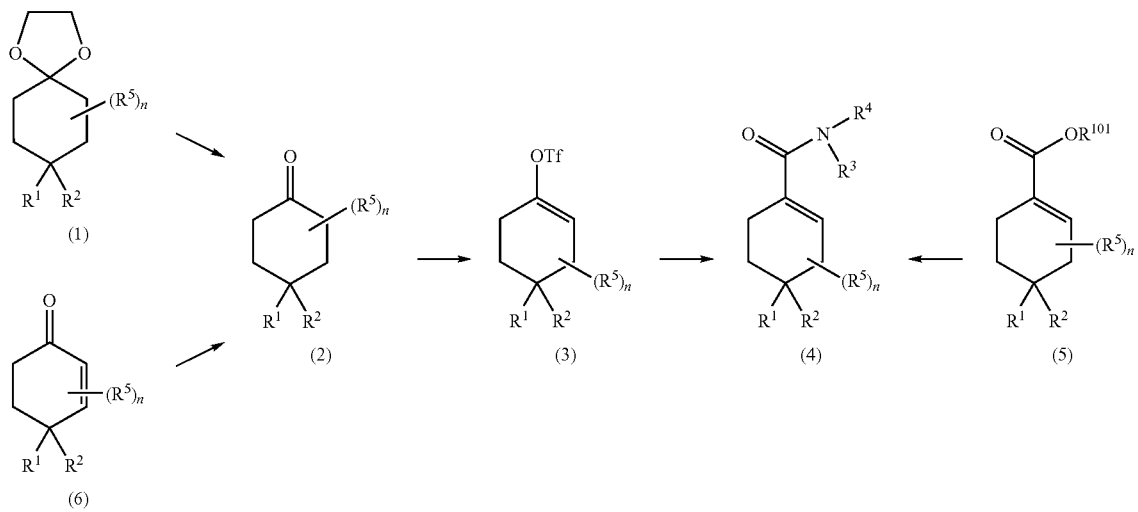

Compounds of formula (4) can be prepared from ketals of formula (1) or from enones of formula (6). For example, compounds of formula (1) can be reacted with an acid to provide ketones of formula (2). Examples of suitable acid for the conversion are inorganic acid such as, but not limited to, trifluoroacetic acid, an inorganic acid such as, but not limited to, hydrochloric acid, or mixtures thereof. The reaction is generally conducted in a solvent such as, but not limited to, dichloromethane, THF, dioxane, or mixtures thereof, at a temperature of about room temperature to about 60° C. Alternatively, ketones of formula (2) can be obtained from the selective reduction of enones (6) by hydrogenation in the presence of a catalyst such as 5% platinum/carbon. The reaction is generally conducted in a solvent such as, but not limited to, tetrahydrofuran, at about room temperature. Enones of formula (6) can also be converted to ketone of formula (2) via a two-step process wherein the enone is first reduced to a substituted cycloalkane alcohol, followed by oxidation of the hydroxy functionality to the corresponding ketone. The reduction and oxidation reactions are well known in the art.

nyl). Examples of bases that are suitable for the conversion include, but are not limited to, an organic base such as triethylamine, or an inorganic base such as cesium carbonate. The reaction is generally conducted at a temperature of about room temperature to about 100° C., in a solvent such as, but not limited to, DMF, THF, dioxane, or mixtures thereof. Alternatively, compounds of formula (4) can be synthesized from esters of formula (5) wherein $R^{101}$ is alkyl (prepared in turn from enol triflates of formula (3) by treatment with carbon monoxide and alcohols of formula $R^{101}OH$, in the presence of a base, a palladium catalyst and a ligand). The esters (5) can be transformed to compounds of formula (4) using trimethylaluminum and amines of formula $R^3R^4NH$ in a solvent such as, but not limited to, toluene or dichloromethane. Single enantiomers of formula (4) can be separated by chiral HPLC using a chiral column such as, but not limited to, Chiralcel OD or Chiralcel AS column (chiral Technologies Inc., West Chester, Pa.).

Compounds of formula (1) wherein $R^2$ is —OH, —O(alkyl), —O(haloalkyl), fluorine or chlorine, can be synthesized using general procedures such as those depicted in Scheme 2.

Scheme 2

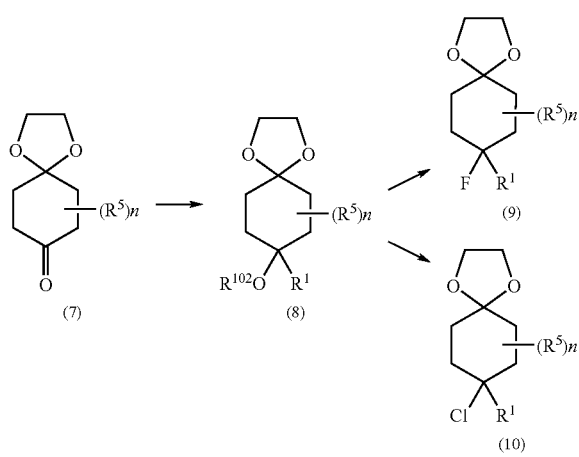

Ketones (7) can be treated with a base such as n-butyllithium and compounds of formula $R^1R^{103}$ wherein $R^{103}$ is halides (for example, bromide) or OTf, to provide compounds of formula (8) wherein $R^{102}$ is hydrogen. The conversion can be accomplished in a solvent such as, but not limited to, diethyl ether at a temperature from about −70° C. to about room temperature. Alkylation of compounds of formula (8) wherein $R^{102}$ is hydrogen using conventional alkylating reagent and conditions known to one skilled in the art, provides compounds of formula (8) wherein $R^{102}$ is alkyl or haloalkyl. For example, compounds (8) wherein $R^{102}$ is hydrogen can be treated with a base such as, but not limited to, sodium hydride, and an alkylating reagent such as alkyl halide (for example, methyl iodide), to provide compounds (8) wherein $R^{102}$ is alkyl. The reaction is generally conducted at a temperature of about 25° C., in a solvent such as, but not limited to, THF. Compounds (8) wherein $R^{102}$ is hydrogen can be treated either with diethylaminosulfur trifluoride (DAST) or thionyl chloride to provide intermediates (9) or (10) respectively.

Ketones of formula (7) wherein n is 0 is commercially available. Ketones (7) wherein n is 1 and $R^5$ is alkyl can be prepared using general procedures such as that shown in Scheme 3.

Scheme 3

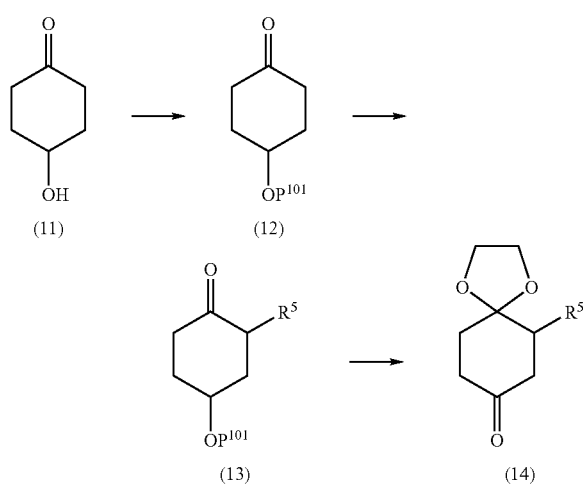

Commercially available 4-hydroxycylohexanone (11) can be protected by treatment with trialkylsilyl halide such as, but not limited to, tert-butyldimethylsilyl chloride to provide intermediates of formula (12) wherein $P^{101}$ is trialkylsilyl group. Deprotanation of the ketones of formula (12) with a base such as, but not limited to, lithium bis(trimethylsilyl)amide or sodium hydride, followed by treatment with an alkylating reagent such as alkyl halides (for example, methyl iodide) using reaction conditions as described in Scheme 2, provides ketones (13). Protection of the carbonyl functionality followed by the deprotection of the hydroxy functionality, and oxidation of the hydroxy converts (13) to (14). The protection, de-protection and oxidation reactions for the conversion of (13) to (14) are well documented in the literature.

Intermediates of formula (6) wherein $R^2$ is haloalkyl or —CN can be prepared using general procedures known to one skilled in the art such as those shown in Scheme 4.

Scheme 4

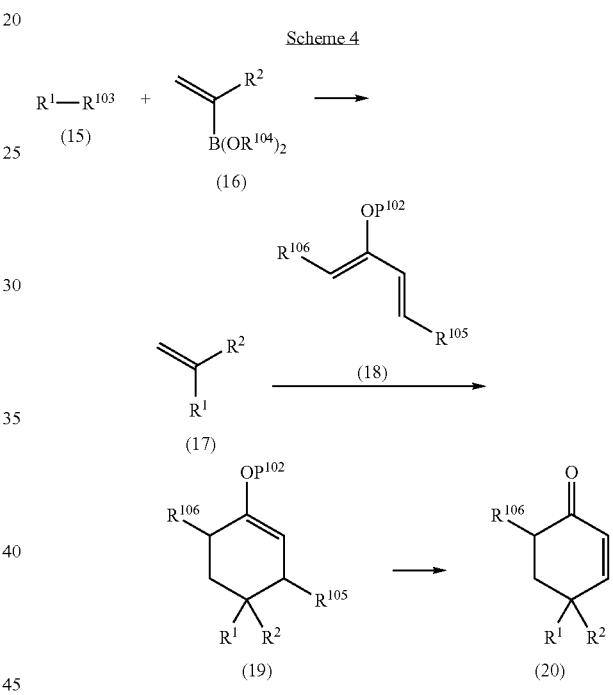

Compounds of formula (15) wherein $R^{103}$ is halides (for example, bromide) or OTf, can be treated with boronic esters of formula (16) wherein $R^2$ is haloalkyl or —CN, and each $R^{104}$ is independently alkyl, to provide compounds of formula (17) using palladium catalyzed coupling reaction conditions known in the literature. For example, the reaction can be carried out in the presence of a palladium catalyst such as tetrakis(triphenylphosphine)palladium(0) and a base such as potassium or cesium carbonate, in a solvent such as, but not limited to, 1,2-dimethoxyethane, water, or mixtures thereof, and at a temperature of about room temperature to about 150° C. Treatment of compounds of formula (17) with dienes of formula (18) wherein $P^{102}$ is a hydroxy protecting group, $R^{105}$ is $N(alkyl)_2$ or O(alkyl), and $R^{106}$ is hydrogen or alkyl, in a solvent such as, but not limited to, aromatic hydrocarbon such as toluene, at a temperature of about room temperature to about the reflux temperature of the solvent employed, provides cyclohexenes of formula (19). Hydroxy protecting groups are well known in the art. Examples of suitable hydroxy protecting groups include, but are not limited to, trialkylsilyl group such as, tert-butyldimethyl silyl. Treatment of (19) with acid such as hydrochloric acid in a solvent such as, but not limited to, tetrahydrofuran, provides compounds of formula (20).

Enones (6) wherein $R^2$ is methyl, haloalkyl or —CN can be prepared using general procedures known to one skilled in the art, such as those shown in Scheme 5.

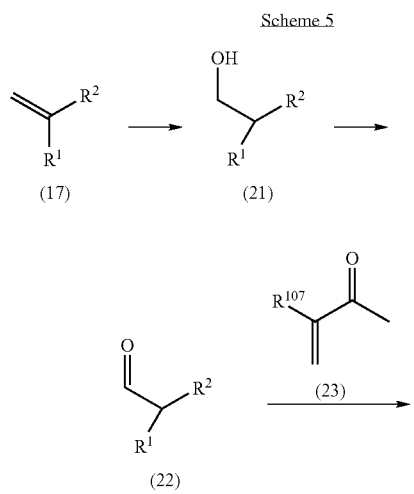

Hydroboration of compounds of formula (17) using reaction conditions known in the art, for example, by treatment with 9-BBN, followed by treatment with an oxidizing reagent provides hydroxy intermediates of formula (21). Suitable oxidizing reagent includes, but is not limited to, hydrogen peroxide. Oxidation of (21) provides aldehydes (22). For example, (21) can be subjected to Swern oxidative conditions to provide aldehydes (22). Aldol condensation of (22) with α, β unsaturated ketones (23) wherein $R^{107}$ is hydrogen or alkyl provides enones of formula (24). For example, (22) and (23) can be reacted in the presence of a base such as, but not limited to, an inorganic base such as potassium hydroxide.

Scheme 6 shows an exemplary synthetic method for the preparation of ketones of formula (2) wherein n is 1 and $R^5$ is alkyl.

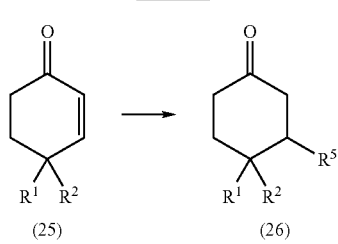

1,4-conjugate addition of alkyl nucleophiles to enones (25) provides substituted ketones of formula (26) wherein $R^5$ is alkyl. For example, treatment of (25) with an alkyl nucleophile such as, but not limited to, an alkyl Grignard reagent (for example, methyl Grignard), optionally in the presence of copper(I) iodide, using reaction conditions that are known in the art, leads to (26).

Compounds of general formula (I) wherein X is S can be made, for example, as shown in Scheme 7.

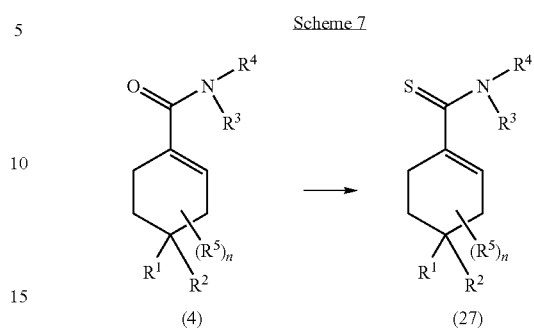

For example, treatment of (4) with Lawesson's reagent (2,4-bis(4-methoxyphenyl)-1,3-dithia-2,4-diphosphetane-2,4-disulfide) according to procedures described in Chem. Lett. 8, (1955) 713-4 or Chem. Lett. 12, (2000) 1398-9, provides compounds of formula (27).

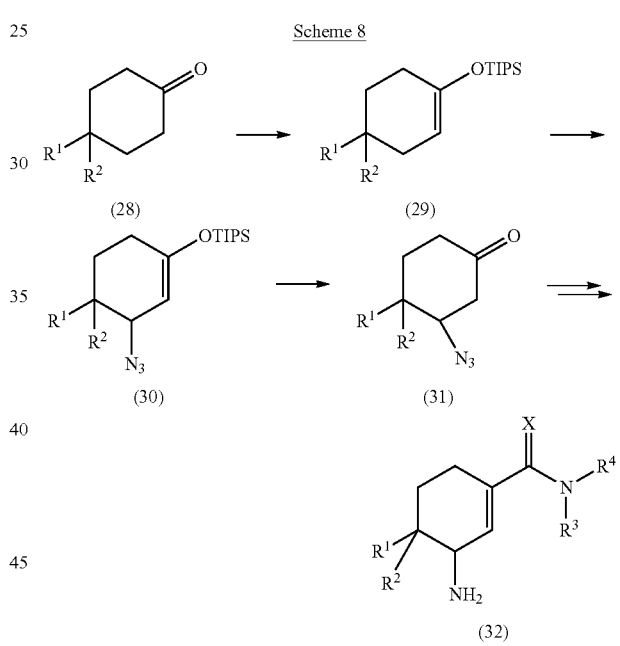

Compounds of formula (I) wherein n is 1 and $R^5$ is $NH_2$, N(H)(alkyl), or N(alkyl)$_2$ can be prepared utilizing general procedures as outlined in Scheme 8.

For example, ketones of formula (28) when treated with a base such as sodium, potassium, or lithium bis(trimethylsilyl) amide and triisopropylsilyl chloride provide triisopropylsilyl (TIPS) enol ethers (29). Treatment of triisopropylsilyl (TIPS) enol ethers (29) with iodosyl benzene in the presence of trimethylsilyl azide produces β-azido adduct (30). Ketones of formula (31) can be derived from treatment of (30) with acids such as hydrochloric acid. Manipulation of intermediates (31) using reaction conditions as described in Schemes 1 and 5, followed by reduction of the azide with lithium aluminum hydride give the amine (32). The amino group in compounds of formula (32) can be mono or di-alkylated using reaction conditions known to one skilled in the art.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Synthetic Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis (3$^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

Following Examples may be used for illustrative purposes and should not be deemed to narrow the scope of the invention.

g) EXAMPLES

Example 1

4-(3-chloropyridin-2-yl)-4-fluoro-N-[4-(trifluoromethyl)phenyl]cyclohex-1-ene-1-carboxamide Example 1A 8-(3-chloropyridin-2-yl)-1,4-dioxaspiro[4.5]decan-8-ol To a −60° C. solution of n-butyl lithium (23 mL, 2.5M in hexane, 58.2 mmol) in diethyl ether (40 mL) was added a solution of 2-bromo-3-chloropyridine (Alfa, 8.0 g, 41.6 mmol) in diethyl ether (60 mL) over 15 minutes. The reaction mixture was stirred for 40 minutes followed by a slow addition (about 15 minutes) of a solution of 1,4-dioxaspiro[4.5]decan-8-one (Aldrich, 8.44 g, 54.0 mmol) in diethyl ether (100 mL), and stirred until reaction mixture warmed up to ambient temperature (about 3 hours). The mixture was quenched with saturated $NH_4Cl$, diluted with ethyl acetate and washed with water. The organic layer was separated, concentrated and the residue crystallized from ethyl acetate-hexanes to obtain 5.5 g of the title compound. Two more crystallizations of the mother liquors yielded 1.61 g more material. Total yield 7.13 g (64%). $^1$H NMR (300 MHz, DMSO-$d_6$) δ ppm 1.59 (d, J=12.69 Hz, 2H), 1.80 (d, J=12.69 Hz, 2H), 1.94 (td, J=12.69, 4.36 Hz, 2H), 2.30-2.41 (m, 2H), 3.88 (s, 4H), 5.36 (s, 1H), 7.36 (dd, J=7.93, 4.76 Hz, 1H), 7.88 (dd, J=7.93, 1.59 Hz, 1H), 8.48 (dd, J=4.76, 1.59 Hz, 1H). MS (DCI) m/z 270.10 $(M+H)^+$.

Example 1B 3-chloro-2-(8-fluoro-1,4-dioxaspiro[4.5]dec-8-yl)pyridine

To a −78° C. solution of the product of Example 1A (7.13 g, 26.4 mmol) in $CH_2Cl_2$ (120 mL) was added diethylaminosulfur trifluoride (DAST, 6.0 g, 4.89 mL, 37.0 mmol). The reaction mixture was allowed to warm to ambient temperature, quenched with water, diluted with ethyl acetate, and washed with water. The organic layer was separated and concentrated. The resulting residue was chromatographed on silica gel, eluting with 0%-30% ethyl acetate-hexane to obtain the title compound (3.0 g, 42%). $^1$H NMR (300 MHz, DMSO-$d_6$) δ ppm 1.69-1.77 (m, 2H), 1.86 (td, J=12.89, 4.75 Hz, 2H), 2.15-2.40 (m, 4H), 3.91 (s, 4H), 7.44 (ddd, J=8.14, 4.75, 0.68 Hz, 1H), 7.96 (dd, J=7.97, 1.53 Hz, 1H), 8.52 (dt, J=4.75, 1.19 Hz, 1H). MS (DCI) m/z 272.05 $(M+H)^+$.

Example 1C 4-(3-chloropyridin-2-yl)-4-fluorocyclohexanone

To a solution of the product of Example 1B (3.0 g, 11.04 mmol) in dioxane (50 mL) was added 3M HCl (50 mL). The reaction mixture was stirred overnight at ambient temperature, quenched with 3M NaOH (50 mL) and extracted with ethyl acetate. The organic layer was separated and concentrated. The resulting residue was chromatographed on silica gel eluting with 0%-30% ethyl acetate-hexane to obtain 95% pure desired product (2.6 g, 103%) as a white solid. $^1$H NMR (300 MHz, DMSO-$d_6$) δ PPM 2.29-2.37 (M, 2H), 2.54-2.75

(M, 6H), 7.48 (DDD, J=8.14, 4.75, 1.02 HZ, 1H), 8.01 (DD, J=8.14, 1.70 HZ, 1H), 8.54 (D, J=4.75 HZ, 1H). MS (DCI) M/Z 228.01 (M+H)⁺.

Example 1D 4-(3-chloropyridin-2-yl)-4-fluorocyclohex-1-en-1-yl trifluoromethanesulfonate To a −78° C. solution of the product of Example 1C (3.0 g, 13.18 mmol) and 1,1,1-trifluoro-N-phenyl-N-(trifluoromethylsulfonyl)methanesulfonamide (5.18 g, 14.50 mmol) in tetrahydrofuran (100 mL) was added lithium bis(trimethylsilyl) amide (1M in tetrahydrofuran, 14.5 mL, 14.50 mmol) over 5 minutes. The reaction mixture was stirred for 1.5 hours at −78° C. and then another 1.5 hours at ambient temperature, quenched with 1N NaOH (200 mL), and extracted with ethyl acetate. The organic phase was washed with water. Organic layer was separated and concentrated. The residue was chromatographed on silica gel eluting with 0%-30% ethyl acetate-hexane to obtain the title compound (4.1 g, 86%) as 92-94% pure viscous oil. ¹H NMR (300 MHz, CDCl₃) δ ppm 2.37-2.61 (m, 3H), 2.71-2.84 (m, 1H), 2.88-3.01 (m, 1H), 3.06-3.26 (m, 1H), 5.77-5.80 (m, 1H), 7.24 (ddd, J=8.14, 4.75, 0.68 Hz, 1H), 7.75 (dd, J=7.97, 1.52 Hz, 1H), 8.44 (d, J=4.75 Hz, 1H). MS (DCI) m/z 360.05 (M+H)⁺.

Example 1E 4-(3-chloropyridin-2-yl)-4-fluoro-N-[4-(trifluoromethyl)phenyl]cyclohex-1-ene-1-carboxamide A mixture of the product of Example 1D (1.590 g, 4.42 mmol), 4-(trifluoromethyl)aniline (1.424 g, 8.84 mmol), and triethylamine (1.24 mL, 8.90 mmol) in dimethylformamide (30 mL) was added to palladium(II) acetate (49.3 mg, 0.220 mmol) and 2-dicyclohexylphospino-2'-(dimethylamino)biphenyl (174.7 mg, 0.444 mmol) in a 250 mL pressure bottle under argon. The mixture was pressurized with carbon monoxide (60 psi), stirred 14 hours at ambient temperature, treated with ethyl acetate (200 mL), washed with saturated sodium bicarbonate (200 mL), brine, dried with anhydrous sodium sulfate, filtered, and concentrated. The residue was chromatographed on silica gel, eluting with 0-to-40% ethyl acetate in hexanes, and concentrated to a yellow oil. Repeated chromatography on silica gel, eluting with dichloromethane, then 30% ethyl acetate in dichloromethane afforded 1.424g (81% yield) of the title compound as a light yellow solid. ¹H NMR (300 MHz, DMSO-d₆) δ ppm 2.15-2.36 (m, 1H), 2.89-3.01 (m, 1H), 3.08-3.21 (m, 1H), 6.75 (s, 1H), 7.49 (ddd, J=8.13, 4.56, 0.79 Hz, 1H), 7.68 (d, J=8.33 Hz, 2H), 7.93 (d, J=8.33 Hz, 2H), 8.03 (dd, J=8.13, 1.39 Hz, 1H), 8.56 (d, J=4.76 Hz, 1H), 10.10 (s, 1H). ¹H NMR (300 MHz, CDCl₃) δ ppm 2.26-2.47 (m, 1H), 2.55-2.72 (m, 3H), 2.93-3.05 (m, 1H), 3.15-3.33 (m, 1H), 6.74 (s, 1H), 7.22-7.27 (m, 1H), 7.58-7.61 (m, 3H), 7.71 (d, J=8.47 Hz, 2H), 7.77 (dd, J=8.13, 1.35 Hz, 1H), 8.46 (ddd, J=4.58, 1.52, 0.85 Hz, 1H). MS (ESI) m/z 398.95 (M+H)⁺. Calcd for C₁₉H₁₅ClF₄N₂O: C, 57.23; H 3.79, N 7.02; Found: C 57.11, H 3.49, N, 6.92.

Example 2

N-(4-chlorophenyl)-4-(3-chloropyridin-2-yl)-4-fluorocyclohex-1-ene-1-carboxamide The title compound was prepared using the procedure as described in Example 1E, except for substituting 4-chloroaniline for 4-(trifluoromethyl)aniline. ¹H NMR (300 MHz, DMSO-d₆) δ ppm 2.14-2.36 (m, 1H), 2.86-2.99 (m, 1H), 3.12-3.25 (m, 1H), 6.69 (s, 1H), 7.37 (d, J=8.82 Hz, 2H), 7.48 (ddd, J=8.14, 4.57, 0.85 Hz, 1H), 7.73 (d, J=8.82 Hz, 2H), 8.02 (dd, J=8.14, 1.36 Hz, 1H), 8.55 (d, J=4.40 Hz, 1H), 9.88 (s, 1H). ¹H NMR (300 MHz, MeOH-d₄) δ ppm 2.27-2.64 (m, 4H), 2.86-2.99 (m, 1H), 3.13-3.27 (m, 1H), 6.70 (s, 1H), 7.31 (d, J=9.15 Hz, 2H), 7.36 (ddd, J=8.14, 4.75, 0.68 Hz, 1H), 7.61 (d, J=8.14 Hz, 2H), 7.89 (d, J=8.14 Hz, 1H), 8.47 (d, J=4.74 Hz, 1H). MS (ESI) m/z 364.94 (M+H)⁺. Calcd for C₁₈H₁₅Cl₂FN₂O: C 59.19, H 4.14, N 7.67; Found: C 58.92, H 4.01, N 7.51.

Example 3

4-(3-chloropyridin-2-yl)-4-fluoro-N-{4-[(trifluoromethyl)sulfonyl]phenyl}cyclohex-1-ene-1-carboxamide The title compound was prepared using the procedure as described in Example 1E, except for substituting 4-(trifluoromethylsulfonyl)aniline for 4-(trifluoromethyl)aniline. ¹H NMR (300 MHz, DMSO-d₆) δ ppm 2.15-2.36 (m, 1H), 2.90-3.03 (m, 1H), 3.11-3.22 (m, 1H), 6.82 (s, 1H), 7.49 (dd, J=8.13, 4.56 Hz, 1H), 8.03 (dd, J=8.14, 1.39 Hz, 1H), 8.07 (d, J=9.12 Hz, 2H), 8.15 (d, J=9.52 Hz, 2H), 8.56 (d, J=4.36 Hz, 1H), 10.50 (s, 1H). ¹H NMR (300 MHz, CDCl₃) δ ppm 2.25-2.46 (m, 1H), 2.56-2.73 (m, 3H), 2.94-3.08 (m, 1H), 3.17-3.27 (m, 1H), 6.78 (s, 1H), 7.23-7.28 (m, 1H), 7.76-7.79 (m, 2H), 7.89 (d, J=9.12 Hz, 2H), 8.01 (d, J=8.72 Hz, 2H), 8.46 (d, J=4.36 Hz, 1H). MS (ESI) m/z 462.95 (M+H)⁺. Calcd for C₁₉H₁₅ClF₄N₂O₃S: C 49.30; H 3.27, N 6.05; Found: C 49.29, H 3.07, N 5.68.

Example 4

N-(4-tert-butylphenyl)-4-(3-chloropyridin-2-yl)-4-fluorocyclohex-1-ene-1-carboxamide The title compound was prepared using the procedure as described in Example 1E, except for substituting 4-tert-butylaniline for 4-(trifluoromethyl)aniline. ¹H NMR (300 MHz, DMSO-d₆) δ ppm 1.26 (s, 9H), 2.15-2.36 (m, 1H), 2.85-2.99 (m, 1H), 3.04-3.24 (m, 1H), 6.66 (s, 1H), 7.32 (d, J=8.81 Hz, 2H), 7.48 (ddd, J=8.14, 4.57, 0.85 Hz, 1H), 7.59 (d, J=8.82 Hz, 2H), 8.02 (dd, J=8.14, 1.70 Hz, 1H), 8.55 (d, J=4.41 Hz, 1H), 9.66 (s, 1H). ¹H NMR (300 MHz, CDCl₃) δ ppm 1.31 (s, 9H), 2.28-2.49 (m, 1H), 2.52-2.72 (m, 3H), 2.90-3.04 (m, 1H), 3.11-3.31 (m, 1H), 6.69 (s, 1H), 7.27 (dd, J=7.80, 4.74 Hz, 1H), 7.36 (d, J=8.81 Hz, 2H), 7.46 (s, 1H), 7.48 (d, J=8.82 Hz, 2H), 7.79 (dd, J=8.14, 1.36 Hz, 1H), 8.49 (d, J=4.41 Hz, 1H). MS (ESI) m/z 387.08 (M+H)⁺. Calcd for C₂₂H₂₄ClFN₂O: C, 68.30, H, 6.25, N, 7.24; Found: C, 67.92, H, 6.25, N, 7.07.

Example 5

4-(3-chloropyridin-2-yl)-4-fluoro-N-[4-(trifluoromethoxy)phenyl]cyclohex-1-ene-1-carboxamide The title compound was prepared using the procedure as described in Example 1E, except for substituting 4-(trifluoromethoxy)aniline for 4-(trifluoromethyl)aniline. ¹H NMR (300 MHz, DMSO-d₆) δ ppm 2.14-2.37 (m, 1H), 2.86-3.00 (m, 1H), 3.06-3.26 (m, 1H), 6.70 (s, 1H), 7.32 (d, J=9.15 Hz, 2H), 7.48 (ddd, J=8.14, 4.75, 0.68 Hz, 1H), 7.80 (d, J=9.15 Hz, 2H), 8.02 (dd, J=8.14, 1.70 Hz, 1H), 8.55 (d, J=4.75 Hz, 1H), 9.94 (s, 1H). $^1$H NMR (300 MHz, CD$_3$OD) δ ppm 2.27-2.66 (m, 4H), 2.86-2.99 (m, 1H), 6.72 (s, 1H), 7.23 (d, J=9.12 Hz, 2H), 7.36 (ddd, J=8.13, 4.56, 0.80 Hz, 1H), 7.71 (d, J=9.12 Hz, 2H), 7.89 (dd, J=8.14, 1.39 Hz, 1H), 8.48 (d, J=4.76 Hz, 1H). MS (ESI) m/z 414.98 (M+H)$^+$. Calcd for C$_{19}$H$_{15}$ClF$_4$N$_2$O$_2$: C, 55.02, H, 3.65, N, 6.75; Found: C, 54.79, H, 3.52, N, 6.74.

Example 6

4-(3-chloropyridin-2-yl)-N-[4-(1-cyano-1-methylethyl)phenyl]-4-fluorocyclohex-1-ene-1-carboxamide The title compound was prepared using the procedure as described in Example 1E, except for substituting 2-(4-aminophenyl)-2-methylpropanenitrile for 4-(trifluoromethyl)aniline. $^1$H NMR (300 MHz, DMSO-d$_6$) δ ppm 1.67 (s, 6H), 2.14-2.37 (m, 1H), 2.86-3.00 (m, 1H), 3.06-3.25 (m, 1H), 6.70 (s, 1H), 7.45 (d, J=8.82 Hz, 2H), 7.49 (ddd, J=8.14, 4.58, 0.85 Hz, 1H), 7.74 (d, J=9.15 Hz, 2H), 8.02 (dd, J=8.14, 1.36 Hz, 1H), 8.56 (d, J=4.41 Hz, 1H), 9.84 (s, 1H). $^1$H NMR (300 MHz, CDCl$_3$) δ ppm 1.72 (s, 6H), 2.25-2.47 (m, 1H), 2.54-2.72 (m, 3H), 2.91-3.05 (m, 1H), 3.12-3.32 (m, 1H), 6.72 (s, 1H), 7.24 (ddd, J=8.13, 4.41, 0.68 Hz, 1H), 7.44 (d, J=8.81 Hz, 2H), 7.49 (s, 1H), 7.59 (d, J=8.81 Hz, 2H), 7.76 (dd, J=8.14, 1.02 Hz, 1H), 8.46 (d, J=4.41 Hz, 1H). MS (ESI) m/z 398.05 (M+H)$^+$.

Example 7

N-(4-tert-butylphenyl)-4-(3-chloropyridin-2-yl)-4-methoxycyclohex-1-ene-1-carboxamide Example 7A 3-chloro-2-(8-methoxy-1,4-dioxaspiro[4.5]dec-8-yl)pyridine To a solution of the product of Example 1A (2.16 g, 8.00 mmol) in tetrahydrofuran (70 mL) was added 60% sodium hydride (0.96 g, 24.0 mmol) in portions, followed by addition of methyl iodide (1.6 mL, 25.6 mmol). The reaction mixture was stirred at ambient temperature for 5 hours, quenched with saturated ammonium chloride (300 mL), extracted with ethyl acetate (300 mL), washed with water (300 mL), brine, dried with anhydrous sodium sulfate, filtered, and concentrated to a yellow oil. The residue was chromatographed on silica gel, eluting with 0-to-30% ethyl acetate in hexanes to provide 2.147 g (94% yield) of the title compound as a colorless oil. $^1$H NMR (300 MHz, DMSO-d$_6$) δ ppm 1.59 (d, J=12.55 Hz, 2H), 1.80 (td, J=12.88, 3.73 Hz, 2H), 2.04 (td, J=13.57, 3.73 Hz, 2H), 2.23-2.32 (m, 2H), 2.92 (s, 3H), 3.87 (s, 4H), 7.37 (dd, J=7.97, 4.58 Hz, 1H), 7.88 (dd, J=7.97, 1.53 Hz, 1H), 8.51 (dd, J=4.58, 1.53 Hz, 1H). MS (DCI) m/z 284.13 (M+H)$^+$.

Example 7B 4-(3-chloropyridin-2-yl)-4-methoxycyclohexanone

To a solution of the product of Example 7A (2.147 g, 7.57 mmol) in dioxane (40 mL) was added 3N hydrochloric acid (25 mL). The reaction mixture was stirred at ambient temperature for 3 hours, quenched with 3N sodium hydroxide (35 mL), followed by addition of water (200 mL), extracted twice with ethyl acetate (200 mL), washed with water (200 mL) and brine, dried with anhydrous sodium sulfate, filtered and concentrated to a yellow oil. The residue was chromatographed on silica gel, eluting with 0-to-30% ethyl acetate in hexane to provide 1.698 g (94% yield) of the title compound as a white solid. $^1$H NMR (300 MHz, DMSO-d$_6$) δ ppm 2.17-2.31 (m, 4H), 2.54-2.65 (m, 4H), 3.01 (s, 3H), 7.42 (dd, J=7.97, 4.58 Hz, 1H), 7.94 (dd, J=8.14, 1.36 Hz, 1H), 8.54 (dd, J=4.58, 1.53 Hz, 1H). MS (DCI) m/z 240.05 (M+H)$^+$.

Example 7C 4-(3-chloropyridin-2-yl)-4-methoxycyclohex-1-en-1-yl trifluoromethanesulfonate A solution of the product of Example 7B (1.648 g, 6.88 mmol) and 1,1,1-trifluoro-N-phenyl-N-(trifluoromethylsulfonyl)methanesulfonamide (2.59 g, 7.25 mmol) in tetrahydrofuran (35 mL) was chilled to −75° C., followed by dropwise addition of lithium bis(trimethylsilyl)amide (1.0M in tetrahydrofuran, 8.4 mL, 8.4 mmol) over 10 minutes. The resulting mixture was stirred at −75° C. for 50 minutes, then warmed to ambient temperature by removing the cold bath, and stirred for 2 hours. The mixture was then treated with 1N sodium hydroxide (200 mL) and extracted twice with 1:1 ethyl acetate:hexanes (200 mL). The combined organic layers were washed with 1N sodium hydroxide (200 mL), water (200 mL), and brine, dried with anhydrous sodium sulfate, filtered, and concentrated to an orange oil. The residue was chromatographed on silica gel, eluting with 0-to-25% ethyl acetate in hexanes to provide 2.089 g (82% yield) of the title compound as a colorless oil. $^1$H NMR (300 MHz, CDCl$_3$) δ ppm 2.20-2.29 (m, 1H), 2.42-2.63 (m, 3H), 2.81-2.98 (m, 2H), 3.07 (s, 3H), 5.75 (t, J=4.24 Hz, 1H), 7.20 (dd, J=7.97, 4.58 Hz, 1H), 7.71 (dd, J=7.97, 1.53 Hz, 1H), 8.45 (dd, J=4.58, 1.53 Hz, 1H). MS (DCI) m/z 372.07 (M+H)$^+$.

Example 7D

N-(4-tert-butylphenyl)-4-(3-chloropyridin-2-yl)-4-methoxycyclohex-1-ene-1-carboxamide The title compound was prepared using the procedure as described in Example 1E, except for substituting 4-tert-butylaniline for 4-(trifluoromethyl)aniline, and substituting the product of Example 7C for the product of Example 1D. $^1$H NMR (300 MHz, DMSO-d$_6$) δ ppm 1.26 (s, 9H), 2.20-2.42 (m, 4H), 2.85 (s, 2H), 2.95 (s, 3H), 6.65 (t, J=3.77 Hz, 1H), 7.30 (d, J=8.72 Hz, 2H), 7.41 (dd, J=8.13, 4.56 Hz, 1H), 7.57 (d, J=8.72 Hz, 2H), 7.94 (dd, J=8.13, 1.39 Hz, 1H), 8.53 (dd, J=4.76 Hz, 1.58 Hz, 1H), 9.54 (s, 1H). MS (ESI) m/z 399.12 (M+H)$^+$. Calcd for C$_{23}$H$_{27}$ClN$_2$O$_2$: C, 69.25, H, 6.82, N, 7.02; Found: C, 69.34, H, 6.79, N, 7.24.

Example 8

4-(3-chloropyridin-2-yl)-4-methoxy-N-{4-[(trifluoromethyl)sulfonyl]phenyl}cyclohex-1-ene-1-carboxamide The title compound was prepared using the procedure as described in Example 1E, except for substituting 4-(trifluoromethylsulfonyl)aniline for 4-(trifluoromethyl)aniline, and substituting the product of Example 7C for the product of Example 1D. $^1$H NMR (300 MHz, DMSO-d$_6$) δ ppm 2.21-2.44 (m, 4H), 2.90 (s, 2H), 2.96 (s, 3H), 6.81 (t, J=3.90 Hz, 1H), 7.42 (dd, J=8.14, 4.41 Hz, 1H), 7.95 (dd, J=7.97, 1.52 Hz, 1H), 8.06 (d, J=9.16 Hz, 2H), 8.14 (d, J=9.16 Hz, 2H), 8.53 (dd, J=4.75, 1.35 Hz, 1H), 10.39 (s, 1H). MS (ESI) m/z 475.02 (M+H)+. Calcd for $C_{20}H_{18}ClF_3N_2O_4S.0.16$ TFA: C, 49.49, H, 3.71, N, 5.68; Found: C, 49.57, H, 3.57, N, 5.42.

Example 9

4-(3-chloropyridin-2-yl)-4-methoxy-N-[4-(trifluoromethyl)phenyl]cyclohex-1-ene-1-carboxamide The title compound was prepared using the procedure as described in Example 1E, except for substituting the product of Example 7C for the product of Example 1D. $^1$H NMR (300 MHz, DMSO-$d_6$) δ ppm 2.21-2.43 (m, 4H), 2.87 (s, 2H), 2.96 (s, 3H), 6.73 (t, J=3.77 Hz, 1H), 7.41 (dd, J=8.13, 4.56 Hz, 1H), 7.66 (d, J=9.12 Hz, 2H), 7.92 (d, J=9.52 Hz, 2H), 7.95 (dd, J=7.93, 1.58 Hz, 1H), 8.54 (dd, J=4.56, 1.39 Hz, 1H), 9.99 (s, 1H). MS (ESI) m/z 411.02 (M+H)+. Calcd for $C_{20}H_{18}ClF_3N_2O_2$. 0.13 TFA: C, 57.17, H, 4.29, N, 6.58; Found: C, 57.19, H, 3.84, N, 6.44.

Example 10

4-fluoro-4-(3-methylpyridin-2-yl)-N-[4-(trifluoromethyl)phenyl]cyclohex-1-ene-1-carboxamide

Example 10A

8-(3-methylpyridin-2-yl)-1,4-dioxaspiro[4.5]decan-8-ol

The title compound was prepared using the procedure as described in Example 1A, except for substituting 3-methyl-2-bromopyridine for 3-chloro-2-bromopyridine.
$^1$H NMR (300 MHz, DMSO-$d_6$) δ 8.32 (dd, J 1.5 and 4.5 Hz, 1H), 7.52 (dd, J 1.5 and 7.5 Hz, 1H), 7.16 (dd, J 4.5 and 7.5 Hz, 1H), 5.21 (s, 1H), 3.85 (s, 4H), 2.53 (s, 3H), 2.20 (m, 2H), 1.92 (m, 2H), 1.70 (m, 2H), 1.58 (m, 2H). MS (DCI/NH$_3$) m/e 250 (M+H)+.

Example 10B

2-(8-fluoro-1,4-dioxaspiro[4.5]dec-8-yl)-3-methylpyridine

The title compound was prepared using the procedure as described in Example 1B, except for substituting the product of Example 10A for the product of Example 1A. $^1$H NMR (300 MHz, DMSO-$d_6$) δ 8.37 (d, J=4.5 Hz, 1H), 7.60 (d, J=7.5 Hz, 1H), 7.23 (dd, J 4.5 and 7.5 Hz, 1H), 3.90 (s, 4H), 2.45-1.62 (m, 11H). MS (DCI/NH$_3$) m/e 252 (M+H)+.

Example 10C

4-fluoro-4-(3-methylpyridin-2-yl)cyclohexanone

The title compound was prepared using the procedure as described in Example 1C, except for substituting the product of Example 10B for the product of Example 1B. $^1$H NMR (300 MHz, DMSO-$d_6$) δ ppm 8.37 (d, J=4.4 Hz, 1 H) 7.66 (d, J=6.8 Hz, 1 H) 7.29 (dd, J=6.8, 4.4 Hz, 1 H), 2.54-2.93 (m, 4 H), 2.51 (s, 3 H), 2.18-2.46 (m, 4 H). MS (DCI) m/e 208 (M+H)+.

Example 10D

4-fluoro-4-(3-methylpyridin-2-yl)cyclohex-1-en-1-yl trifluoromethanesulfonate The title compound was prepared using the procedure as described in Example 1D, except for substituting the product of Example 10C for the product of Example 1C. $^1$H NMR (300 MHz, DMSO-$d_6$) δ ppm 8.37 (d, J=5.2 Hz, 1 H) 7.66 (d, J=7.1 Hz, 1 H) 7.30 (dd, J=7.1, 5.2 Hz, 1 H) 5.86-6.01 (m, 1 H) 2.99-3.29 (m, 2 H) 2.54-2.86 (m, 2 H) 2.47 (d, J=5.6 Hz, 3 H) 2.27-2.44 (m, 2 H). MS (DCI) m/e 340(M+H)+.

Example 10E

4-fluoro-4-(3-methylpyridin-2-yl)-N-[4-(trifluoromethyl)phenyl]cyclohex-1-ene-1-carboxamide The title compound was prepared using the procedure as described in Example 1E, except for substituting the product of Example 10D for the product of Example 1D. $^1$H NMR (300 MHz, DMSO-$d_6$) δ ppm 10.09 (s, 1 H), 8.39 (d, J=4.8 Hz, 1 H), 7.93 (d 2 H), 7.68 (m, 3 H), 7.30 (dd, J=7.80, 4.8 Hz, 1 H), 6.72-6.79 (m, 1 H), 3.06-3.25 (m, 2 H), 2.66-2.86 (m, 2 H), 2.51 (s, 3 H), 2.04-2.38 (m, 2 H). MS (ESI) m/e 379(M+H)+. Calc. for $C_{20}H_{18}F_4N_2O.0.2H_2O$: C, 62.89, H, 4.86, N, 7.33; Found C, 62.81, H, 4.71, N, 7.38.

Example 11

4-fluoro-4-(3-methylpyridin-2-yl)-N-[4-(trifluoromethoxy)phenyl]cyclohex-1-ene-1-carboxamide The title compound was prepared using the procedure as described in Example 1E, except for substituting the product of Example 10D for the product of Example 1D and substituting 4-trifluoromethoxyaniline for 4-trifluoromethylaniline. $^1$H NMR (300 MHz, DMSO-$d_6$) δ ppm 9.93 (s, 1 H), 8.39 (m, 1 H) 7.77-7.85 (m, 2 H), 7.67 (m, 1 H), 7.22-7.36 (m, 3 H), 6.71 (br s, 1 H), 3.26-3.36 (m, 2 H), 3.00-3.24 (m, 1 H), 2.62-2.87 (m, 1 H), 2.51 (s, 3 H), 2.01-2.38 (m, 2 H). MS (ESI) m/e 395(M+H)+. Calc. for $C_{20}H_{18}F_4N_2O_2$: C, 60.91, H, 4.60, N, 7.10; Found C, 60.75, H, 4.45, N, 7.03.

Example 12

4-fluoro-4-(3-methylpyridin-2-yl)-N-{4-[(trifluoromethyl)sulfonyl]phenyl}cyclohex-1-ene-1-carboxamide The title compound was prepared using the procedure as described in Example 1E, except for substituting the product of Example 10D for Example 1D and substituting 4-trifluoromethylsulfonylaniline for 4-trifluoromethylaniline. $^1$H NMR (300 MHz, DMSO-$d_6$) δ ppm 10.49 (s, 1 H) 8.11-8.23 (m, 2 H), 8.01-8.11 (m, 2 H), 7.67 (d, J=7.1 Hz, 1 H), 7.30 (m, 1 H), 6.83 (br s, 1 H), 3.26-3.36 (m, 2 H), 3.04-3.26 (m, 1 H), 2.61-2.93 (m, 1 H), 2.50 (s, 3 H), 1.86-2.41 (m, 2 H). MS (ESI) m/e 443(M+H)+. Calc. for $C_{20}H_{18}F_4N_2O_3S$: C, 54.30, H, 4.10, N, 6.33; Found C, 54.07, H, 3.97, N, 6.23.

Example 13

N-(4-chlorophenyl)-4-fluoro-4-(3-methylpyridin-2-yl)cyclohex-1-ene-1-carboxamide The title compound was prepared using the procedure as described in Example 1E, except for substituting the product of Example 10D for the product of Example 1D and substituting 4-chloroaniline for 4-trifluoromethylaniline. $^1$H NMR (300 MHz, DMSO-$d_6$) δ ppm 9.87 (s, 1H) 8.39 (d, J=4.4 Hz, 1 H), 7.71-7.83 (m, 2 H), 7.66 (d, J=6.7 Hz, 1 H), 7.18-7.46 (m, 3 H), 6.70 (s, 1 H), 3.26-3.36 (m, 2 H), 3.02-3.23 (m, 1 H), 2.61-2.88 (m, 1 H), 2.51 (s, 3 H) 2.02-2.37 (m, 2 H). Calc. for $C_{19}H_{18}ClFN_2O \cdot 0.1H_2O$: C, 65.84, H, 5.29, N, 8.08; Found C, 65.70, H, 5.02, N, 7.98.

Example 14

N-(4-tert-butylphenyl)-4-fluoro-4-(3-methylpyridin-2-yl)cyclohex-1-ene-1-carboxamide The title compound was prepared using the procedure as described in Example 1E, except for substituting the product of Example 10D for the product of Example 1D and substituting 4-tert-butylaniline for 4-trifluoromethylaniline. $^1$H NMR (300 MHz, DMSO-$d_6$) δ ppm 9.64 (s, 1 H), 8.39 (d, J=4.4 Hz, 1 H) 7.49-7.78 (m, 3 H), 7.16-7.41 (m, 3 H), 6.67 (br s, 1 H), 3.22-3.30 (m, 1 H), 2.94-3.22 (m, 1 H), 2.64-2.86 (m, 1 H), 2.51 (s, 3 H), 1.96-2.37 (m, 2 H), 1.27 (s, 9 H). MS (ESI) m/e 367 (M+H)$^+$. Calc. for $C_{23}H_{27}FN_2O$: C, 75.38, H, 7.43, N, 7.64; Found C, 75.17, H, 7.33, N, 7.58.

Example 15

4-fluoro-4-(3-fluoropyridin-2-yl)-N-[4-(trifluoromethyl)phenyl]cyclohex-1-ene-1-carboxamide

Example 15A

8-(3-fluoropyridin-2-yl)-1,4-dioxaspiro[4.5]decan-8-ol

The title compound was prepared using the procedure as described in Example 1A, except for substituting 3-fluoro-2-bromopyridine for 3-chloro-2-bromopyridine. $^1$H NMR (300 MHz, DMSO-$d_6$) δ 8.36 (m, 1H), 7.66 (m, 1H), 7.41 (m, 1H), 5.21 (s, 1H), 3.85 (s, 4H), 2.20 (m, 2H), 1.92 (m, 2H), 1.74 (m, 2H), 1.59 (m, 2H). MS (DCI/NH$_3$) m/e 254 (M+H)$^+$.

Example 15B

3-fluoro-2-(8-fluoro-1,4-dioxaspiro[4.5]dec-8-yl)pyridine

The title compound was prepared using the procedure as described in Example 1B, except for substituting the product of Example 15A for the product of Example 1A. $^1$H NMR (300 MHz, DMSO-$d_6$) δ 8.41 (m, 1H), 7.78 (m, 1H), 7.50 (m, 1H), 3.90 (s, 4H), 2.38-1.70 (m, 8H). MS (DCI/NH$_3$) m/e 252 (M+H)$^+$.

Example 15C

4-fluoro-4-(3-fluoropyridin-2-yl)cyclohexanone

The title compound was prepared using the procedure as described in Example 1C, except for substituting the product of Example 15B for the product of Example 1B. $^1$H NMR (300 MHz, DMSO-$d_6$) δ 8.41 (m, 1H), 7.80 (m, 1H), 7.56 (m, 1H), 2.80-2.22 (m, 8H). MS (DCI/NH$_3$) m/e 212 (M+H)$^+$.

Example 15D

4-fluoro-4-(3-fluoropyridin-2-yl)cyclohex-1-en-1-yl trifluoromethanesulfonate The title compound was prepared using the procedure as described in Example 1D, except for substituting the product of Example 15C for the product of Example 1C. $^1$H NMR (300 MHz, DMSO-$d_6$) δ 8.41 (m, 1H), 7.81 (m, 1H), 7.58 (m, 1H), 5.95 (m, 1H), 3.20-2.20 (m, 6H). MS (DCI/NH$_3$) m/e 344 (M+H)$^+$.

Example 15E

4-fluoro-4-(3-fluoropyridin-2-yl)-N-[4-(trifluoromethyl)phenyl]cyclohex-1-ene-1-carboxamide The title compound was prepared using the procedure as described in Example 1E, except for substituting the product of Example 15D for the product of Example 1D. $^1$H NMR (300 MHz, DMSO-$d_6$) δ ppm 10.10 (s, 1 H), 8.45 (d, J=4.4 Hz, 1 H), 7.78-8.00 (m, 3 H), 7.68 (d, J=8.5 Hz, 2 H), 7.50-7.62 (m, 1 H), 6.65-6.85 (m, 1 H), 3.23-3.32 (m, 1 H), 3.03-3.22 (m, 1 H), 2.69-2.96 (m, 1 H), 2.51-2.60 (m, 1 H), 2.38-2.47 (m, 1 H), 2.04-2.31 (m, 1 H). MS (ESI) m/e 383 (M+H)$^+$. Calc. for $C_{19}H_{15}F_5N_2O$: C, 59.69, H, 3.95, N, 7.33; Found C, 59.73, H, 3.83, N, 7.29.

Example 16

N-(4-tert-butylphenyl)-4-fluoro-4-(3-fluoropyridin-2-yl)cyclohex-1-ene-1-carboxamide The title compound was prepared using the procedure as described in Example 1E, except for substituting the product of Example 15D for Example 1D and substituting 4-tert-butylaniline for 4-trifluoromethylaniline. $^1$H NMR (300 MHz, DMSO-$d_6$) δ ppm 9.66 (s, 1 H) 8.45 (d, J=4.4 Hz, 1 H) 7.83 (dd, J=11.9, 7.1 Hz, 1 H) 7.48-7.68 (m, 3 H) 7.23-7.39 (m, 2 H) 6.67 (br s, 1 H) 3.25-3.43 (m, 2 H) 2.98-3.21 (m, 1 H) 2.67-2.94 (m, 1 H) 2.35-2.46 (m, 1 H) 1.98-2.33 (m, 1 H) 1.26 (s, 9 H). MS (ESI) m/e (M+H)$^+$. Calc. for $C_{22}H_{24}F_2N_2O$: C, 71.33, H, 6.53, N, 7.56. Found C, 71.19, H, 6.59, N, 7.54.

Example 17

4-fluoro-4-(3-fluoropyridin-2-yl)-N-[5-(trifluoromethyl)pyridin-2-yl]cyclohex-1-ene-1-carboxamide The title compound was prepared using the procedure as described in Example 1E, except for substituting Example the product of 15D for the product of Example 1D and substituting 2-amino-5-trifluoromethylpyridine for 4-trifluoromethylaniline. $^1$H NMR (300 MHz, DMSO-$d_6$) δ ppm 10.65 (br s, 1 H), 8.73 (m, 1 H), 8.44 (m, 1 H), 8.28 (m, 1 H), 8.18 (m, 1 H), 7.82 (m, 1 H), 7.56 (m, 1 H) 6.90 (m, 1 H) 3.22-3.42 (m, 1 H) 3.01-3.22 (m, 1 H) 2.67-2.95 (m, 1 H) 2.51-2.61 (m, 1 H) 2.33-2.46 (m, 1 H) 2.02-2.31 (m, 1 H). MS (ESI) m/e 384 (M+H)$^+$. Calc. for $C_{18}H_{14}F_5N_3O$: C, 56.40, H, 3.68, N, 10.96; Found C, 56.41, H, 3.45, N, 10.74.

Example 18

4-fluoro-4-(3-fluoropyridin-2-yl)-N-{4-[(trifluoromethyl)sulfonyl]phenyl}cyclohex-1-ene-1-carboxamide The title compound was prepared using the procedure as described in Example 1E, except for substituting the product of Example 15D for the product of Example 1D and substituting 4-trifluoromethylsulfonylaniline for 4-trifluoromethylaniline. $^1$H NMR (300 MHz, DMSO-$d_6$) δ ppm 10.48 (s, 1 H), 8.45 (d, J=4.4 Hz, 1 H), 8.11-8.20 (m, 2 H), 8.01-8.11 (m, 2 H), 7.76-7.89 (m, 1 H), 7.50-7.62 (m, 1 H), 3.28-3.36 (m, 1 H), 3.04-3.26 (m, 1 H), 2.76-2.98 (m, 1 H), 2.51-2.57 (m, 1

H), 2.37-2.47 (m, 1 H), 2.02-2.34 (m, 1 H). MS (ESI) m/e 447 (M+H)+. Calc. for $C_{19}H_{15}F_5N_2O_3S$: C, 51.12, H, 3.39, N, 6.28; Found C, 50.97, H, 3.32, N, 6.09.

Example 19

4-fluoro-4-(3-fluoropyridin-2-yl)-N-[4-(pentafluoro-$\lambda^6$-sulfanyl)phenyl]cyclohex-1-ene-1-carboxamide The title compound was prepared using the procedure as described in Example 1E, except for substituting the product of Example 15D for the product of Example 1D, and substituting 4-aminophenylsulphur pentafluoride (Aldrich) for 4-trifluoromethylaniline. $^1$H NMR (300 MHz, DMSO-$d_6$) δ ppm 10.18 (s, 1 H), 8.45 (d, J=4.4 Hz, 1 H), 7.74-8.00 (m, 6 H), 7.44-7.66 (m, 1 H), 6.76 (br s, 1 H), 3.23-3.41 (m, 1 H), 3.01-3.23 (m, 1 H), 2.66-2.98 (m, 1 H), 2.36-2.60 (m, 2 H, under DMSO), 2.00-2.33 (m, 1 H). MS (ESI) m/e 441 (M+H)+. Calc. for $C_{18}H_{15}F_7N_2OS$: C, 49.09, H, 3.43, N, 6.36; Found C, 49.05, H, 3.35, N, 6.26.

Example 20

4-fluoro-4-(1,3-thiazol-2-yl)-N-[4-(trifluoromethyl)phenyl]cyclohex-1-ene-1-carboxamide

Example 20A

8-(1,3-thiazol-2-yl)-1,4-dioxaspiro[4.5]decan-8-ol

The title compound was prepared using the procedure as described in Example 1A, except for substituting 2-bromothiazole for 3-chloro-2-bromopyridine. $^1$H NMR (300 MHz, DMSO-$d_6$) δ ppm 7.69 (m, 1 H), 7.51-7.57 (m, 1 H), 3.87 (s, 4 H), 2.11 (m, 2 H), 1.69-1.95 (m, 4 H), 1.52-1.70 (m, 2 H). MS (DCI) m/e 242 (M+H)+.

Example 20B

2-(8-fluoro-1,4-dioxaspiro[4.5]dec-8-yl)-1,3-thiazole

The title compound was prepared using the procedure as described in Example 1B, except for substituting the product of Example 20A for the product of Example 1A. $^1$H NMR (300 MHz, DMSO-$d_6$) δ ppm 7.67-7.99 (m, 2 H), 3.97 (s, 4 H), 2.23-2.40 (m, 1 H), 2.06-2.25 (m, 3 H), 1.64-1.92 (m, 4 H). MS (DCI) m/e 244 (M+H)+.

Example 20C

4-fluoro-4-(1,3-thiazol-2-yl)cyclohexanone

The title compound was prepared using the procedure as described in Example 1C, except for substituting the product of Example 20B for the product of Example 1B. $^1$H NMR (300 MHz, DMSO-$d_6$) δ ppm 7.82-7.95 (m, 2 H), 2.61-2.72 (m, 6 H), 2.24-2.42 (m, 2 H). MS (DCI) m/e 200 (M+H)+.

Example 20D

4-fluoro-4-(1,3-thiazol-2-yl)cyclohex-1-en-1-yl trifluoromethanesulfonate

The title compound was prepared using the procedure as described in Example 1D, except for substituting the product of Example 20C for the product of Example 1C. $^1$H NMR (300 MHz, DMSO-$d_6$) δ ppm 7.85-7.95 (m, 2 H), 5.90-6.08 (m, 1 H), 2.94-3.21 (m, 1 H), 2.74-2.95 (m, 1 H), 2.58-2.74 (m, 1 H), 2.17-2.50 (m, 3 H). MS (DCI) m/e 332 (M+H)+.

Example 20E

4-fluoro-4-(1,3-thiazol-2-yl)-N-[4-(trifluoromethyl)phenyl]cyclohex-1-ene-1-carboxamide The title compound was prepared using the procedure as described in Example 1E, except for substituting the product of Example 20D for the product of Example 1D. $^1$H NMR (300 MHz, DMSO-$d_6$) δ ppm 10.13 (s, 1 H), 7.81-8.08 (m, 4 H), 7.68 (d, J=8.5 Hz, 2 H), 6.72 (br s, 1 H), 2.97-3.26 (m, 1 H), 2.69-2.98 (m, 1 H), 2.51-2.66 (m, 1 H), 2.20-2.41 (m, 2 H), 1.95-2.21 (m, 1 H). MS (ESI) m/e 371(M+H)+. Calc. for $C_{17}H_{14}F_4N_2OS$: C, 55.13, H, 3.81, N, 7.56; Found C, 55.16, H, 3.65, N, 7.51.

Example 21

4-fluoro-4-(1,3-thiazol-2-yl)-N-{4-[(trifluoromethyl)sulfonyl]phenyl}cyclohex-1-ene-1-carboxamide The title compound was prepared using the procedure as described in Example 1E, except for substituting the product of Example 20D for Example 1D and substituting 4-trifluoromethylsulfonylaniline for 4-trifluoromethylaniline. $^1$H NMR (300 MHz, DMSO-$d_6$) δ ppm 10.52 (s, 1 H), 7.99-8.23 (m, 4 H), 7.82-7.96 (m, 2 H), 6.79 (br s, 1 H), 2.99-3.26 (m, 1 H), 2.92 (m, 1 H), 2.73 (m, 1 H), 2.20-2.43 (m, 2 H), 2.04-2.21 (m, 1 H). MS (ESI) m/e 435(M+H)+. Calc. for $C_{17}H_{14}F_4N_2O_3S_2$: C, 47.00, H, 3.25, N, 6.45; Found C, 47.26, H, 3.25, N, 6.33.

Example 22

(4R)—N-(4-chlorophenyl)-4-(3-chloropyridin-2-yl)-4-fluorocyclohex-1-ene-1-carboxamide The title compound was obtained by chiral separation of the product of Example 2 on a ChiralCel OJ column with 50% isopropanol in hexanes. $^1$H NMR (300 MHz, DMSO-$d_6$) δ ppm 2.14-2.36 (m, 1H), 2.86-2.99 (m, 1H), 3.06-3.25 (m, 1H), 6.69 (s, 1H), 7.37 (d, J=9.12 Hz, 2H), 7.48 (dd, J=8.13, 4.56 Hz, 1H), 7.73 (d, J=8.73 Hz, 2H), 8.02 (dd, J=8.13, 1.39 Hz, 1H), 8.56 (d, J=3.97 Hz, 1H), 9.88 (s, 1H). MS (ESI) m/z 364.93 (M+H)+. $[\alpha]_D$: +11.6° (c: 1.0, $CH_3OH$). Calcd for $C_{18}H_{15}Cl_2FN_2O$: C, 59.19, H, 4.14, N, 7.67; Found: C, 58.98, H, 3.90, N, 7.47.

Example 23

(4S)—N-(4-chlorophenyl)-4-(3-chloropyridin-2-yl)-4-fluorocyclohex-1-ene-1-carboxamide The title compound was obtained by chiral separation of the product of Example 2 on a ChiralCel OJ column with 50% isopropanol in hexanes. $^1$H NMR (300 MHz, DMSO-$d_6$) δ ppm 2.13-2.36 (m, 1H), 2.86-2.99 (m, 1H), 3.06-3.25 (m, 1H), 6.69 (s, 1H), 7.36 (d, J=9.12 Hz, 2H), 7.49 (ddd, J=8.13, 4.56, 0.79 Hz, 1H), 7.73 (d, J=9.13 Hz, 2H), 8.02 (dd, J=8.13, 1.39 Hz, 1H), 8.55 (d, J=4.36 Hz, 1H), 9.88 (s, 1H). MS (ESI) m/z 364.92 (M+H)+. $[\alpha]_D$: −9.7°(c: 1.0, $CH_3OH$). Calcd for $C_{18}H_{15}Cl_2FN_2O$: C, 59.19, H, 4.14, N, 7.67; Found: C, 58.85, H, 3.91, N, 7.39.

Example 24

(4R)-4-(3-chloropyridin-2-yl)-4-fluoro-N-[4-(trifluoromethyl)phenyl]cyclohex-1-ene-1-carboxamide The title compound was obtained by chiral separation of the product of Example 1 on a ChiralPak AD-H column with 24% ethanol in supercritical fluid $CO_2$— $^1$H NMR (300 MHz, DMSO-$d_6$) δ ppm 2.14-2.36 (m, 1H), 2.88-3.01 (m, 1H), 3.08-3.20 (m, 1H), 6.75 (s, 1H), 7.48 (ddd, J=8.13, 4.56, 0.79 Hz, 1H), 7.68 (d, J=8.33 Hz, 2H), 7.93 (d, J=8.32 Hz, 2H), 8.03 (dd, J=8.33, 1.59 Hz, 1H), 8.56 (d, J=4.36 Hz, 1H), 10.10 (s, 1H). $^1$H NMR (300 MHz, CDCl$_3$) δ ppm 2.25-2.47 (m, 1H), 2.55-2.72 (m, 3H), 2.92-3.05 (m, 1H), 3.14-3.33 (m, 1H), 6.74 (s, 1H), 7.23-7.27 (m, 1H), 7.58-7.61 (m, 3H), 7.71 (d, J=8.73 Hz, 2H), 7.77 (dd, J=7.93, 1.19 Hz, 1H), 8.46 (d, J=4.76 Hz, 1H). MS (ESI) m/z 398.98 (M+H)$^+$. [α]$_D$: +11.4° (c: 1.0, CH$_3$OH). Calcd for C$_{19}$H$_{15}$ClF$_4$N$_2$O: C, 57.23, H, 3.79, N, 7.02; Found: C, 57.17, H, 3.63, N, 6.95.

Example 25

(4S)-4-(3-chloropyridin-2-yl)-4-fluoro-N-[4-(trifluoromethyl)phenyl]cyclohex-1-ene-1-carboxamide The title compound was obtained by chiral separation of the product of Example 1 on a ChiralPak AD-H column with 24% ethanol in supercritical fluid $CO_2$— $^1$H NMR (300 MHz, DMSO-$d_6$) δ ppm 2.16-2.36 (m, 1H), 2.94-3.01 (m, 1H), 3.08-3.21 (m, 1H), 6.75 (s, 1H), 7.49 (ddd, J=8.14, 4.75, 0.68 Hz, 1H), 7.68 (d, J=8.47 Hz, 2H), 7.93 (d, J=8.48 Hz, 2H), 8.03 (dd, J=8.14, 1.69 Hz, 1H), 8.56 (d, J=4.75 Hz, 1H), 10.11 (s, 1H). $^1$H NMR (300 MHz, CDCl$_3$) δ ppm 2.25-2.47 (m, 1H), 2.55-2.72 (m, 3H), 2.92-3.05 (m, 1H), 3.14-3.33 (m, 1H), 6.74 (s, 1H), 7.23-7.27 (m, 1H), 7.58-7.61 (m, 3H), 7.71 (d, J=8.73 Hz, 2H), 7.77 (dd, J=8.13, 1.39 Hz, 1H), 8.46 (d, J=4.37 Hz, 1H). MS (ESI) m/z 398.96 (M+H)$^+$. [α]$_D$: −10.3° (c: 1.0, CH$_3$OH). Calcd for C$_{19}$H$_{15}$ClF$_4$N$_2$O: C, 57.23, H, 3.79, N, 7.02; Found: C, 57.21, H, 3.72, N, 6.95.

Example 26

4-(3-(Dimethylamino)pyridin-2-yl)-4-(trifluoromethyl)-N-(4-(trifluoromethyl)phenyl)cyclohex-1-enecarboxamide

Example 26A

3-Chloro-2-(3,3,3-trifluoroprop-1-en-2-yl)pyridine

To a solution of 2-bromo-3-chloropyridine (Matrix, 1.651 g, 8.58 mmol), 4,4,6-trimethyl-2-(3,3,3-trifluoroprop-1-en-2-yl)-1,3,2-dioxaborinane (Frontier, 2.0 g, 9.01 mmol), and potassium carbonate (4.74 g, 34.3 mmol) in degassed 1,2-dimethoxyethane (50 mL) and water (25 mL) was added tetrakis(triphenylphosphine)palladium (496 mg, 0.429 mmol). The reaction mixture was refluxed for 8 hours, cooled to ambient temperature, diluted with water (200 mL), extracted twice with diethyl ether (200 mL), washed with brine, dried (Na$_2$SO$_4$) and concentrated to a yellow liquid. The residue was purified by silica gel chromatography (AnaLogix® SF25-40G; 50 micron silica; elution with 0-20% ethyl acetate in hexane at 30 mL/min) to provide the title compound (1.530 g, 7.37 mmol, 86% yield) as a colorless liquid. $^1$H NMR (300 MHz, DMSO-$d_6$) δ ppm 8.61 (dd, J=4.6, 1.4, 1H), 8.10 (dd, J=8.2, 1.4, 1H), 7.53 (dd, J=8.3, 4.6, 1H), 6.51-6.46 (m, 1H), 6.13-6.10 (m, 1H); MS (EI) m/e 207 (M)$^+$.

Example 26B 4-(3-(Dimethylamino)pyridin-2-yl)-4-(trifluoromethyl)cyclohex-2-enone A solution of Example 26A (418 mg, 2.014 mmol) and (E)-3-(tert-butyldimethylsilyloxy)-N,N-dimethylbuta-1,3-dien-1-amine (Aldrich, 527 mg, 2.316 mmol) in toluene (1.5 mL) was heated in a microwave at 140° C. for 2 hours, and then chromatographed on silica gel (AnaLogix SF15-24G; 50 micron silica; elution with 0-50% ethyl acetate in hexane at 20 mL/min). Repeated the reaction in a microwave at 120° C. for 2 hours with a solution of Example 26A (422 mg, 2.033 mmol) and (E)-3-(tert-butyldimethylsilyloxy)-N,N-dimethylbuta-1,3-dien-1-amine (693 mg, 3.05 mmol) in toluene (2 mL), and then chromatographed on silica gel (AnaLogix® SF15-24G; 50 micron silica; elution with 0-50% ethyl acetate in hexane at 20 mL/min). The title compound (165 mg, 0.580 mmol) was isolated as an orange solid. A solution of the isolated intermediate 7-(tert-butyldimethylsilyloxy)-5,5-dimethyl-9a-(trifluoromethyl)-5a,8,9,9a-tetrahydro-5H-pyrido[3,2-b]indol-5-ium chloride (395 mg, 0.908 mmol) in tetrahydrofuran (9 mL) was treated with 1N hydrochloric acid (3.0 mL, 3.0 mmol). The reaction mixture was stirred overnight at ambient temperature, quenched with sodium bicarbonate solution (40 mL), extracted twice with ethyl acetate (40 mL), washed with brine, dried (Na$_2$SO$_4$), and concentrated to an orange oil. The residue was purified by silica gel chromatography (AnaLogix® SF 10-8G; 50 micron silica; elution with 0-40% ethyl acetate in hexane at 15 mL/min) to provide additional title compound (131 mg, 0.461 mmol) as an off-white solid. $^1$H NMR (300 MHz, CDCl$_3$) δ ppm 8.54 (dd, J=4.5, 1.6, 1H), 7.75 (dd, J=8.0, 1.7, 1H), 7.74 (dd, J=10.2, 2.1, 1H), 7.35 (dd, J=8.1, 4.5, 1H), 5.90 (d, J=10.2, 1H), 3.54-3.44 (m, 1H), 2.65 (s, 3H), 2.45-2.35 (m, 2H), 2.33 (s, 3H), 2.13-1.97 (m, 1H); MS (DCI/NH$_3$) m/e 285 (M+H)$^+$.

Example 26C 4-(3-(Dimethylamino)pyridin-2-yl)-4-(trifluoromethyl)cyclohexanone Example 26B (261 mg, 0.918 mmol) was added to a mixture of ethanol (30 mL) and tris(triphenylphosphine)rhodium (I) chloride (50 mg, 0.054 mmol) in a Parr shaker. The glass reactor was sealed and flushed with argon, and then it was pressurized with hydrogen (50 psi). The mixture was shaken at ambient temperature for 24 hours, and concentrated. The residue was purified by silica gel chromatography (AnaLogix® SF10-8G; 50 micron silica; elution with 0-50% ethyl acetate in hexane at 12 mL/min) to provide the title compound (125 mg, 0.437 mmol, 47.6% yield) as a yellow solid. $^1$H NMR (300 MHz, CDCl$_3$) δ ppm 8.56 (dd, J=4.4, 1.7, 1H), 7.82 (dd, J=8.1, 1.7, 1H), 7.36 (dd, J=8.1, 4.4, 1H), 3.77-3.63 (m, 2H), 2.62 (s, 6H), 2.46-2.30 (m, 2H), 2.30-2.11 (m, 4H); MS (DCI/NH$_3$) m/e 287 (M+H)$^+$.

Example 26D 4-(3-(Dimethylamino)pyridin-2-yl)-4-(trifluoromethyl)cyclohex-1-enyl trifluoromethanesulfonate A solution of Example 26C (109 mg, 0.381 mmol) and N-phenyltrifluoromethane-sulfonamide (291.1 mg, 0.815 mmol) in tetrahydrofuran (5 mL) was chilled to −75° C. with a cooling bath, and treated with 1M lithium bis(trimethylsilyl)amide (0.92 mL, 0.920 mmol) in tetrahydrofuran. The reaction mixture was stirred at −75° C. for 1 hour. The cooling bath was removed and the mixture was allowed to stir overnight at ambient temperature. The reaction mixture was quenched with 1N sodium hydroxide (50 mL), extracted twice with ethyl acetate (50 mL), washed with brine, dried ($Na_2SO_4$) and concentrated. The residue was purified by silica gel chromatography (AnaLogix® SF10-8G; 50 micron silica; elution with 0-20% ethyl acetate in hexane at 12 mL/min) to provide the title compound (134 mg, 320 μmol, 84% yield) as a colorless oil. $^1$H NMR (300 MHz, $CDCl_3$) δ ppm 8.48 (dd, J=4.4, 1.7, 1H), 7.74 (dd, J=8.1, 1.7, 1H), 7.30 (dd, J=8.0, 4.4, 1H), 5.78 (dd, J=6.8, 1.3, 1H), 4.52-4.40 (m, 1H), 3.35-3.24 (m, 1H), 2.69-2.49 (m, 7H), 2.40-2.19 (m, 2H), 2.11-1.98 (m, 1H); MS (DCI/$NH_3$) m/e 419 (M+H)$^+$.

Example 26E 4-(3-(Dimethylamino)pyridin-2-yl)-4-(trifluoromethyl)-N-(4-(trifluoromethyl)phenyl)cyclohex-1-enecarboxamide A solution of Example 26D (131 mg, 0.313 mmol), 4-(trifluoromethyl)aniline (76 mg, 0.472 mmol), and triethylamine (0.088 mL, 0.631 mmol) in dimethylformamide (4 mL) was added to palladium(II) acetate (1.8 mg, 0.008 mmol) and 2-dicyclohexylphospino-2'-(dimethylamino)-biphenyl (6.2 mg, 0.016 mmol) in a pressure bottle under argon. The mixture was pressurized with carbon monoxide (60 psi), and stirred for 16 hours at ambient temperature, treated with ethyl acetate (50 mL), washed with water (50 mL) and brine, dried ($Na_2SO_4$) and concentrated. The residue was purified by silica gel chromatography twice [(1)AnaLogix® SF10-8G; 50 micron silica; elution with 0-40% ethyl acetate in hexane at 12 mL/min; (2)AnaLogix® SF10-8G; 50 micron silica; elution with 50% dichloromethane in hexane, then 50% ethyl acetate in hexane at 12 mL/min] to provide the title compound (84 mg, 184 μmol, 58.6% yield) as a light yellow foam. $^1$H NMR (300 MHz, $CDCl_3$) δ ppm 8.48 (dd, J=4.5, 1.8, 1H), 7.73 (dd, J=8.1, 1.7, 1H), 7.62 (d, J=8.8, 2H), 7.54 (d, J=8.9, 2H), 7.35 (s, 1H), 7.29 (dd, J=8.1, 4.5, 1H), 6.88 (d, J=5.4, 1H), 4.42 (dd, J=18.5, 6.1, 1H), 3.40-3.28 (m, 1H), 2.75-2.43 (m, 8H), 2.30-2.11 (m, 1H), 2.07-1.95 (m, 1H); MS (ESI) m/e 458 (M+H)$^+$; Calcd for $C_{22}H_{21}F_6N_3O \cdot 0.08H_2O \cdot 0.20$ EtOAc: C, 57.47, H, 4.81, N, 8.82; Found: C, 57.47, H, 4.55, N, 8.70.

Example 27

4-fluoro-4-(1,3-thiazol-2-yl)-N-{4-[(trifluoromethyl)sulfonyl]phenyl}cyclohex-1-ene-1-carboxamide Example 27A 8-(thiazol-2-yl)-1,4-dioxaspiro[4.5]decan-8-ol To a −78° C. solution of n-butyl lithium (10.4 mL, 2.5M in hexane, 26 mmol) in diethyl ether (20 mL) was added 2-bromothiazole (3.28 g, 1.8 mL, 20 mmol) slowly via syringe. The reaction mixture was stirred for 15 minutes, followed by the slow addition of 1,4-dioxaspiro[4.5]decan-8-one (4.22 g, 27 mmol) in diethyl ether (55 mL). The reaction mixture was allowed to warm to ambient temperature and stirred overnight. The reaction mixture was quenched with saturated aqueous ammonium chloride (50 mL) and extracted with two portions of ethyl acetate. The combined organic layers were concentrated. The residue was chromatographed on silica gel eluting with 0%-40% ethyl acetate-hexane to obtain the title compound (4.53 g, 94%). $^1$H NMR (300 MHz, DMSO-$d_6$) δ ppm 7.69 (d, J=3.2, 1H), 7.55 (d, J=3.2, 1H), 3.88 (s, 4H), 2.11 (td, J=4.2, 12.8, 2H), 1.93-1.80 (m, 2H), 1.80-1.53 (m, 4H).

MS (DCI) m/z 242 (M+H)$^+$.

Example 27B 2-(8-fluoro-1,4-dioxaspiro[4.5]decan-8-yl)thiazole

To a −78° C. solution of the product of Example 27A (4.53 g, 17.77 mmol) in methylene chloride (50 mL) was added diethylaminosulfur trifluoride (DAST) (4.18 g, 3.97 mL, 30.0 mmol). The reaction mixture was stirred at −78° C. for four hours, then allowed to warm to ambient temperature, and stirred overnight. The reaction mixture was then cooled to 0° C., quenched with saturated aqueous sodium bicarbonate, and extracted with methylene chloride. The organic layer was separated and concentrated. The resulting residue was chromatographed on silica gel, eluting with 0%-15% ethyl acetate-hexane to obtain the title compound (3.55 g, 78%). $^1$H NMR (300 MHz, DMSO-$d_6$) δ ppm 7.83 (m, 1H), 7.79 (m, 1H), 3.92 (s, 4H), 2.41-2.07 (m, 4H), 1.91-1.63 (m, 4H). MS (DCI) m/z 244 (M+H)$^+$.

Example 27C 4-fluoro-4-(thiazol-2-yl)cyclohexanone

To a solution of the product of Example 27B (3.55 g, 14.59 mmol) in dioxane (40 mL) was added 1M HCl (100 mL). The reaction mixture was stirred overnight at ambient temperature, quenched with 10M NaOH (10 mL) and extracted with three portions of 1:1 ethyl acetate-hexanes. The combined organic layers were concentrated. The resulting residue was chromatographed on silica gel eluting with 0%-20% ethyl acetate-hexane to obtain the title compound (2.15 g, 74%). $^1$H NMR (300 MHz, DMSO-$d_6$) δ ppm 7.82-7.95 (m, 2H), 2.61-2.72 (m, 6H), 2.24-2.42 (m, 2H).

MS (DCI) m/z 200 (M+H)$^+$.

Example 27D 4-fluoro-4-(thiazol-2-yl)cyclohex-1-enyl trifluoromethanesulfonate

To a −78° C. solution of the product of Example 27C (2.15 g, 10.79 mmol) and 1,1,1-trifluoro-N-phenyl-N-(trifluoromethylsulfonyl)methanesulfonamide (3.85 g, 10.79 mmol) in tetrahydrofuran (30 mL) was added lithium bis(trimethylsilyl)amide (1M in tetrahydrofuran, 13.95 mL, 13.95 mmol) over 5 minutes. The reaction mixture was allowed to warm to ambient temperature and stirred overnight. The reaction mixture was then diluted with ethyl acetate and hexane, and washed with 1N sodium hydroxide and brine. The organic layer was concentrated, and the residue chromatographed on silica gel eluting with 0%-20% ethyl acetate-hexane to obtain the title compound (2.54 g, 71%). $^1$H NMR (300 MHz, DMSO-$d_6$) δ ppm 7.85-7.95 (m, 2H), 5.90-6.08 (m, 1H), 2.94-3.21 (m, 1H), 2.74-2.95 (m, 1H), 2.58-2.74 (m, 1H), 2.17-2.50 (m, 3H). MS (DCI) m/z 332 (M+H)$^+$.

Example 27E 4-fluoro-4-(1,3-thiazol-2-yl)-N-{4-[(trifluoromethyl)sulfonyl]phenyl}cyclohex-1-ene-1-carboxamide The title compound was prepared using the procedure as described in Example 1E, except for substituting 4-(trifluoromethylsulfonyl)aniline for 4-(trifluoromethyl)aniline, and substituting the product of Example 27D for the product of Example 1D. $^1$H NMR (300 MHz, DMSO-$d_6$) δ ppm 10.52 (s, 1H), 7.99-8.23 (m, 4H), 7.82-7.96 (m, 2H), 6.79 (br s, 1H), 2.99-3.26 (m, 1H), 2.92 (m, 1H), 2.73 (m, 1H), 2.20-2.43 (m, 2H), 2.04-2.21 (m, 1H). MS (DCI) m/z 435 (M+H)$^+$. Calcd for $C_{17}H_{14}F_4N_2O_3S_2$: C, 47.00, H, 3.25, N, 6.45; Found: C, 47.26, H, 3.25, N, 6.33.

Example 28

(4R)-4-(3-chloropyridin-2-yl)-4-fluoro-N-{4-[(trifluoromethyl)sulfonyl]phenyl}cyclohex-1-ene-1-carboxamide The title compound was isolated from the chiral separation of Example 3 by Preparative Supercritical Fluid Chromatography (SFC) (Chiralpak AD-H 3 cm ID×25 cm column, 30% ethanol in SFC $CO_2$ at 150 bar, 40 g/min flow rate, 40° C. column temp) as the first eluting enantiomer. $^1$H NMR (300 MHz, CDCl$_3$) δ ppm 8.46 (d, J=4.7, 1H), 8.00 (d, J=8.9, 2H), 7.89 (d, J=8.9, 2H), 7.82-7.74 (m, 2H), 7.28-7.22 (m, 1H), 6.78 (s, 1H), 3.38-3.15 (m, 1H), 3.10-2.91 (m, 1H), 2.79-2.55 (m, 3H), 2.49-2.23 (m, 1H); MS (ESI) m/e 463 (M+H)$^+$; [α]$_D$: +13.9° (c 1.0, MeOH); Calcd for $C_{19}H_{15}ClF_4N_2O_3S$: C, 49.30, H, 3.27, N, 6.05; Found: C, 49.12, H, 3.19, N, 5.99.

Example 29

(4S)-4-(3-chloropyridin-2-yl)-4-fluoro-N-{4-[(trifluoromethyl)sulfonyl]phenyl}cyclohex-1-ene-1-carboxamide The title compound was isolated from the chiral separation of Example 3 by Prep SFC (Chiralpak AD-H 3 cm ID×25 cm column, 30% ethanol in SFC $CO_2$ at 150 bar, 40 g/min flow rate, 40° C. column temp) as the second eluting enantiomer. $^1$H NMR (300 MHz, CDCl$_3$) δ ppm 8.46 (ddd, J=4.5, 1.2, 0.7, 1H), 8.00 (d, J=8.9, 2H), 7.89 (d, J=8.9, 2H), 7.82-7.74 (m, 2H), 7.29-7.22 (m, 1H), 6.78 (s, 1H), 3.39-3.15 (m, 1H), 3.10-2.91 (m, 1H), 2.80-2.54 (m, 3H), 2.48-2.23 (m, 1H); MS (ESI) m/e 463 (M+H)$^+$; [α]$_D$: −12.2° (c 1.0, MeOH); Calcd for $C_{19}H_{15}ClF_4N_2O_3S$: C, 49.30, H, 3.27, N, 6.05; Found: C, 49.17, H, 3.06, N, 6.02.

Example 30

N-{4-[(difluoromethyl)sulfonyl]phenyl}-4-fluoro-4-(3-fluoropyridin-2-yl)cyclohex-1-ene-1-carboxamide The title compound was prepared using the procedure as described in Example 1E, except for substituting 4-(difluoromethylsulfonyl)aniline for 4-(trifluoromethyl)aniline, and substituting the product of Example 15D for the product of Example 1D. $^1$H NMR (300 MHz, DMSO-$d_6$) δ ppm 10.37 (s, 1H), 8.45 (d, J=4.6, 1H), 8.08 (d, J=9.0, 2H), 7.91 (d, J=9.0, 2H), 7.83 (ddd, J=1.3, 8.4, 11.8, 1H), 7.56 (app dt, J=4.2, 8.4, 1H), 7.23 (t, J=52.3, 1H(CF$_2$H)), 6.80 (br s, 1H), 3.28-3.04 (m, 1H), 2.98-2.67 (m, 1H), 2.61-2.35 (m, 3H), 2.35-2.03 (m, 1H). MS (DCI) m/z 429 (M+H)$^+$. Calcd for $C_{19}H_{16}F_4N_2O_3S$: C, 53.27, H, 3.76, N, 6.54; Found: C, 53.00, H, 3.61, N, 6.36.

Example 31

4-(3-chloropyridin-2-yl)-4-fluoro-N-[4-(pentafluoro-λ$^6$-sulfanyl)phenyl]cyclohex-1-ene-1-carboxamide The title compound was prepared using the procedure as described in Example 1 E, except for substituting 4-aminophenylsulfur pentafluoride (Aldrich) for 4-(trifluoromethyl)aniline. $^1$H NMR (300 MHz, DMSO-$d_6$) δ ppm 10.18 (s, 1H), 8.61-8.50 (m, 1H), 8.03 (dd, J=1.4, 8.1, 1H), 7.96-7.77 (m, 4H), 7.55-7.41 (m, 1H), 6.76 (s, 1H), 3.06 (ddd, J=11.5, 24.1, 47.8, 2H), 2.58-2.41 (m, 3H), 2.38-2.10 (m, 1H). MS (DCI) m/z 457 (M+H)$^+$. Calcd for $C_{18}H_{15}ClF_6N_2OS$: C, 47.32, H, 3.31, N, 6.13; Found: C, 47.27, H, 3.25, N, 6.01.

Example 32

4-(3-chloropyridin-2-yl)-4-fluoro-6-methyl-N-[4-(trifluoromethyl)phenyl]cyclohex-1-ene-1-carboxamide

Example 32A 4-(tert-butyldimethylsilyloxy)-2-methylcyclohexanone

To a 5.0 L round bottom flask containing 4-(tert-butyldimethylsilyloxy)cyclohexanone (7.03 g, 30.8 mmol) (Aldrich) was added THF (100 mL) and the reaction was cooled to −78° C. To the reaction mixture was added lithium bis(trimethylsilyl)amide (33.9 ml, 33.9 mmol) (Aldrich) and the reaction mixture was stirred for 30 minutes followed by the addition of iodomethane (2.309 ml, 36.9 mmol). The reaction mixture was stirred for 30 minutes at −78° C. and 2 hours at room temperature, quenched with saturated NH$_4$Cl, extracted with EtOAc (200 mL), dried (NaSO$_4$), filtered, and concentrated in vacuo. The residue was purified on SiO$_2$ and eluted with 0-20% ethyl acetate/hexane to give a white solid (6.40 g) in 86% yield. $^1$H NMR (300 MHz, CDCl$_3$) δ ppm 4.19-4.07 (m, 1H), 2.98-2.72 (m, 1H), 2.50-1.99 (m, 2H), 1.91-1.64 (m, 2H), 1.62-1.44 (m, 1H), 1.15 (dt, J=4.4, 6.8, 1H), 1.07-0.99 (m, 3H), 0.95-0.85 (m, 9H), 0.11 (d, J=1.6, 6H). MS (DCI$^+$) M/Z 243.

Example 32B tert-Butyldimethyl(6-methyl-1,4-dioxaspiro[4,5]decan-8-yloxy)silane To a 200 mL round bottom flask containing Example 32A (6.25 g, 25.8 mmol), ethylene glycol (1.725 mL, 30.9 mmol) and p-toluenesulfonic acid monohydrate (1.471 g, 7.73 mmol) (Aldrich) was added benzene (80 mL) and the reaction mixture was heated at reflux for 18 hr. The reaction mixture was quenched with sat NH$_4$OH, extracted with EtOAc (200 mL), dried (NaSO$_4$), filtered, and concentrated in vacuo. The residue was purified on SiO$_2$ and eluted with hexane ethyl acetate 0-20% to afford a colorless oil (6.57 g) in 89% yield. $^1$H NMR (300 MHz, CDCl$_3$) δ ppm 4.23-4.04 (m, 5H), 3.07-2.92 (m, 1H), 2.53-2.04 (m, 2H), 1.94-1.72 (m, 2H), 1.60-1.44 (m, 1H), 1.18 (dt, J=4.4, 6.8, 1H), 1.10-1.00 (m, 3H), 0.90-0.80 (m, 9H), 0.14 (d, J=1.6, 6H). MS (DCI+) M/Z 287 (M+H)+.

Example 32C

6-Methyl-1,4-dioxaspiro[4.5]decan-8-ol

To a 200 mL round bottom flask containing Example 32B (3.95 g, 13.79 mmol) was added TBAF (27.6 ml, 27.6 mmol) (Aldrich) and the reaction mixture was stirred at room temperature for 3 hours. The mixture was poured into saturated sodium bicarbonate, extracted with ethyl acetate (200 mL), dried over sodium sulfate, filtered, and concentrated in vacuo. The residue was purified on $SiO_2$ and eluted with hexane/ethyl acetate 0 to 40% over 60 minutes to afford a colorless oil (1.50 g) in 63% yield. $^1$H NMR (300 MHz, $CDCl_3$) δ ppm 4.00-3.86 (m, 4H), 3.69 (dt, J=5.4, 14.8, 1H), 2.25-1.19 (m, 7H), 0.94-0.81 (m, 3H). MS ($DCI^+$) M/Z 173 $(M+H)^+$.

Example 32D

6-Methyl-1,4-dioxaspiro[4.5]decan-8-one

To a 200 mL round bottom flask containing the product of Example 32C (1.50 g, 8.71 mmol) and DMP (4.06 g, 9.58 mmol) (Aldrich) was added methylene chloride (100 mL) and the reaction mixture was stirred for 1 hr at room temperature. The reaction mixture was quenched with saturated $NaHCO_3$ and extracted with EtOAc (200 mL), dried ($NaSO_4$), filtered, and concentrated in vacuo. The residue was purified on $SiO_2$ with hexane/ethylacetate 0-20% to afford a colorless oil (1.12 g) in 76% yield. $^1$H NMR (300 MHz, $CDCl_3$) δ ppm 4.20-3.95 (m, 4H), 2.63-1.97 (m, 6H), 1.94-1.74 (m, 1H), 1.04-0.83 (m, 3H). MS ($DCI^+$) M/Z 171 $(M+H)^+$.

Example 32E 8-(3-Chloropyridin-2-yl)-6-methyl-1,4-dioxaspiro[4.5]decan-8-ol

To a 200 mL round bottom flask containing diethyl ether (40 mL) was added n-butyllithium (IM) (3.41 ml, 8.52 mmol) (Aldrich) followed by addition of 2-bromo-3-chloropyridine (1.639 g, 8.52 mmol) (Aldrich) and the reaction was stirred for 1 hr at –65° C. Example 32D (1.45 g, 8.52 mmol) was added to the reaction in 20 mL of diethyl ether and stirred for 30 minutes. The reaction mixture was slowly warmed to room temperature and stirred for 2 hours, quenched with saturated $NaHCO_3$ and extracted with EtOAc (200 mL), dried ($NaSO_4$), filtered, and concentrated in vacuo. The material was purified on $SiO_2$ and eluted with hexane/ethyl acetate (20%) to give a colorless oil (1.295 g) in 53.4% yield. $^1$H NMR (300 MHz, $CDCl_3$) δ ppm 8.52-8.34 (m, 1H), 7.77-7.60 (m, 1H), 7.20 (ddd, J=4.6, 6.1, 7.9, 1H), 4.04-3.85 (m, 4H), 2.99-2.79 (m, 2H), 2.56-2.33 (m, 1H), 2.24-1.99 (m, 2H), 1.33-1.12 (m, 2H), 1.03-0.81 (d, 3H). MS ($DCI^+$) M/Z 284 $(M+H)^+$.

Example 32F

3-Chloro-2-(8-fluoro-6-methyl-1,4-dioxaspiro[4.5]decan-8-yl)pyridine

A solution of Example 32E (1.30 g, 4.58 mmol) in dichloromethane (100 mL) was cooled to –78° C., treated with diethylaminosulfur trifluoride (0.730 ml, 5.96 mmol) (Aldrich), and the reaction mixture was stirred at –78° C. for 2 hours. After 2 hours the reaction was partially complete and the mixture was allowed to stir for 2 additional hours. The reaction mixture was poured into dichloromethane (200 mL) and washed with saturated $Na_2CO_3$, dried over $Na_2SO_4$, and concentrated in vacuo. The material was purified on $SiO_2$ and eluted with hexane/ethyl acetate (20%) to give a white solid (0.625 g) in 48% yield. $^1$H NMR (300 MHz, $CDCl_3$) δ ppm 8.46 (dd, J=1.6, 4.7, 1H), 7.67 (dt, J=1.2C, 8.0, 1H), 7.17-7.09 (m, 1H), 4.17-3.92 (m, 4H), 2.72 (ddd, J=5.4, 10.7, 19.5, 3H), 2.57-2.50 (m, 1H), 2.25-2.15 (m, 1H), 2.06-1.94 (m, 1H), 1.83 (dd, J=6.0, 14.1, 1H), 1.08 (dd, J=6.9, 20.9, 3H). MS ($DCI^+$) M/Z 286 $(M+H)^+$.

Example 32G 4-(3-Chloropyridin-2-yl)-4-fluoro-2-methylcyclohexanone

To a 200 mL round bottom flask was added Example 32F (0.612 g, 2.142 mmol) in 10 mL of 1,4-dioxane. To the reaction was added 3N HCl (10 mL) and the reaction was stirred at room temperature for 5 hours. The reaction mixture was poured into $H_2O$, neutralized with $Na_2CO_3$, extracted with ethyl acetate (200 mL), dried over $Na_2SO_4$, and concentrated in vacuo. The material was purified on $SiO_2$ and eluted with hexane/ethyl acetate (20%) to give a white solid (0.43 g) in 84% yield. $^1$H NMR (300 MHz, $CDCl_3$) δ ppm 8.45-8.38 (m, 1H), 7.74 (dt, J=6.7, 13.6, 1H), 7.30-7.24 (m, 1H), 3.13-2.85 (m, 3H), 2.82-2.71 (m, 2H), 2.63-2.12 (m, 2H), 1.14 (dt, J=3.3, 10.1, 3H). MS (DCI+) M/Z 242 $(M+H)^+$.

Example 32H 4-(3-Chloropyridin-2-yl)-4-fluoro-6-methylcyclohex-1-enyl trifluoromethanesulfonate In a 200 mL round bottomed flask was added 1,1,1-trifluoro-N-phenyl-N-(trifluoromethylsulfonyl)methanesulfonamide (0.727 g, 2.034 mmol) (Aldrich) in THF (20 mL) and Example 32G (0.447 g, 1.849 mmol). The reaction was cooled to –78° C. and LiHMDS (0.95 mL, 1M in THF) (Aldrich) was added and the reaction was stirred at –78° C. for 1 hr. The reaction was warmed to room temperature and stirred for 1 hour. The mixture was concentrated in vacuo and taken up in ethyl acetate (200 mL). The organic portion was washed with saturated sodium bicarbonate (50 mL), brine (50 mL), dried (sodium sulfate), filtered and concentrated in vacuo. The crude material was purified on $SiO_2$ and eluted with hexane/ethyl acetate 4/1 to obtain the title compound as a white solid (0.58 g) in 84% yield. $^1$H NMR (300 MHz, $CDCl_3$) δ ppm 8.50-8.37 (m, 1H), 7.75 (dd, J=1.5, 8.0, 1H), 7.22 (dd, J=4.0, 8.4, 1H), 5.81-5.68 (m, 1H), 3.28-2.89 (m, 2H), 2.79-2.61 (m, 1H), 2.25-2.01 (m, 2H), 1.29 (s, 3H). MS (DCI+) M/Z 374 (M+H)+.

Example 32I 4-(3-chloropyridin-2-yl)-4-fluoro-6-methyl-N-[4-(trifluoromethyl)phenyl]cyclohex-1-ene-1-carboxamide To a 200 mL round bottom flask containing DMF (20 mL) was added palladium acetate (II) (0.014 g, 0.064 mmol) (Strem), Example 32H (0.120 g, 0.321 mmol), triethylamine (0.090 ml, 0.642 mmol) (Aldrich) and 4-(trifluoromethyl)aniline (0.067 g, 0.417 mmol) (Aldrich). The reaction mixture was subjected to CO(g) and the reaction was stirred at room temperature for 2 hours. The reaction was concentrated to ¼ volume and poured into 150 mL of ethyl acetate, washed with saturated bicarbonate, dried (sodium sulfate), filtered and concentrated in vacuo. The crude mixture was purified on SiO$_2$ (Analogix® SF65-200 g 35 micron silica) and eluted with CH$_2$Cl$_2$/hexane (1/1) with a 0 to 20% ethyl acetate gradient over 60 minutes with a 120 minute hold. Example 32I was obtained as a white solid in a 54% yield (72 mg). $^1$H NMR (300 MHz, DMSO-d$_6$) δ ppm 10.28 (s, 1H), 8.57 (d, J=4.5, 1H), 8.02 (dd, J=1.4, 8.1, 2H), 7.91 (s, 1H), 7.68 (d, J=8.7, 2H), 7.49 (dd, J=4.2, 7.9, 1H), 6.41 (s, 1H), 3.18-2.94 (m, 2H), 2.77-2.47 (m, 2H), 2.09-1.64 (m, 1H), 1.07 (d, J=6.8, 3H). MS (DCI+) M/Z 413 (M+H)+.

Example 33

4-(3-chloropyridin-2-yl)-4-(trifluoromethyl)-N-[4-(trifluoromethyl)phenyl]cyclohex-1-ene-1-carboxamide

Example 33A 3-(tert-Butyldimethylsilyloxy)-6-(3-chloropyridin-2-yl)-N,N-dimethyl-6-(trifluoromethyl)cyclohex-2-enamine A solution of Example 26A (612 mg, 2.95 mmol) and (E)-3-(tert-butyldimethylsilyloxy)-N,N-dimethylbuta-1,3-dien-1-amine (966 mg, 4.25 mmol) in toluene (2.5 mL) was heated on a microwave at 60° C. for 30 minutes, and then 70° C. for 30 minutes. Purified by silica gel chromatography (AnaLogix® SF25-40G; 50 micron silica; elution with 0-50% ethyl acetate in hexane at 30 mL/min) to provide the title compound (787 mg, 1.81 mmol, 61.4% yield) as a light yellow oil. MS (DCI/NH$_3$) m/e 435 (M+H)$^+$.

Example 33B 4-(3-Chloropyridin-2-yl)-4-(trifluoromethyl)cyclohex-2-enone

To a solution of Example 33A (787 mg, 1.81 mmol) in tetrahydrofuran (22 mL) was added 1N hydrochloric acid (4.0 mL, 4.0 mmol), and stirred overnight at ambient temperature. The reaction mixture was quenched with sodium bicarbonate solution (100 mL), extracted twice with ethyl acetate (100 mL), washed with brine, dried (Na$_2$SO$_4$) and concentrated. The residue was purified by silica gel chromatography (AnaLogix® SF15-24G; 50 micron silica; eluted with 0-40% ethyl acetate in hexane at 20 mL/min) to provide the title compound (449 mg, 1.63 mmol, 90% yield) as a white solid. $^1$H NMR (300 MHz, CDCl$_3$) δ ppm 8.58 (dd, J=4.5, 1.6, 1H), 7.77 (d, J=1.7, 1H), 7.74 (dd, J=2.5, 1.9, 1H), 7.29 (dd, J=8.1, 4.5, 1H), 6.15 (d, J=10.4, 1H), 3.62-3.52 (m, 1H), 2.57-2.46 (m, 1H), 2.41 (dd, J=12.7, 4.0, 1H), 2.32-2.18 (m, 1H); MS (DCI/NH$_3$) m/e 276 (M+H)$^+$.

Example 33C 4-(3-Chloropyridin-2-yl)-4-(trifluoromethyl)cyclohexanone

Example 33B (539 mg, 1.96 mmol) was added to a mixture of tetrahydrofuran (12 mL) and wet 5% platinum-on-carbon (112.7 mg) in a Parr shaker. The glass reactor was sealed and flushed with argon, and then it was pressurized with hydrogen (30 psi). The mixture was shaken at ambient temperature for 20 hours, filtered, rinsed with methanol, and concentrated. The residue was purified by silica gel chromatography (AnaLogix® SF15-24G; 50 micron silica, eluted with 0-40% ethyl acetate in hexane at 20 mL/min) to provide the title compound (318 mg, 1.15 mmol, 58.6% yield) as a white solid. $^1$H NMR (300 MHz, CDCl$_3$) δ ppm 8.63 (dd, J=4.4, 1.6, 1H), 7.79 (dd, J=8.2, 1.6, 1H), 7.30 (dd, J=8.0, 4.4, 1H), 3.65-3.50 (m, 2H), 2.53-2.38 (m, 2H), 2.31-2.13 (m, 4H); MS (DCI/NH$_3$) m/e 278 (M+H)$^+$.

Example 33D 4-(3-Chloropyridin-2-yl)-4-(trifluoromethyl)cyclohex-1-enyl trifluoromethanesulfonate A solution of Example 33C (304 mg, 1.095 mmol) and N-phenyltrifluoromethane-sulfonamide (430 mg, 1.20 mmol) in tetrahydrofuran (10 mL) was chilled to −75° C., treated with 1M lithium bis(trimethylsilyl)amide (1.3 mL, 1.3 mmol) in tetrahydrofuran, stirred at −75° C. for 1.5 hours, removed cooling bath, and stirred overnight at ambient temperature. The reaction mixture was quenched with 1N sodium hydroxide (100 mL), extracted twice with ethyl acetate (100 mL), washed with brine, dried (Na$_2$SO$_4$), and concentrated. The reaction mixture was purified by silica gel chromatography (AnaLogix® SF15-24G; 50 micron silica; eluted with 0-20% ethyl acetate in hexane at 20 mL/min) to provide the title compound (287 mg, 0.700 mmol, 64% yield) as a colorless oil. $^1$H NMR (300 MHz, CDCl$_3$) δ ppm 8.52 (dd, J=4.5, 1.6, 1H), 7.73 (dd, J=8.0, 1.5, 1H), 7.24 (dd, J=8.0, 4.4, 1H), 5.78 (d, J=6.7, 1H), 3.97-3.85 (m, 1H), 3.53-3.45 (m, 1H), 2.64-2.53 (m, 1H), 2.51-2.36 (m, 1H), 2.28-2.12 (m, 2H); MS (DCI/NH$_3$) m/e 410 (M+H)$^+$.

Example 33E 4-(3-Chloropyridin-2-yl)-4-(trifluoromethyl)-N-(4-(trifluoromethyl)phenyl)cyclohex-1-enecarboxamide A solution of Example 33D (283 mg, 0.691 mmol), 4-(trifluoromethyl)aniline (167 mg, 1.036 mmol), and triethylamine (0.193 mL, 1.38 mmol) in dimethylformamide (3 mL) was added to palladium(II) acetate (3.88 mg, 0.017 mmol) and 2-dicyclohexylphospino-2'-(dimethylamino)-biphenyl (13.59 mg, 0.035 mmol) in a pressure bottle under argon. The mixture was pressurized with carbon monoxide (60 psi), and stirred for 3.5 hours at ambient temperature, diluted with ethyl acetate (100 mL), washed with water (100 mL) and brine, dried (Na$_2$SO$_4$), and concentrated to a brown oil. The mixture was purified by silica gel chromatography twice [(1) AnaLogix® SF15-24G; 50 micron silica; eluted with 0-25% ethyl acetate in hexane at 20 mL/min; (2) AnaLogix® SF15-24G; 50 micron silica; eluted with dichloromethane at 20 mL/min] to provide the title compound (149 mg, 0.332 mmol, 48.1% yield) as a white solid. $^1$H NMR (300 MHz, CDCl$_3$) δ ppm 8.51 (dd, J=4.4, 1.6, 1H), 7.72 (dd, J=8.1, 1.6, 1H), 7.61 (d, J=8.9, 2H), 7.54 (d, J=8.8, 2H), 7.37 (s, 1H), 7.22 (dd, J=8.1, 4.5, 1H), 6.74 (d, J=4.9, 1H), 4.07-3.95 (m, 1H), 3.56-3.49 (m, 1H), 2.67-2.56 (m, 2H), 2.18-2.08 (m, 2H); MS (ESI) m/e 449 (M+H)$^+$; Calcd for C$_{20}$H$_{15}$ClF$_6$N$_2$O: C, 53.53, H, 3.37, N, 6.24; Found: C, 53.45, H, 3.10, N, 5.99.

Example 34

4-(3-chloropyridin-2-yl)-4-fluoro-N-(4-isopropylphenyl)cyclohex-1-ene-1-carboxamide The title compound was prepared using the procedure as described in Example 1E, except for substituting 4-isopropylaniline for 4-(trifluoromethyl)aniline. $^1$H NMR (300 MHz, CDCl$_3$) δ ppm 8.48-8.44 (m, 1H), 7.76 (dd, J=8.1, 1.5, 1H), 7.47 (d, J=8.6, 2H), 7.41 (s, 1H), 7.24 (dd, J=3.6, 0.6, 1H), 7.20 (d, J=8.6, 2H), 6.68 (s, 1H), 3.32-3.08 (m, 1H), 3.06-2.81 (m, 2H), 2.78-2.51 (m, 3H), 2.48-2.24 (m, 1H), 1.24 (d, J=6.9, 6H); MS (ESI) m/e 373 (M+H)$^+$; Calc'd for C$_{21}$H$_{22}$ClFN$_2$O: C, 67.65, H, 5.95, N, 7.51; Found: C, 67.42, H, 6.04, N, 7.42.

Example 35

4-(3-chloropyridin-2-yl)-4-fluoro-N-[4-(2,2,2-trifluoro-1-methylethyl)phenyl]cyclohex-1-ene-1-carboxamide Example 35A tert-Butyl 4-(3,3,3-trifluoroprop-1-en-2-yl)phenylcarbamate To a mixture of tert-butyl 4-bromophenylcarbamate (1.67 g, 6.14 mmol), potassium carbonate (3.38 g, 24.46 mmol), and tetrakis(triphenylphosphine)palladium (365 mg, 0.316 mmol), was added 4,4,6-trimethyl-2-(3,3,3-trifluoroprop-1-en-2-yl)-1,3,2-dioxaborinane (1.64 g, 7.39 mmol), and degassed 1,2-dimethoxyethane (40 mL) and water (20 mL). The mixture for refluxed for 2 hours, cooled to ambient temperature, added more of 4,4,6-trimethyl-2-(3,3,3-trifluoroprop-1-en-2-yl)-1,3,2-dioxaborinane (475 mg, 2.14 mmol) and tetrakis(triphenylphosphine)palladium-(189 mg, 0.164 mmol), and refluxed for 5 hours. The reaction mixture was cooled to room temperature, filtered, diluted with water (200 mL), extracted twice with ethyl acetate (200 mL), washed with brine, dried (Na$_2$SO$_4$) and concentrated to an orange oil. The residue was purified by silica gel chromatography (AnaLogix® SF25-40G; 50 micron silica; eluted with 0-15% ethyl acetate in hexane at 30 mL/min) to provide the title compound (1.223 g, 4.26 mmol, 69.4% yield) as a yellow solid. $^1$H NMR (300 MHz, DMSO-d$_6$) δ ppm 9.53 (s, 1H), 7.52 (d, J=8.8, 2H), 7.40 (d, J=8.4, 2H), 6.03-5.99 (m, 1H), 5.97-5.94 (m, 1H), 1.48 (s, 9H); MS (DCI/NH$_3$) m/e 305 (M+NH$_4$)$^+$.

Example 35B tert-Butyl 4-(1,1,1-trifluoropropan-2-yl)phenylcarbamate

Example 35A (1.223 g, 4.26 mmol) was added to a mixture of tetrahydrofuran (10 mL), methanol (20 mL), and 5% palladium-on-carbon (0.24 g) in a Parr shaker. The glass reactor was sealed and flushed with argon, and then pressurized with hydrogen (40 psi). The mixture was shaken at ambient temperature for 6 hours. The palladium was filtered off and rinsed with methanol. The filtrate was concentrated and purified by silica gel chromatography (AnaLogix® SF15-24G; 50 micron silica; eluted with 0-20% ethyl acetate in hexane at 20 mL/min) to provide the title compound (1.129 g, 3.90 mmol, 92% yield) as a pink solid. $^1$H NMR (300 MHz, DMSO-d$_6$) δ ppm 9.36 (s, 1H), 7.44 (d, J=8.6, 2H), 7.25 (d, J=8.7, 2H), 3.76-3.57 (m, 1H), 1.47 (s, 9H), 1.40 (d, J=7.2, 3H); MS (DCI/NH$_3$) m/e 307 (M+NH$_4$)$^+$.

Example 35C 4-(1,1,1-Trifluoropropan-2-yl)aniline

To a solution of Example 35B (1.059 g, 3.66 mmol) in dichloromethane (10 mL) was added trifluoroacetic acid (1.0 mL, 12.98 mmol), and stirred at ambient temperature for 3.5 hours. The reaction mixture was concentrated, treated with 3N sodium hydroxide (50 mL), extracted twice with diethyl ether (50 mL), washed with brine, dried (Na$_2$SO$_4$), and concentrated. The reaction mixture was purified the oil by silica gel chromatography (AnaLogix® SF15-24G; 50 micron silica; eluted with 0-30% ethyl acetate in hexane at 20 mL/min) to provide the title compound (635 mg, 3.36 mmol, 92% yield) as a liquid. $^1$H NMR (300 MHz, DMSO-d$_6$) δ ppm 6.99 (d, J=8.4, 2H), 6.53 (d, J=8.5, 2H), 5.08 (s, 2H), 3.55-3.41 (m, 1H), 1.35 (d, J=7.2, 3H); MS (DCI/NH$_3$) m/e 190 (M+H)$^+$.

Example 35D 4-(3-Chloropyridin-2-yl)-4-fluoro-N-(4-(1,1,1-trifluoropropan-2-yl)phenyl)cyclohex-1-enecarboxamide The title compound was prepared using the procedure as described in Example 1E, except for substituting Example 35C for 4-(trifluoromethyl)aniline. $^1$H NMR (300 MHz, CDCl$_3$) δ ppm 8.47-8.44 (m, 1H), 7.76 (dd, J=8.1, 1.3, 1H), 7.56 (d, J=8.6, 2H), 7.47 (s, 1H), 7.29 (d, J=8.6, 2H), 7.25-7.21 (m, 1H), 6.72-6.67 (m, 1H), 3.47-3.34 (m, 1H), 3.33-3.10 (m, 1H), 3.06-2.89 (m, 1H), 2.72-2.52 (m, 3H), 2.47-2.24 (m, 1H), 1.50 (d, J=7.3, 3H); MS (ESI) m/e 427 (M+H)$^+$; Calcd for C$_{21}$H$_{19}$ClF$_4$N$_2$O: C, 59.09, H, 4.49, N, 6.56; Found: C, 59.35, H, 4.49, N, 6.51.

Example 36

6-[3-(trifluoromethyl)pyridin-2-yl]-N-{4-[(trifluoromethyl)sulfonyl]phenyl}bicyclo[4.1.0]hept-3-ene-3-carboxamide Example 36A 8-(3-(trifluoromethyl)pyridine-2-yl)-1,4-dioxaspiro[4.5]decan-8-ol The title compound was prepared using a similar procedure as described in Example 1A, substituting 2-bromo-3-(trifluoromethyl)pyridine (4.61 g, 20.4 mmol) for 2-bromo-3-chloropyridine.
Yield 3.5 g, 57%

Example 36B 2-(1,4-Dioxaspiro[4,5]dec-7-en-8-yl)-3-(trifluoromethyl)pyridine

To a −78° C. solution of Example 36A (1.2 g, 3.96 mmol) in CH$_2$Cl$_2$ (25 mL) was added DAST (0.97 g, 0.76 mL, 5.75 mmol) and the reaction mixture was allowed to warm to ambient temperature. The mixture was quenched with water, diluted with EtOAc, and washed with water. Organic layer was separated, concentrated and chromatographed on silica gel (EtOAc-hexane, 0%-30%) to obtain the title compound (0.9 g, 80%). $^1$H NMR (300 MHz, DMSO-d$_6$) δ ppm 8.78 (m, 1H), 8.17 (dd, J=1.6, 8.2, 1H), 7.51 (m, 1H), 5.56 (m, 1H), 3.92 (s, 4H), 2.35 (m, 3H), 1.94 (dd, J=9.1, 16.3, 1H), 1.80 (t, J=6.5, 2H). MS (DCI) m/z 286 (M+H)$^+$.

Example 36C 2-(Spirobicyclo[4.1.0]heptane-3,2'-[1,3]dioxolane]-6-yl)-3-(trifluoromethyl)pyridine To a −78° C. solution of diethylzinc (3.86 mL, 3.86 mmol) (1M solution in hexane) in $CH_2Cl_2$ (4 mL) was added a solution of diiodomethane (0.62 mL, 7.71 mmol) in $CH_2Cl_2$ (2 mL). After the reaction mixture was stirred at −15° C. for 30 min, a solution of trifluoroacetic acid (0.30 mL, 3.86 mmol) in $CH_2Cl_2$ (2 mL) was added. After an additional 30 min of stirring, a solution of Example 36B (0.55 g, 1.93 mmol) in $CH_2Cl_2$ (2 mL) was added and reaction mixture stirred at 0° C. for 1 h. The reaction mixture was allowed to warm to ambient temperature stirred at ambient temperature for 16 h, and refluxed for 3 h, cooled to ambient temperature, quenched with water, and extracted with EtOAc. Organic phase was separated, concentrated in vacuo and the residue chromatographed on silica gel (EtOAc-Hexanes, 20-100%) to obtain the title compound (0.10 g, 17%). $^1$H NMR (300 MHz, DMSO-$d_6$) δ ppm 8.75 (dd, J=0.9, 4.8, 1H), 8.10 (m, 1H), 7.48 (m, 1H), 3.84 (m, 4H), 2.26-1.00 (m, 9H). MS (DCI) m/z 300 (M+H)$^+$.

Example 36D 6-(3-trifluoromethyl)pyridine-2-yl)bicyclo[4.1.0]heptan-3-one

To a solution of Example 36C (0.12 g, 0.40 mmol) in dioxane (2.5 mL) was added 3M aq. HCl (2.5 mL). The reaction mixture was allowed to warm to ambient temperature for 2 h before quenching with 3M aq. NaOH. Reaction mixture was diluted with EtOAc and washed twice with water. Organic phase was separated, concentrated in vacuo, and the residue chromatographed on silica gel (EtOAc-$CH_2Cl_2$, 10-100%) to obtain the title compound (0.06 g, 59%). $^1$H NMR (300 MHz, DMSO-$d_6$) δ ppm 8.79 (dd, J=0.9, 4.8, 1H), 8.16 (m, 1H), 7.53 (m, 1H), 2.78 (m, 1H), 2.35-2.08 (m, 5H), 1.67-1.53 (m, 1H), 1.23-1.07 (m, 2H). MS (DCI) m/z 256 (M+H)$^+$.

Example 36E 6-(3-trifluoromethyl)pyridine-2-yl)bicyclo[4.1.0]hept-2-en-3-yl trifluoromethanesulfonate The title compound was prepared using a similar procedure as described in Example 1D, substituting Example 36D (0.065 g, 0.255 mmol) for Example 1C. Yield 0.03 g, 30%. $^1$H NMR (300 MHz, DMSO-$d_6$) δ ppm 8.79 (m, 1H), 8.17 (m, 1H), 7.55 (m, 1H), 5.84 (dt, J=2.8, 5.4, 1H), 2.82 (m, 3H), 1.69 (m, 1H), 1.27 (m, 2H), 0.88 (t, J=5.6, 1H). MS (DCI) m/z 388 (M+H)$^+$.

Example 36F

6-[3-(trifluoromethyl)pyridin-2-yl]-N-{4-[(trifluoromethyl)sulfonyl]phenyl}bicyclo[4.1.0]hept-3-ene-3-carboxamide The title compound was prepared using a similar procedure as described in Example 1E, substituting Example 36E (0.03 g, 0.077 mmol) for Example 1D and substituting 4-(trifluoromethylsulfonyl)aniline for 4-(trifluoromethyl)aniline. Yield 0.023 g, 61%. $^1$H NMR (300 MHz, DMSO) δ ppm 10.46 (s, 1H), 8.81 (d, J=3.8, 1H), 8.26-7.96 (m, 5H), 7.55 (m, 1H), 6.68 (s, 1H), 2.75-0.76 (m, 7H). MS (DCI) m/z 491 (M+H)$^+$.

Example 37

4-(3-chloropyridin-2-yl)-4-fluoro-6-methyl-N-{4-[(trifluoromethyl)sulfonyl]phenyl}cyclohex-1-ene-1-carboxamide The title compound was prepared using the procedure as described in Example 32I, except for substituting 4-(trifluoromethylsulfonyl)aniline for 4-(trifluoromethyl)aniline. The product was obtained in 64% yield. $^1$H NMR (300 MHz, CDCl$_3$) δ ppm 8.52-8.43 (m, 1H), 8.01 (d, J=8.8, 1H), 7.95-7.87 (m, 2H), 7.83-7.66 (m, 2H), 7.30-7.19 (m, 1H), 6.54-6.41 (m, 1H), 3.09 (ddd, J=19.3, 37.0, 59.8, 3H), 2.77-2.59 (m, 1H), 2.05 (ddd, J=10.4, 14.1, 36.7, 1H), 1.16 (d, J=6.9, 3H). MS (DCI+) M/Z 477 (M+H)$^+$.

Example 38

4-(3-chloropyridin-2-yl)-4-methyl-N-[4-(trifluoromethyl)phenyl]cyclohex-1-ene-1-carboxamide

Example 38A 2-(3-chloropyridin-2-yl)propanenitrile

To a −78° C. solution of diisopropylamine (3.04 g, 4.28 mL, 30 mmol) was added n-butyl lithium (13.2 mL, 2.5M in hexane, 33 mmol). The reaction mixture was stirred for 20 minutes at −78° C., followed by the addition of propionitrile (1.65 g, 2.15 mL, 30 mmol). The reaction mixture was stirred for an additional 50 minutes, followed by the slow addition of 2-bromo-3-chloropyridine (1.92 g, 10 mmol) in THF (10 mL). The reaction was then allowed to warm to ambient temperature and stirred overnight. The reaction mixture was quenched with water and extracted with two portions of diethyl ether. The combined organic phases were washed with brine, concentrated, and the residue chromatographed on silica gel eluting with 30% ethyl acetate-hexane to obtain the title compound (1.52 g, 91%). $^1$H NMR (300 MHz, DMSO-$d_6$) δ ppm 8.59 (dd, J=1.5, 4.7, 1H), 8.02 (dd, J=1.5, 8.1, 1H), 7.48 (dd, J=4.7, 8.1, 1H), 4.73 (q, J=7.1, 1H), 1.59 (d, J=7.1, 3H). MS (DCI) m/z 167 (M+H)$^+$.

Example 38B

Ethyl 2-(3-chloropyridin-2-yl)propanoate

The product of Example 38A (1.15 g, 6.9 mmol) was dissolved in absolute ethanol (14 mL) and cooled to 0° C. Concentrated sulfuric acid (13.54 g, 7.36 mL, 138 mmol) was added, and the reaction mixture was allowed to warm to ambient temperature. The reaction was then heated at reflux for 2 hours, cooled, and poured onto ice. The mixture was neutralized with saturated aqueous sodium bicarbonate, and extracted with two portions of ethyl acetate. The organic layers were separated and concentrated to give the title compound (1.34 g, 91%) which was used without further purification. $^1$H NMR (300 MHz, DMSO-$d_6$) δ ppm 8.49 (dd, J=1.5, 4.7, 1H), 7.93 (dd, J=1.5, 8.1, 1H), 7.36 (dd, J=4.7, 8.1, 1H), 4.29 (q, J=7.1, 1H), 4.07 (q, J=7.1, 2H), 1.42 (d, J=7.1, 3H), 1.11 (t, J=7.1, 3H). MS (DCI) m/z 214 (M+H)$^+$.

Example 38C

2-(3-chloropyridin-2-yl)propan-1-ol

To a –15° C. solution of the product of Example 38B (1.34 g, 6.27 mmol) in tetrahydrofuran (25 mL) was added lithium aluminum hydride (0.238 g, 6.27 mmol). The reaction mixture was kept between –5° C. and –15° C. for 1 hour and then quenched by the addition of solid sodium sulfate decahydrate. The quenched reaction mixture was filtered through a pad of celite with ethyl acetate and the filtrate concentrated. The residue was chromatographed on silica gel with 35% ethyl acetate-hexane to give the title compound (0.90 g, 84%). $^1$H NMR (300 MHz, DMSO-d$_6$) δ ppm 8.49 (dd, J=1.5, 4.6, 1H), 7.85 (dd, J=1.6, 8.1, 1H), 7.26 (dd, J=4.6, 8.1, 1H), 4.70-4.55 (m, 1H), 3.82-3.62 (m, 1H), 3.59-3.39 (m, 2H), 1.16 (d, J=6.5, 3H). MS (DCI) m/z 172 (M+H)$^+$.

Example 38D

2-(3-chloropyridin-2-yl)propanal

To a –78° C. solution of dimethylsulfoxide (4.04 g, 3.67 mL, 51.7 mmol) in methylene chloride (25 mL) was added a solution of oxalyl chloride (3.28 g, 2.26 mL, 25.9 mmol) in methylene chloride (5 mL) over two minutes. The reaction mixture was stirred for 15 minutes, and then a solution of the product of Example 38C (0.74 g, 4.31 mmol) in methylene chloride (25 mL) was added over 8 minutes. The reaction was allowed to warm to ambient temperature and quenched with water. The quenched reaction mixture was extracted with methylene chloride, and the organic layer washed with brine and concentrated. The residue was chromatographed on silica gel eluting with 25% ethyl acetate-hexane to give the title compound (0.71 g, 97%). $^1$H NMR (300 MHz, DMSO-d$_6$) δ ppm 9.73 (s, 1H), 8.53 (dd, J=1.5, 4.7, 1H), 8.00 (dd, J=1.4, 8.1, 1H), 7.40 (dd, J=4.7, 8.1, 1H), 4.28 (q, J=7.0, 1H), 1.34 (d, J=7.0, 3H). MS (DCI) m/z 170 (M+H)$^+$.

Example 38E

4-(3-chloropyridin-2-yl)-4-methylcyclohex-2-enone

To a 0° C. solution of the product of Example 38D (0.71 g, 4.19 mmol) in diethyl ether (10 mL) was added a solution of potassium hydroxide (3M in methanol, 0.56 mL, 1.68 mmol), followed by methyl vinyl ketone (0.47 g, 0.55 mL, 6.70 mmol). The reaction was allowed to warm to ambient temperature and stirred overnight. The reaction mixture was diluted with diethyl ether, and washed with water and brine. The organic layer was concentrated, and the residue was chromatographed on silica gel eluting with 25% ethyl acetate-hexane to give the title compound (0.20 g, 22%). $^1$H NMR (300 MHz, DMSO-d$_6$) δ ppm 8.53 (dd, J=1.5, 4.6, 1H), 7.92 (dd, J=1.5, 8.0, 1H), 7.45-7.26 (m, 2H), 5.92 (d, J=10.2, 1H), 2.82-2.67 (m, 1H), 2.64-2.52 (m, 1H), 2.31 (ddd, J=4.8, 7.2, 17.3, 1H), 2.12-2.00 (m, 1H). MS (DCI) m/z 222 (M+H)$^+$.

Example 38F

4-(3-chloropyridin-2-yl)-4-methylcyclohexanone

A solution of the product of Example 38E (0.225 g, 1.015 mmol) in DMF was added to 5% Pt—C, wet (225 mg, 1.153 mmol) in a 50 ml pressure bottle. The mixture was pressurized with hydrogen (40 psi), stirred for 16 hours at ambient temperature, filtered to remove catalyst, and concentrated. The residue was chromatographed on silica gel eluting with 30% ethyl acetate-hexanes to give the title compound (90 mg, 40%). $^1$H NMR (300 MHz, DMSO-d$_6$) δ ppm 8.55 (dd, J=1.5, 4.6, 1H), 7.91 (dd, J=1.5, 8.0, 1H), 7.36 (dd, J=4.6, 8.0, 1H), 2.96-2.77 (m, 2H), 2.26 (dd, J=5.4, 8.1, 4H), 2.03-1.84 (m, 2H), 1.46 (s, 3H). MS (DCI) m/z 224 (M+H)$^+$.

Example 38G

4-(3-chloropyridin-2-yl)-4-methylcyclohex-1-enyl trifluoromethanesulfonate

To a –78° C. solution of the product of Example 38F (90 mg, 0.40 mmol) and 1,1,1-trifluoro-N-phenyl-N-(trifluoromethylsulfonyl)methanesulfonamide (144 mg, 0.40 mmol) in tetrahydrofuran (2.5 mL) was added lithium bis(trimethylsilyl)amide (1M in tetrahydrofuran, 0.48 mL, 0.48 mmol). The reaction mixture was allowed to warm to ambient temperature and stirred overnight. The reaction mixture was then diluted with ethyl acetate and hexane, and washed with 1N sodium hydroxide and brine. The organic layer was concentrated, and the residue chromatographed on silica gel eluting with 8% ethyl acetate-hexane to obtain the title compound (117 mg, 82%). $^1$H NMR (300 MHz, DMSO-d$_6$) δ ppm 8.46 (dd, J=1.6, 4.5, 1H), 7.88 (dd, J=1.6, 8.0, 1H), 7.33 (dd, J=4.5, 8.0, 1H), 5.99-5.86 (m, 1H), 3.21-3.07 (m, 1H), 2.78-2.57 (m, 1H), 2.43-2.28 (m, 2H), 2.17-1.90 (m, 2H), 1.43 (s, 3H). MS (DCI) m/z 356 (M+H)$^+$.

Example 38H

4-(3-chloropyridin-2-yl)-4-methyl-N-[4-(trifluoromethyl)phenyl]cyclohex-1-ene-1-carboxamide The title compound was prepared using the procedure as described in Example 1E, except for substituting the product of Example 38G for the product of Example 1D. $^1$H NMR (300 MHz, DMSO-d$_6$) δ ppm 9.86 (s, 1H), 8.46 (d, J=3.2, 1H), 7.99-7.79 (m, 3H), 7.64 (d, J=8.6, 2H), 7.31 (dd, J=4.5, 8.0, 1H), 6.85 (br s, 1H), 3.45-3.09 (m, 2H), 2.65-2.21 (m, 2H), 2.15-1.83 (m, 2H), 1.44 (s, 3H). MS (DCI) m/z 395 (M+H)$^+$. Calcd for $C_{20}H_{18}ClF_3N_2O.0.2H_2O$: C, 60.29, H, 4.65, N, 7.03; Found: C, 60.10, H, 4.48, N, 6.89.

Example 39

N-(4-tert-butylphenyl)-4-(3-chloropyridin-2-yl)-4-methylcyclohex-1-ene-1-carboxamide The title compound was prepared using the procedure as described in Example 1E, except for substituting 4-tert-butylaniline for 4-(trifluoromethyl)aniline, and substituting the product of Example 38G for the product of Example 1D. $^1$H NMR (300 MHz, DMSO-d$_6$) δ ppm 9.41 (s, 1H), 8.47 (dd, J=1.5, 4.5, 1H), 7.87 (dd, J=1.5, 8.0, 1H), 7.55 (d, J=8.7, 2H), 7.41-7.20 (m, 3H), 6.76 (br s, 1H), 3.42-3.08 (m, 2H), 2.62-2.22 (m, 2H), 2.15-1.83 (m, 2H), 1.43 (s, 3H), 1.25 (s, 9H). MS (DCI) m/z 383 (M+H)$^+$. Calcd for $C_{23}H_{27}ClN_2O.0.2H_2O$: C, 71.47, H, 7.14, N, 7.25; Found: C, 71.50, H, 6.89, N, 6.96.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of formula (I)

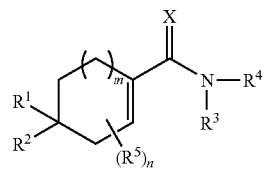

or a pharmaceutically acceptable salt, wherein
$R^1$ is a monocyclic heteroaryl, which is optionally substituted with 1, 2, 3, 4, or 5 substituents as represented by $R^6$ groups;
$R^2$ is halogen, alkyl, haloalkyl, —CN, —O(alkyl), —O(haloalkyl), —OH, —NH$_2$, —N(H)(alkyl), or —N(alkyl)$_2$; or
$R^2$ and the adjacent carbon atom, together with the carbon atom to which $R^2$ is attached, form a 3-6 membered monocyclic cycloalkyl ring that is optionally substituted with 1, 2, 3, or 4 substituents independently selected from the group consisting of alkyl, hydroxyalkyl, alkoxyalkyl, haloalkoxyalkyl, haloalkyl, arylalkyl, aryl, aminoalkyl, amino, and halogen, wherein the aryl and the aryl moiety of the arylalkyl are each independently unsubstituted or substituted with 1, 2, 3, 4, or 5 substituents selected from the group consisting of alkyl, alkenyl, alkynyl, halogen, OH, O(alkyl), O(haloalkyl), amino, and haloalkyl;
$R^3$ is hydrogen or $C_{1-6}$ alkyl;
$R^4$ is aryl, heteroaryl, cycloalkyl, cycloalkenyl, or heterocycle, wherein each $R^4$ is optionally substituted with 1, 2, 3, 4, 5, or 6 substituents as represented by $R^7$ groups;
$R^5$ represents an optional substituent on the cycloalkene ring, and is haloalkyl, halogen, —OH, —NO$_2$, NH$_2$, N(H)(alkyl), N(alkyl)$_2$, alkyl, alkenyl, alkynyl, or -G$^1$;
X is O;
m is 1;
n is 0 or 1;
$R^7$, at each occurrence, is independently alkyl, alkenyl, alkynyl, oxo, —NO$_2$, —CN, halogen, -G$^2$, —OR$^a$, —OC(O)R$^a$, —SR$^a$, —SF$_5$, —S(O)R$^b$, —S(O)$_2$R$^b$, —S(O)$_2$N(R$^a$)(R$^c$), —N(R$^a$)(R$^c$), —N(R$^c$)C(O)R$^a$, —N(R$^c$)S(O)$_2$R$^b$, —N(R$^c$)C(O)N(R$^a$)(R$^c$), —N(R$^c$)S(O)$_2$N(R$^a$)(R$^c$), —C(O)R$^a$, —C(O)OR$^a$, —C(O)N(R$^a$)(R$^c$), haloalkyl, —(CR$^j$R$^k$)$_p$—CN, —(CR$^j$R$^k$)$_p$—OR$^a$, —(CR$^j$R$^k$)$_p$—SR$^a$, —(CR$^j$R$^k$)$_p$—OC(O)R$^a$, —(CR$^j$R$^k$)$_p$—S(O)$_2$R$^b$, —(CR$^j$R$^k$)$_p$—S(O)R$^b$, —(CR$^j$R$^k$)$_p$N(R$^a$)(R$^c$), —(CR$^j$R$^k$)$_p$—N(R$^c$)C(O)R$^a$, —(CR$^j$R$^k$)$_p$—N(R$^c$)S(O)$_2$R$^b$, —(CR$^j$R$^k$)$_p$—N(R$^c$)C(O)N(R$^a$)(R$^c$), —(CR$^j$R$^k$)$_p$—N(R$^c$)S(O)$_2$N(R$^a$)(R$^c$), —(CR$^j$R$^k$)$_p$—C(O)R$^a$, —(CR$^j$R$^k$)$_p$—C(O)OR$^a$, —(CR$^j$R$^k$)$_p$—C(O)N(R$^a$)(R$^c$), or —(CR$^j$R$^k$)$_p$-G$^2$;
$R^a$, at each occurrence, is independently hydrogen, alkyl, haloalkyl, -G$^2$, or —(CR$^u$R$^v$)$_w$-G$^2$;

$R^b$, at each occurrence, is independently alkyl, haloalkyl, -G$^2$, or —(CR$^u$R$^v$)$_w$-G$^2$;
$G^1$ and $G^2$, are each independently aryl, heteroaryl, cycloalkyl, cycloalkenyl, or heterocycle; each of which is independently unsubstituted or substituted with 1, 2, 3, 4, 5, or 6 substituents as represented by $R^8$ groups;
$R^6$, at each occurrence, is independently alkyl, alkenyl, alkynyl, —NO$_2$, —CN, halogen, —OR$^d$, —OC(O)R$^d$, —SR$^d$, —S(O)R$^e$, —S(O)$_2$R$^e$, —S(O)$_2$N(R$^d$)(R$^f$), —N(R$^d$)(R$^f$), —N(R$^f$)C(O)R$^d$, —N(R$^f$)S(O)$_2$R$^e$, —N(R$^f$)C(O)N(R$^d$)(R$^f$), —N(R$^f$)S(O)$_2$N(R$^d$)(R$^f$), —C(O)R$^d$, —C(O)OR$^d$, —C(O)N(R$^d$)(R$^f$), haloalkyl, —(CR$^s$R$^t$)$_q$—CN, —(CR$^s$R$^t$)$_q$—OR$^a$, —(CR$^s$R$^t$)$_q$—OC(O)R$^d$, —(CR$^s$R$^t$)$_q$—SR$^d$, —(CR$^s$R$^t$)$_q$—S(O)R$^e$, —(CR$^s$R$^t$)$_q$—S(O)$_2$R$^e$, —(CR$^s$R$^t$)$_q$—N(R$^d$)(R$^f$), —(CR$^s$R$^t$)$_q$—N(R$^f$)C(O)R$^d$, —(CR$^s$R$^t$)$_q$—N(R$^f$)S(O)$_2$R$^e$, —(CR$^s$R$^t$)$_q$—N(R$^f$)C(O)N(R$^d$)(R$^f$), —(CR$^s$R$^t$)$_q$—N(R$^f$)S(O)$_2$N(R$^d$)(R$^f$), —(CR$^s$R$^t$)$_q$—C(O)R$^d$, —(CR$^s$R$^t$)$_q$—C(O)OR$^d$, or —(CR$^s$R$^t$)$_q$—C(O)N(R$^d$)(R$^f$);
$R^8$, at each occurrence, is independently alkyl, alkenyl, alkynyl, oxo, —NO$_2$, —CN, halogen, —OR$^d$, —OC(O)R$^d$, —SR$^d$, —S(O)R$^e$, —S(O)$_2$R$^e$, —S(O)$_2$N(R$^d$)(R$^f$), —N(R$^d$)(R$^f$), —N(R$^f$)C(O)R$^d$, —N(R$^f$)S(O)$_2$R$^e$, —N(R$^f$)C(O)N(R$^d$)(R$^f$), —N(R$^f$)S(O)$_2$N(R$^d$)(R$^f$), —C(O)R$^d$, —C(O)OR$^d$, —C(O)N(R$^d$)(R$^f$), haloalkyl, —(CR$^s$R$^t$)$_q$—CN, —(CR$^s$R$^t$)$_q$—OR$^a$, —(CR$^s$R$^t$)$_q$—OC(O)R$^d$, —(CR$^s$R$^t$)$_q$—SR$^d$, —(CR$^s$R$^t$)$_q$—S(O)R$^e$, —(CR$^s$R$^t$)$_q$—S(O)$_2$R$^e$, —(CR$^s$R$^t$)$_q$—N(R$^d$)(R$^f$), —(CR$^s$R$^t$)$_q$—N(R$^f$)C(O)R$^d$, —(CR$^s$R$^t$)$_q$—N(R$^f$)C(O)N(R$^d$)(R$^f$), —(CR$^s$R$^t$)$_q$—N(R$^f$)S(O)$_2$N(R$^d$)(R$^f$), —(CR$^s$R$^t$)$_q$—C(O)R$^d$, —(CR$^s$R$^t$)$_q$—C(O)OR$^d$, or —(CR$^s$R$^t$)$_q$—C(O)N(R$^d$)(R$^f$);
$R^c$, $R^d$ and $R^f$, at each occurrence, are each independently hydrogen, alkyl, or haloalkyl;
$R^e$, at each occurrence, is independently alkyl or haloalkyl;
$R^j$, $R^k$, $R^s$, $R^t$, $R^u$, and $R^v$, at each occurrence, are each independently hydrogen, halogen, alkyl, or haloalkyl; and
p, q, and w, at each occurrence, are each independently 1, 2, 3, or 4.

2. The compound according to claim 1 or a pharmaceutically acceptable salt thereof, wherein $R^2$ is halogen or alkyl.

3. The compound according to claim 1 or a pharmaceutically acceptable salt thereof, wherein the monocyclic heteroaryl is pyridinyl.

4. The compound according to claim 1 or a pharmaceutically acceptable salt thereof, wherein $R^4$ is optionally substituted heteroaryl.

5. The compound according to claim 1 or a pharmaceutically acceptable salt thereof, wherein $R^4$ is optionally substituted phenyl.

6. The compound according to claim 5 or a pharmaceutically acceptable salt thereof, wherein $R^2$ is halogen or alkyl.

7. The compound according to claim 1 having formula (III), or a pharmaceutically acceptable salt thereof

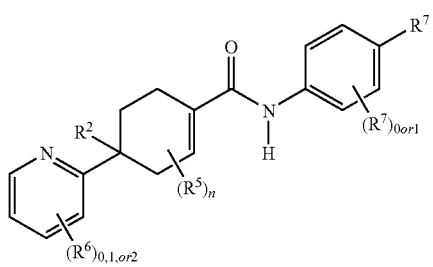

wherein $R^2$, $R^5$, $R^6$, $R^7$, and n are as defined in formula (I).

8. The compound of claim 7 or a pharmaceutically acceptable salt thereof wherein $R^2$ is halogen or alkyl.

9. The compound of claim 8 or a pharmaceutically acceptable salt thereof wherein n is 0.

10. The compound according to claim 1 or a pharmaceutically acceptable salt thereof, selected from the group consisting of 4-(3-chloropyridin-2-yl)-4-fluoro-N-[4-(trifluoromethyl) phenyl]cyclohex-1-ene-1-carboxamide;
N-(4-chlorophenyl)-4-(3-chloropyridin-2-yl)-4-fluorocyclohex-1-ene-1-carboxamide;
4-(3-chloropyridin-2-yl)-4-fluoro-N-{4-[(trifluoromethyl)sulfonyl]phenyl}cyclohex-1-ene-1-carboxamide;
N-(4-tert-butylphenyl)-4-(3-chloropyridin-2-yl)-4-fluorocyclohex-1-ene-1-carboxamide;
4-(3-chloropyridin-2-yl)-4-fluoro-N-[4-(trifluoromethoxy)phenyl]cyclohex-1-ene-1-carboxamide;
4-(3-chloropyridin-2-yl)-N-[4-(1-cyano-1-methylethyl) phenyl]-4-fluorocyclohex-1-ene-1-carboxamide;
4-(3-chloropyridin-2-yl)-4-methoxy-N-{4-[(trifluoromethyl)sulfonyl]phenyl}cyclohex-1-ene-1-carboxamide;
4-(3-chloropyridin-2-yl)-4-methoxy-N-[4-(trifluoromethyl)phenyl]cyclohex-1-ene-1-carboxamide;
4-fluoro-4-(3-methylpyridin-2-yl)-N-[4-(trifluoromethyl) phenyl]cyclohex-1-ene-1-carboxamide;
4-fluoro-4-(3-methylpyridin-2-yl)-N-[4-(trifluoromethoxy)phenyl]cyclohex-1-ene-1-carboxamide;
4-fluoro-4-(3-methylpyridin-2-yl)-N-{4-[(trifluoromethyl)sulfonyl]phenyl}cyclohex-1-ene-1-carboxamide;
N-(4-chlorophenyl)-4-fluoro-4-(3-methylpyridin-2-yl)cyclohex-1-ene-1-carboxamide;
N-(4-tert-butylphenyl)-4-fluoro-4-(3-methylpyridin-2-yl) cyclohex-1-ene-1-carboxamide;
4-fluoro-4-(3-fluoropyridin-2-yl)-N-[4-(trifluoromethyl) phenyl]cyclohex-1-ene-1-carboxamide;
N-(4-tert-butylphenyl)-4-fluoro-4-(3-fluoropyridin-2-yl)cyclohex-1-ene-1-carboxamide;
4-fluoro-4-(3-fluoropyridin-2-yl)-N-[5-(trifluoromethyl) pyridin-2-yl]cyclohex-1-ene-1-carboxamide;
4-fluoro-4-(3-fluoropyridin-2-yl)-N-{4-[(trifluoromethyl)sulfonyl]phenyl}cyclohex-1-ene-1-carboxamide;
4-fluoro-4-(3-fluoropyridin-2-yl)-N-[4-(pentafluoro-$\lambda^6$-sulfanyl)phenyl]cyclohex-1-ene-1-carboxamide;
4-fluoro-4-(1,3-thiazol-2-yl)-N-[4-(trifluoromethyl)phenyl]cyclohex-1-ene-1-carboxamide;
4-fluoro-4-(1,3-thiazol-2-yl)-N-{4-[(trifluoromethyl)sulfonyl]phenyl}cyclohex-1-ene-1-carboxamide;
(4R)—N-(4-chlorophenyl)-4-(3-chloropyridin-2-yl)-4-fluorocyclohex-1-ene-1-carboxamide;
(4S)—N-(4-chlorophenyl)-4-(3-chloropyridin-2-yl)-4-fluorocyclohex-1-ene-1-carboxamide;
(4R)-4-(3-chloropyridin-2-yl)-4-fluoro-N-[4-(trifluoromethyl)phenyl]cyclohex-1-ene-1-carboxamide;
(4S)-4-(3-chloropyridin-2-yl)-4-fluoro-N-[4-(trifluoromethyl)phenyl]cyclohex-1-ene-1-carboxamide;
4-[3-(dimethylamino)pyridin-2-yl]-4-(trifluoromethyl)-N-[4-(trifluoromethyl)phenyl]cyclohex-1-ene-1-carboxamide;
4-fluoro-4-(1,3-thiazol-2-yl)-N-{4-[(trifluoromethyl)sulfonyl]phenyl}cyclohex-1-ene-1-carboxamide;
(4R)-4-(3-chloropyridin-2-yl)-4-fluoro-N-{4-[(trifluoromethyl)sulfonyl]phenyl}cyclohex-1-ene-1-carboxamide;
(4S)-4-(3-chloropyridin-2-yl)-4-fluoro-N-{4-[(trifluoromethyl)sulfonyl]phenyl}cyclohex-1-ene-1-carboxamide;
N-{4-[(difluoromethyl)sulfonyl]phenyl}-4-fluoro-4-(3-fluoropyridin-2-yl)cyclohex-1-ene-1-carboxamide;
4-(3-chloropyridin-2-yl)-4-fluoro-N-[4-(pentafluoro-$\lambda^6$-sulfanyl)phenyl]cyclohex-1-ene-1-carboxamide;
4-(3-chloropyridin-2-yl)-4-fluoro-6-methyl-N-[4-(trifluoromethyl)phenyl]cyclohex-1-ene-1-carboxamide;
4-(3-chloropyridin-2-yl)-4-(trifluoromethyl)-N-[4-(trifluoromethyl)phenyl]cyclohex-1-ene-1-carboxamide;
4-(3-chloropyridin-2-yl)-4-fluoro-N-(4-isopropylphenyl) cyclohex-1-ene-1-carboxamide;
4-(3-chloropyridin-2-yl)-4-fluoro-N-[4-(2,2,2-trifluoro-1-methylethyl)phenyl]cyclohex-1-ene-1-carboxamide;
4-(3-chloropyridin-2-yl)-4-fluoro-6-methyl-N-{4-[(trifluoromethyl)sulfonyl]phenyl}cyclohex-1-ene-1-carboxamide;
4-(3-chloropyridin-2-yl)-4-methyl-N-[4-(trifluoromethyl) phenyl]cyclohex-1-ene-1-carboxamide; and
N-(4-tert-butylphenyl)-4-(3-chloropyridin-2-yl)-4-methylcyclohex-1-ene-1-carboxamide.

11. A pharmaceutical composition comprising a therapeutically effective amount of a compound of formula (I) according to claim 1 or a pharmaceutically acceptable salt thereof, and a pharmaceutically acceptable carrier.

12. The pharmaceutical composition of claim 11 further comprises acetaminophen or one or more nonsteroidal anti-inflammatory drug, or a combination thereof.

13. The pharmaceutical composition of claim 12 wherein the nonsteroidal anti-inflammatory drug is ibuprofen.

* * * * *